US011236325B2

(12) United States Patent
Kemp et al.

(10) Patent No.: US 11,236,325 B2
(45) Date of Patent: Feb. 1, 2022

(54) METHODS FOR NUCLEIC ACID CAPTURE

(71) Applicant: ZYMO RESEARCH CORPORATION, Irvine, CA (US)

(72) Inventors: Ryan Kemp, Irvine, CA (US); Jonathan A. Claypool, Irvine, CA (US); Marc E. Van Eden, North Tustin, CA (US); Xi-Yu Jia, Newport Beach, CA (US)

(73) Assignee: ZYMO RESEARCH CORPORATION, Irvine, CA (US)

( * ) Notice: Subject to any disclaimer, the term of this patent is extended or adjusted under 35 U.S.C. 154(b) by 0 days.

(21) Appl. No.: 15/961,995

(22) Filed: Apr. 25, 2018

(65) Prior Publication Data
US 2018/0371450 A1 Dec. 27, 2018

Related U.S. Application Data

(62) Division of application No. 14/619,037, filed on Feb. 10, 2015.

(60) Provisional application No. 61/937,824, filed on Feb. 10, 2014, provisional application No. 62/013,668, filed on Jun. 18, 2014, provisional application No. 62/079,358, filed on Nov. 13, 2014.

(51) Int. Cl.
*C12N 15/10* (2006.01)
(52) U.S. Cl.
CPC .............................. *C12N 15/1006* (2013.01)
(58) Field of Classification Search
None
See application file for complete search history.

(56) References Cited

U.S. PATENT DOCUMENTS

| 5,010,183 | A | 4/1991 | Macfarlane |
| 5,300,635 | A | 4/1994 | Macfarlane |
| 5,596,092 | A | 1/1997 | Schneider |
| 5,728,822 | A | 3/1998 | Macfarlane |
| 6,410,274 | B1 | 6/2002 | Bhikhabhai |
| 6,602,679 | B2 | 8/2003 | Giri |
| 6,797,476 | B2 | 9/2004 | Lander et al. |
| 6,821,757 | B2 | 11/2004 | Sauer et al. |
| 7,173,124 | B2 | 2/2007 | Deggerdal et al. |
| 7,285,651 | B2 | 10/2007 | Lander et al. |
| 7,326,555 | B2 | 2/2008 | Konz et al. |
| 7,754,873 | B2 | 7/2010 | Jia et al. |
| 7,767,399 | B2 | 8/2010 | Murphy et al. |
| 7,989,614 | B2 | 8/2011 | Deggerdal et al. |
| 8,460,920 | B2 | 6/2013 | de Vocht et al. |
| 8,470,585 | B2 | 6/2013 | de Vocht et al. |
| 8,679,744 | B2 | 3/2014 | Singer |
| 8,691,969 | B2 | 4/2014 | Deggerdal et al. |
| 2002/0012990 | A1 | 1/2002 | Jackson et al. |
| 2002/0151048 | A1 | 10/2002 | Lander et al. |
| 2005/0032105 | A1* | 2/2005 | Bair ................... C12N 15/1003 435/6.12 |
| 2005/0271595 | A1 | 12/2005 | Brown |
| 2008/0113348 | A1 | 5/2008 | Singer |
| 2008/0138886 | A1 | 6/2008 | Murphy et al. |
| 2012/0202268 | A1 | 8/2012 | de Vocht et al. |

FOREIGN PATENT DOCUMENTS

| EP | 0442026 | 8/1991 |
| EP | 1018549 | 7/2000 |
| EP | 2426201 | 3/2012 |
| WO | WO 1993/025711 | 12/1993 |
| WO | WO 2001/055446 | 8/2001 |
| WO | WO 02/090539 | 11/2002 |
| WO | WO 2003/097797 | 11/2003 |
| WO | WO 2006/085907 | 8/2006 |
| WO | WO 2011/045378 | 4/2011 |
| WO | WO 2011/045381 | 4/2011 |

OTHER PUBLICATIONS

De Majumdar et al., "Elucidating the regulon of multidrug resistance regulator rarA in *Klebsiella pneumoniae*," *Antimicrob Agents Chemother.*, 57(4): 1603-9, 2013.
Declaration of Ryan Kemp under 37 C.F.R. § 1.132, submitted in U.S. Appl. No. 14/619,037, dated Jul. 19, 2017.
Eskilsson et al., "DNA-surfactant complexes at solid surfaces," *Langmuir*, 17: 1666-1669, 2001.
International Search Report and Written Opinion issued in International Application No. PCT/US2015/015208, dated May 20, 2015.
Office Communication issued in European Patent Application No. 15706608.5, dated Jul. 18, 2017.
Office Communication issued in European Patent Application No. 15706608.5, dated Aug. 21, 2018.
Office Communication issued in U.S. Appl. No. 14/619,037, dated Aug. 16, 2018.
Office Communication issued in U.S. Appl. No. 14/619,037, dated Oct. 20, 2017.
Office Communication issued in U.S. Appl. No. 14/619,037, dated Jan. 19, 2017.
Office Communication issued in U.S. Appl. No. 14/619,037, dated Jul. 12, 2016.
Office Communication issued in U.S. Appl. No. 14/619,037, dated Jan. 8, 2016.
Salimullah et al., "Tunable fractionation of nucleic acids," *Biotechniques*, 47(6): 1041-1043, 2009.

(Continued)

*Primary Examiner* — Arthur S Leonard
(74) *Attorney, Agent, or Firm* — Parker Highlander PLLC

(57) ABSTRACT

Solutions, reagents, and methods for nucleic acid purification. In certain aspects, cationic surfactant and, optionally, an anionic surfactant solutions are provided which can be used for phase separation and capture of nucleic acids, such as plasmid or genomic DNA, to a solid phase carrier, such as a mineral matrix.

20 Claims, 26 Drawing Sheets

(56) References Cited

OTHER PUBLICATIONS

Second Declaration of Ryan Kemp under 37 C.F.R. § 1.132, submitted in U.S. Appl. No. 14/619,037, dated Apr. 20, 2018.
Velegraki et al., "Rapid extraction of fungal DNA from clinical samples for PCR amplification," *Medical Mycology*, 37: 69-73, 1999.

\* cited by examiner

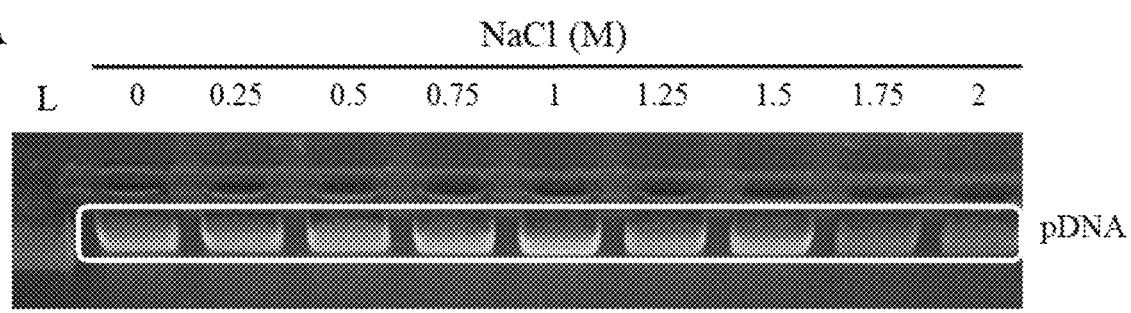
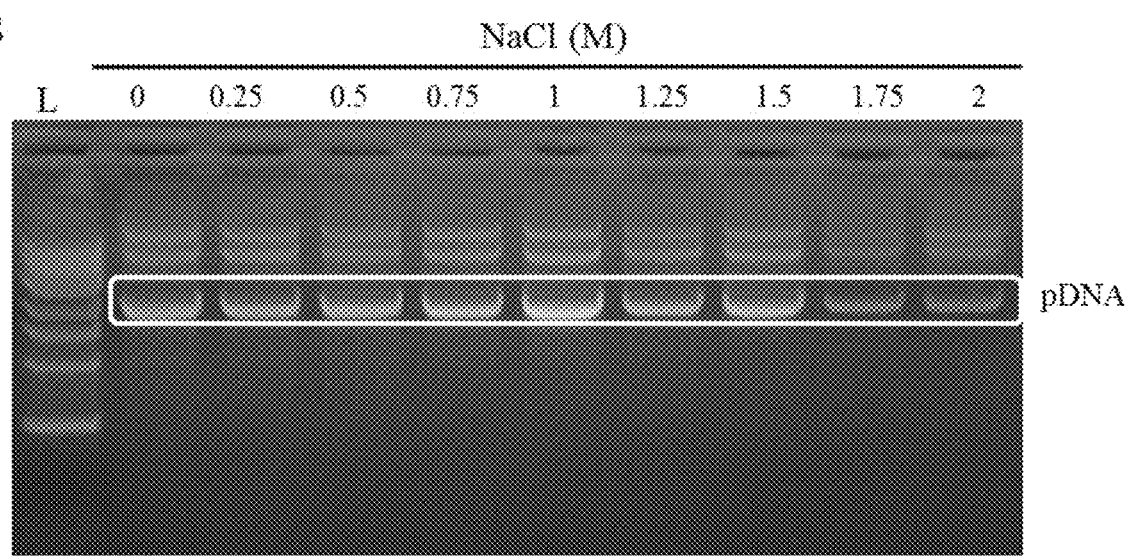
FIGs. 1A-B

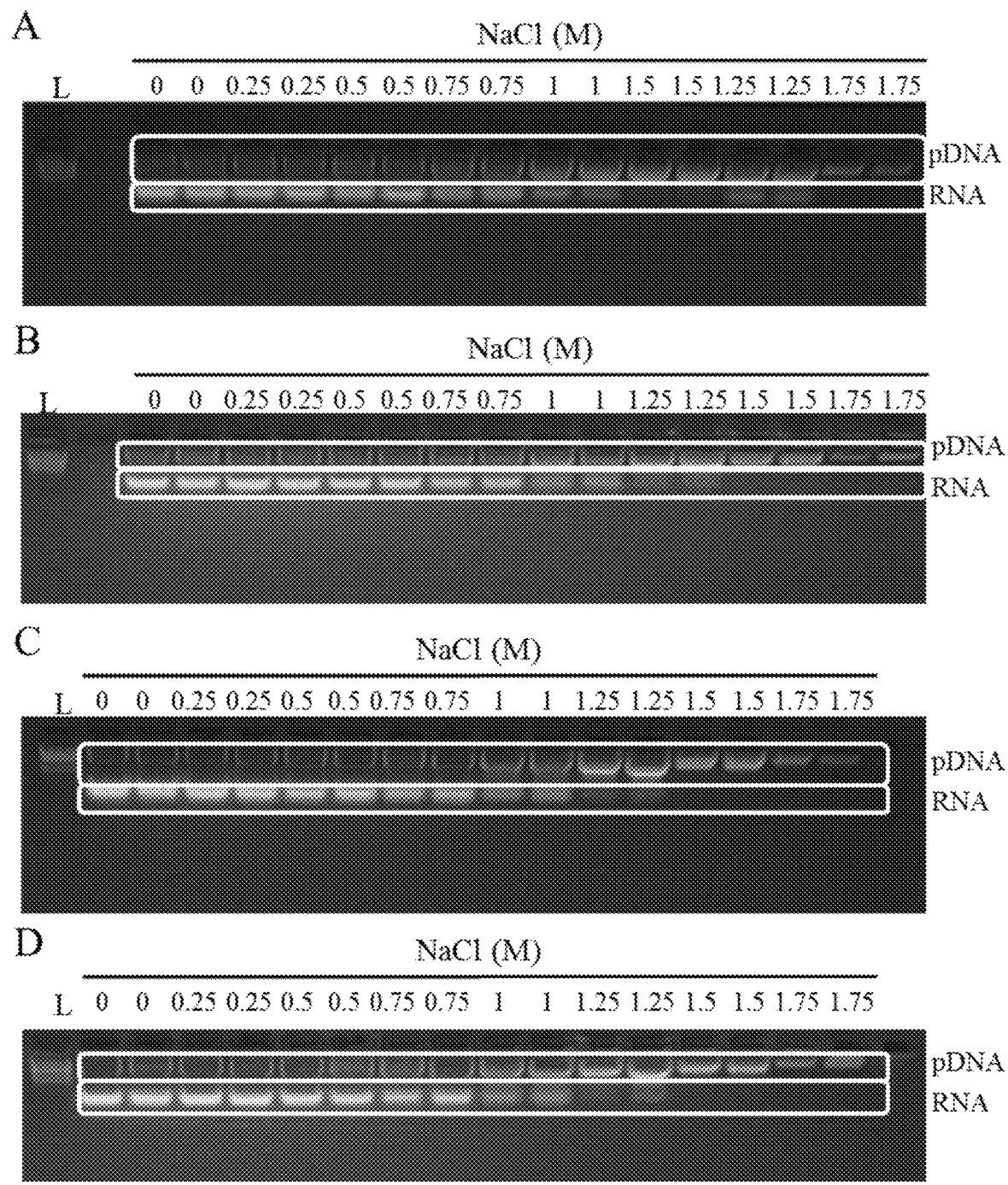
FIGs. 3A-D

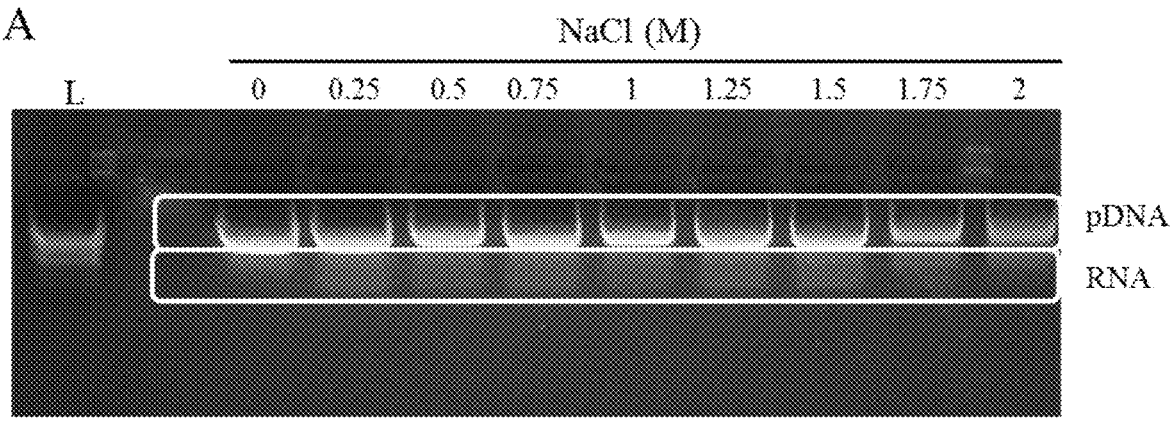
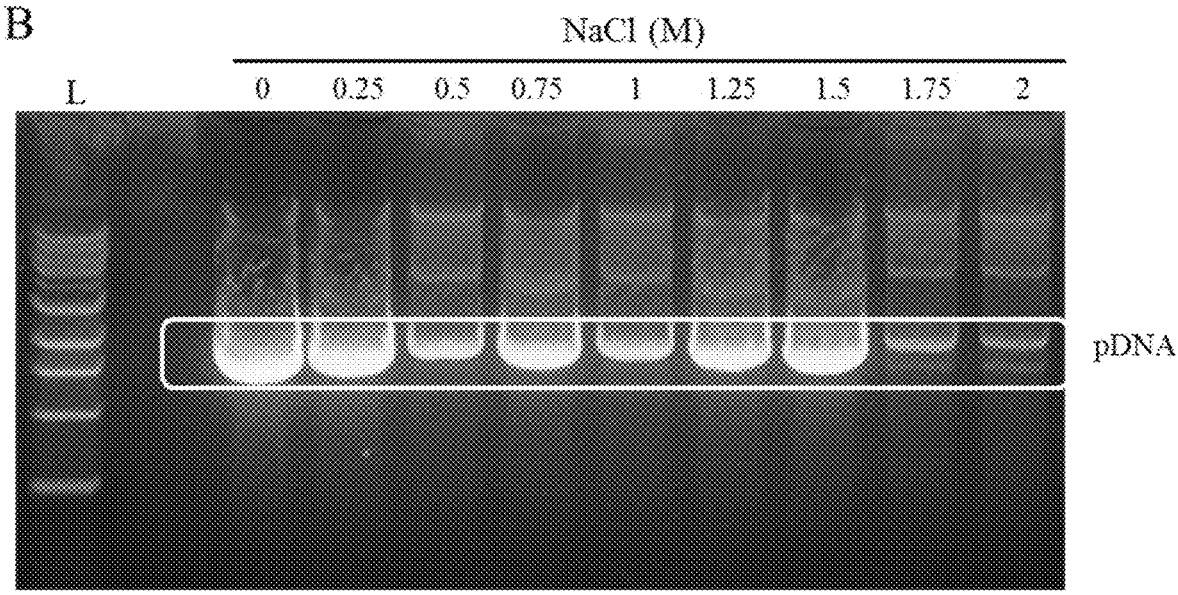
FIGs. 4A-B

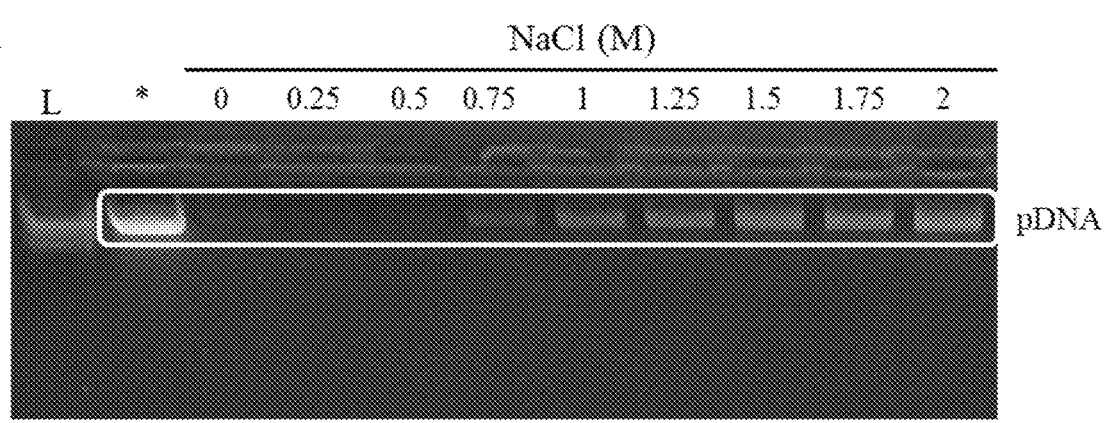
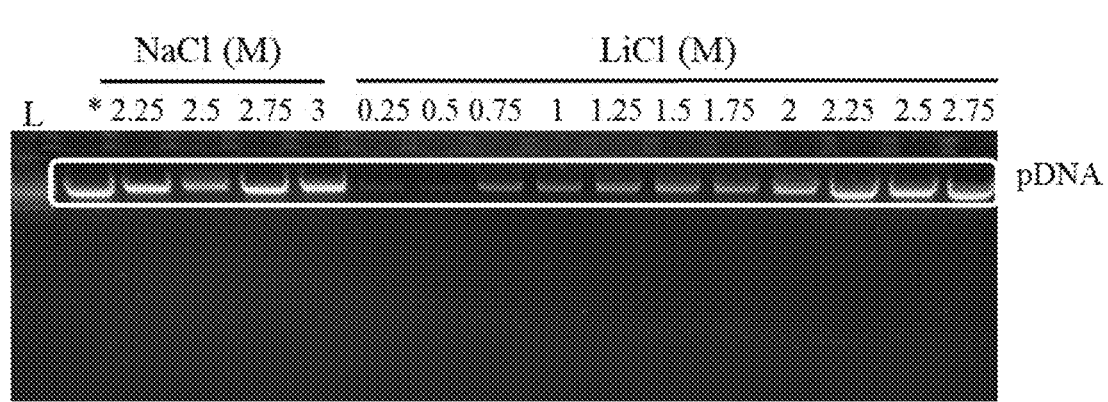
FIGs. 5A-B

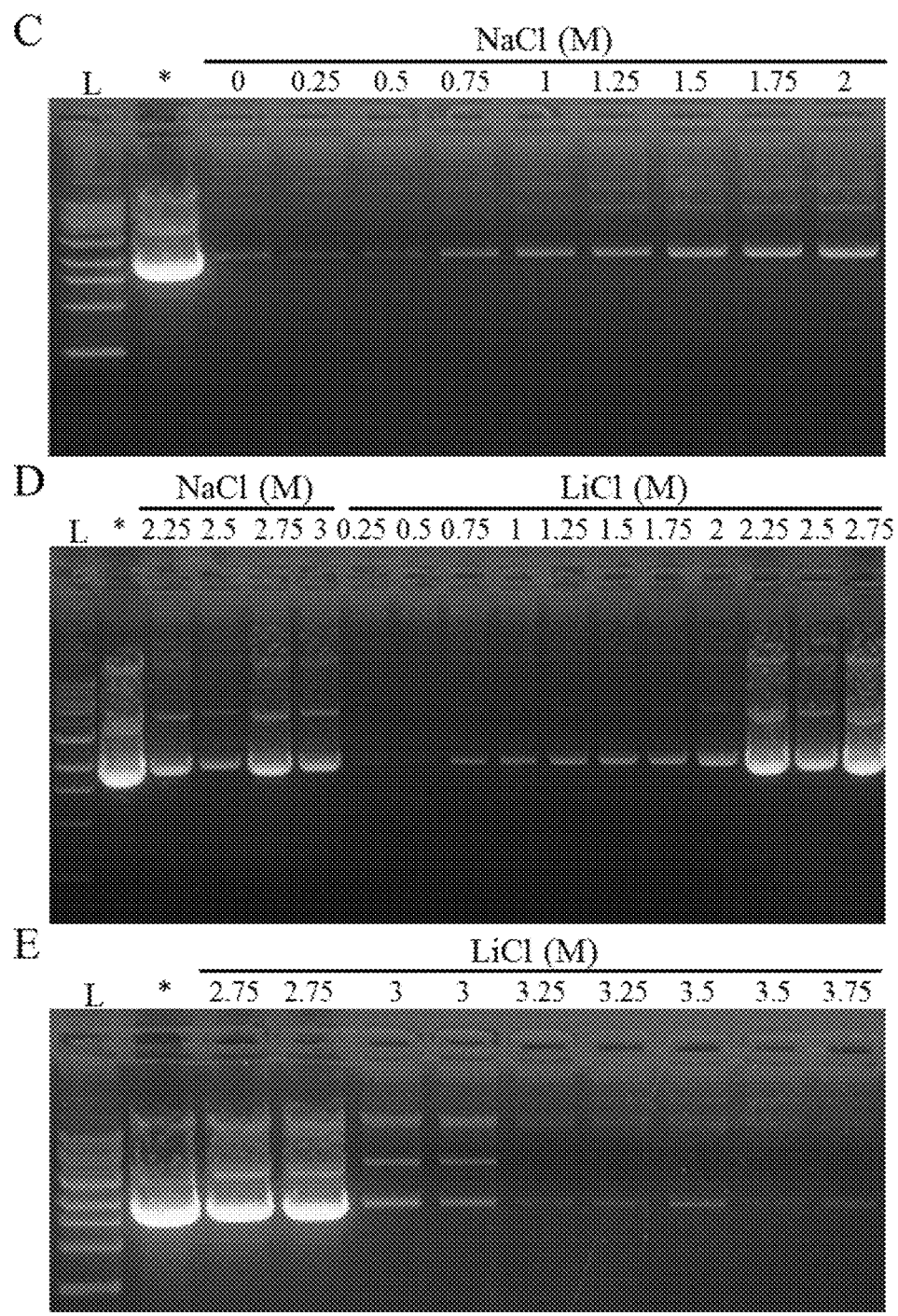
FIGs. 5C-E

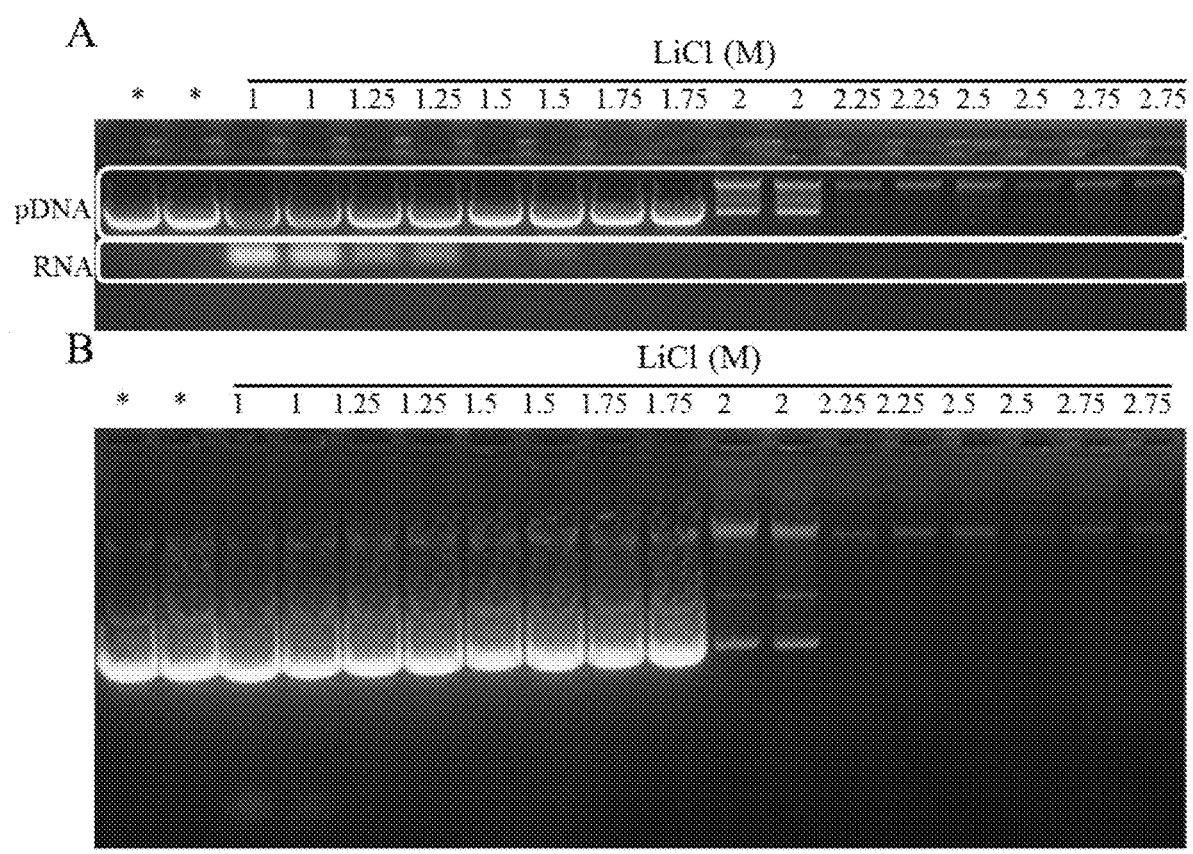
FIGs. 6A-B

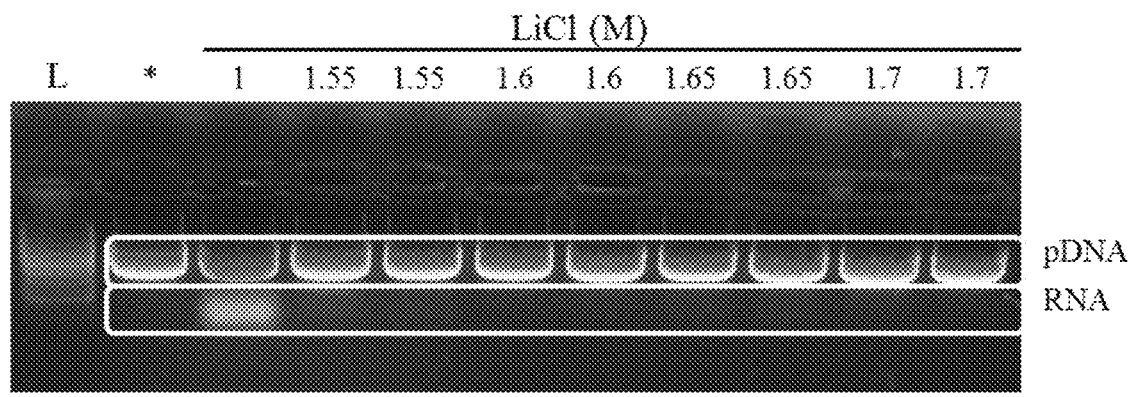
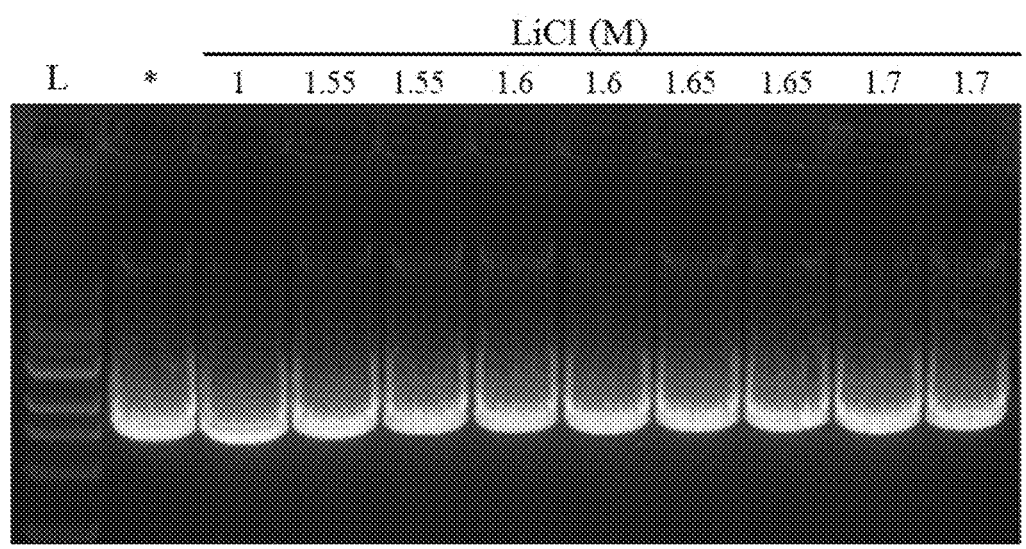
FIGs. 6C-D

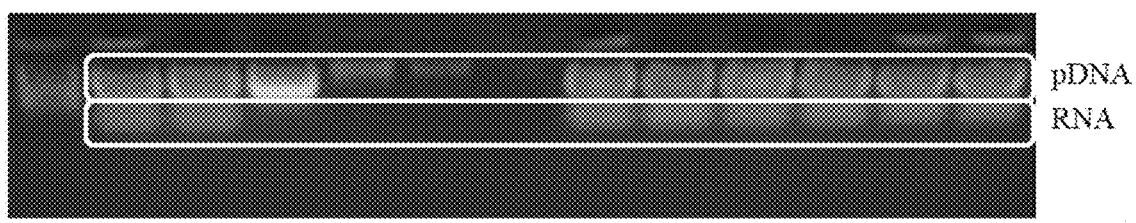
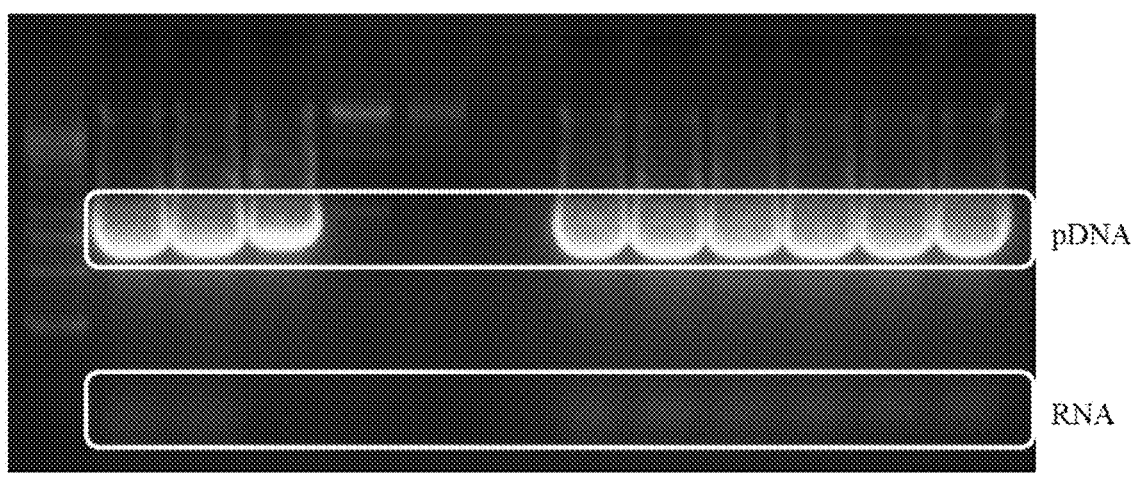
FIGs. 7A-B

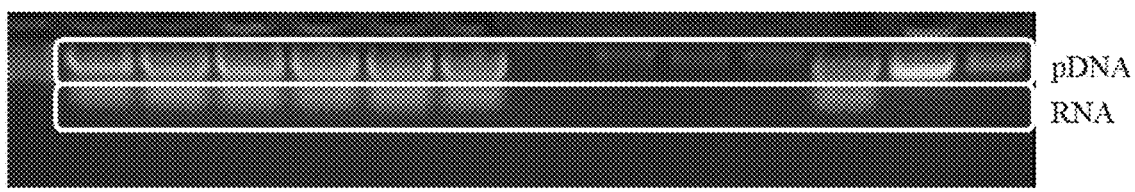
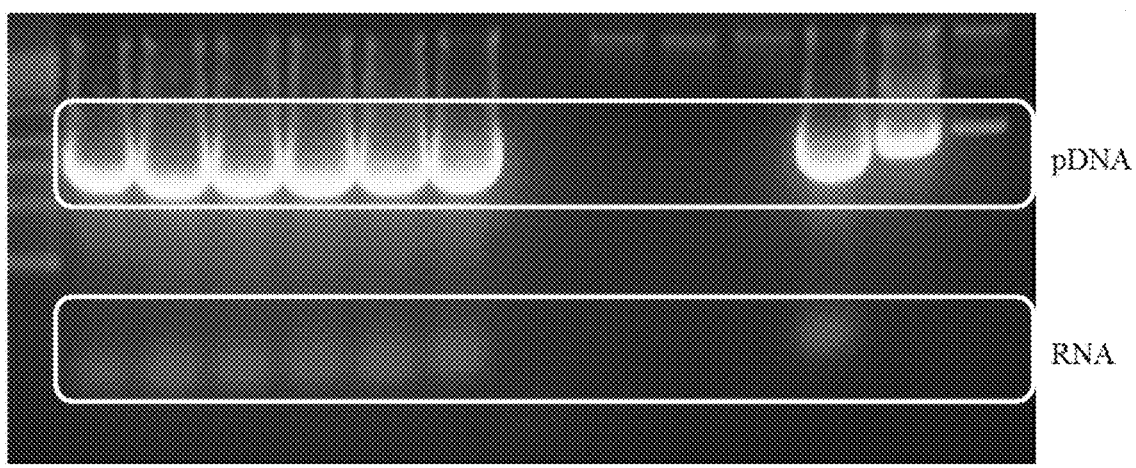
FIGs. 7C-D

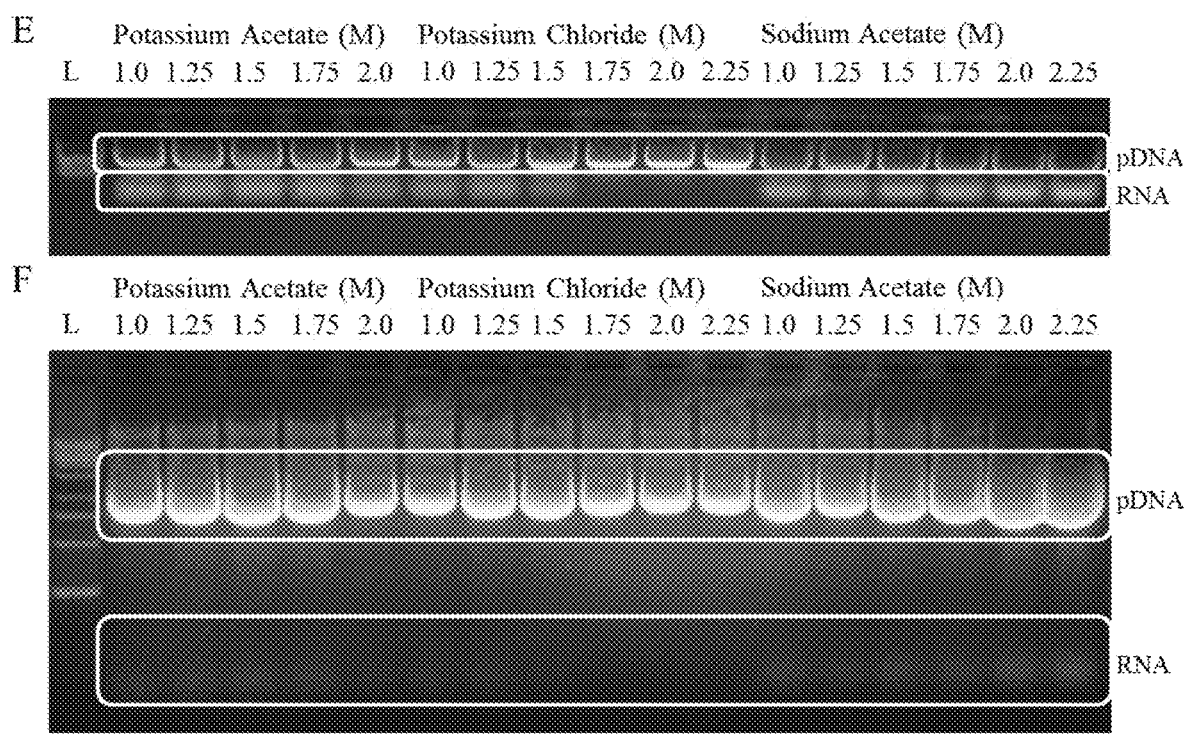
FIGs. 7E-F

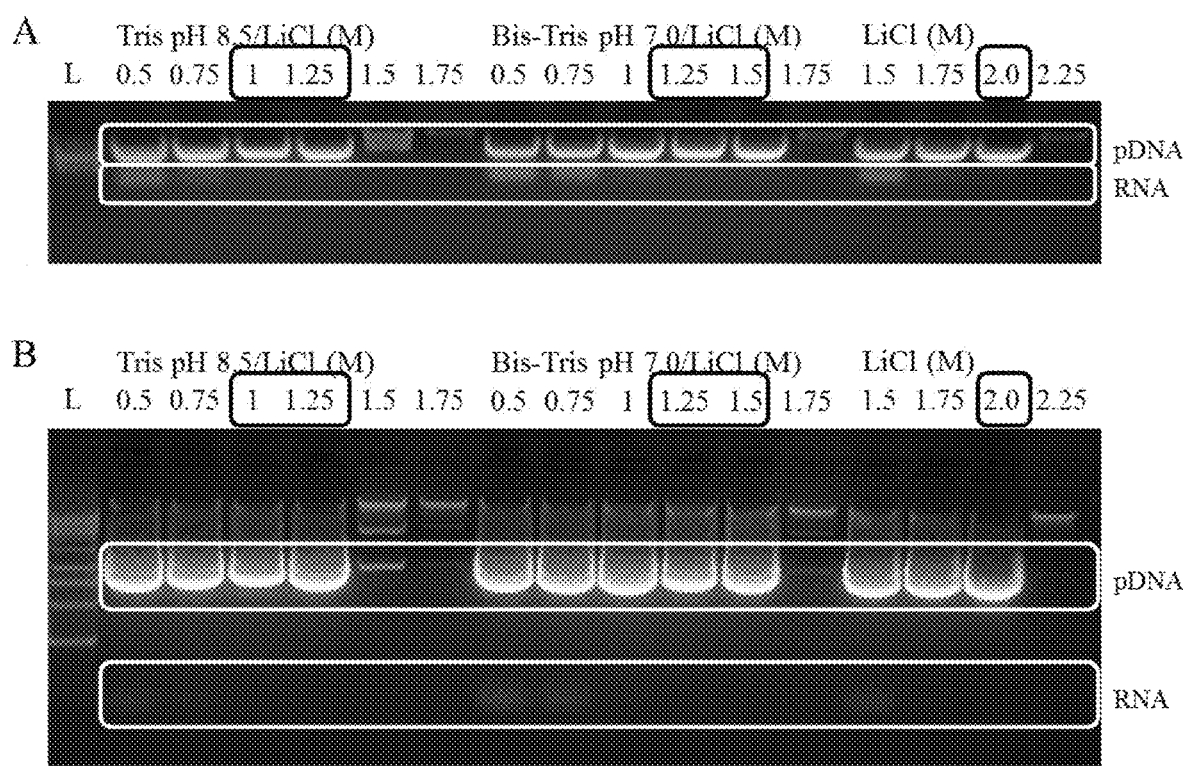
FIGs. 8A-B

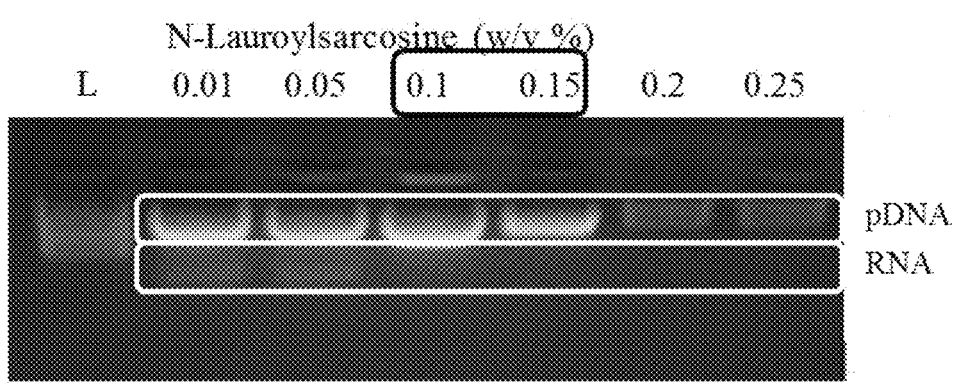
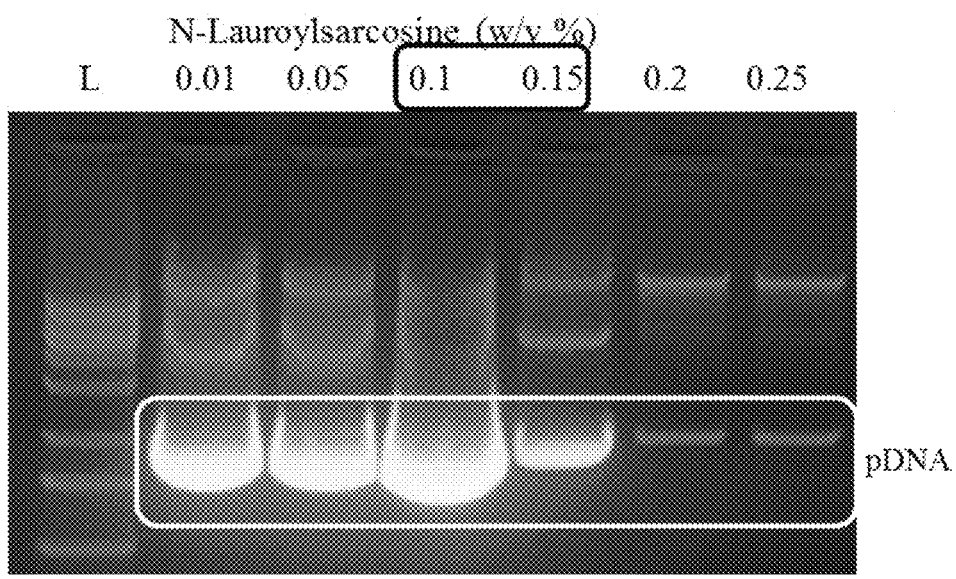
FIGs. 8C-D

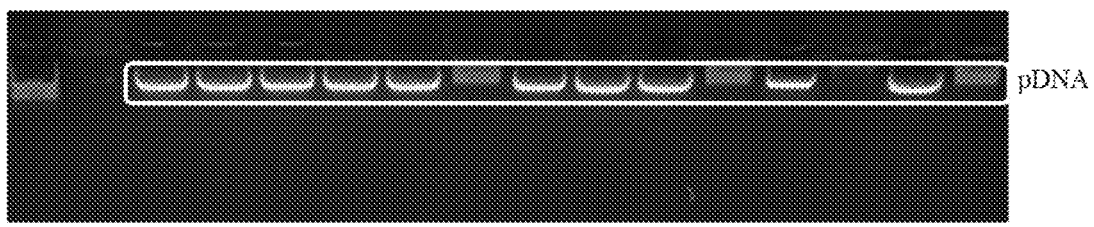
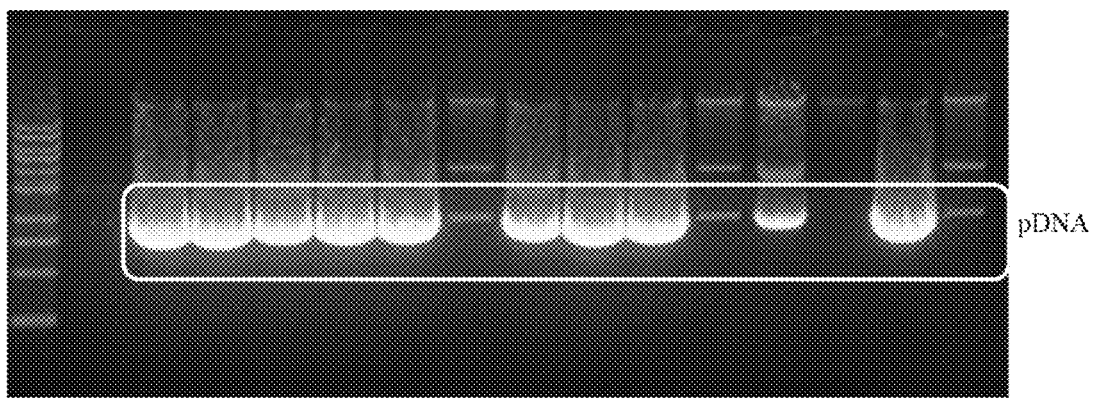
FIGs. 9A-B

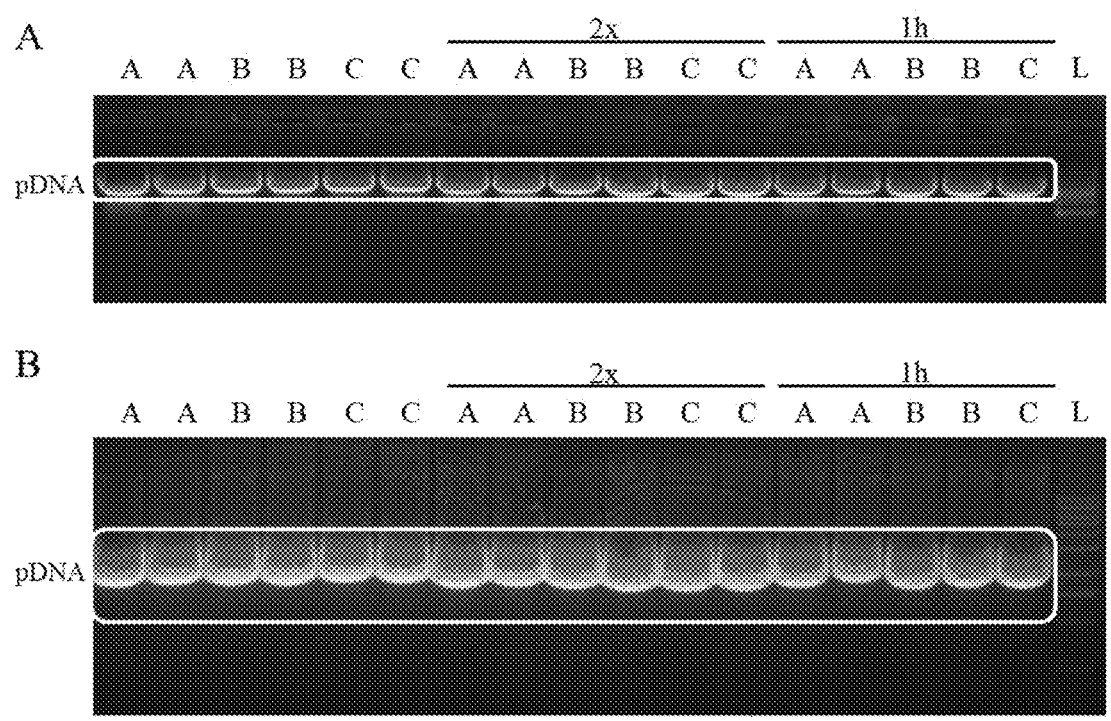
FIGs. 10A-B

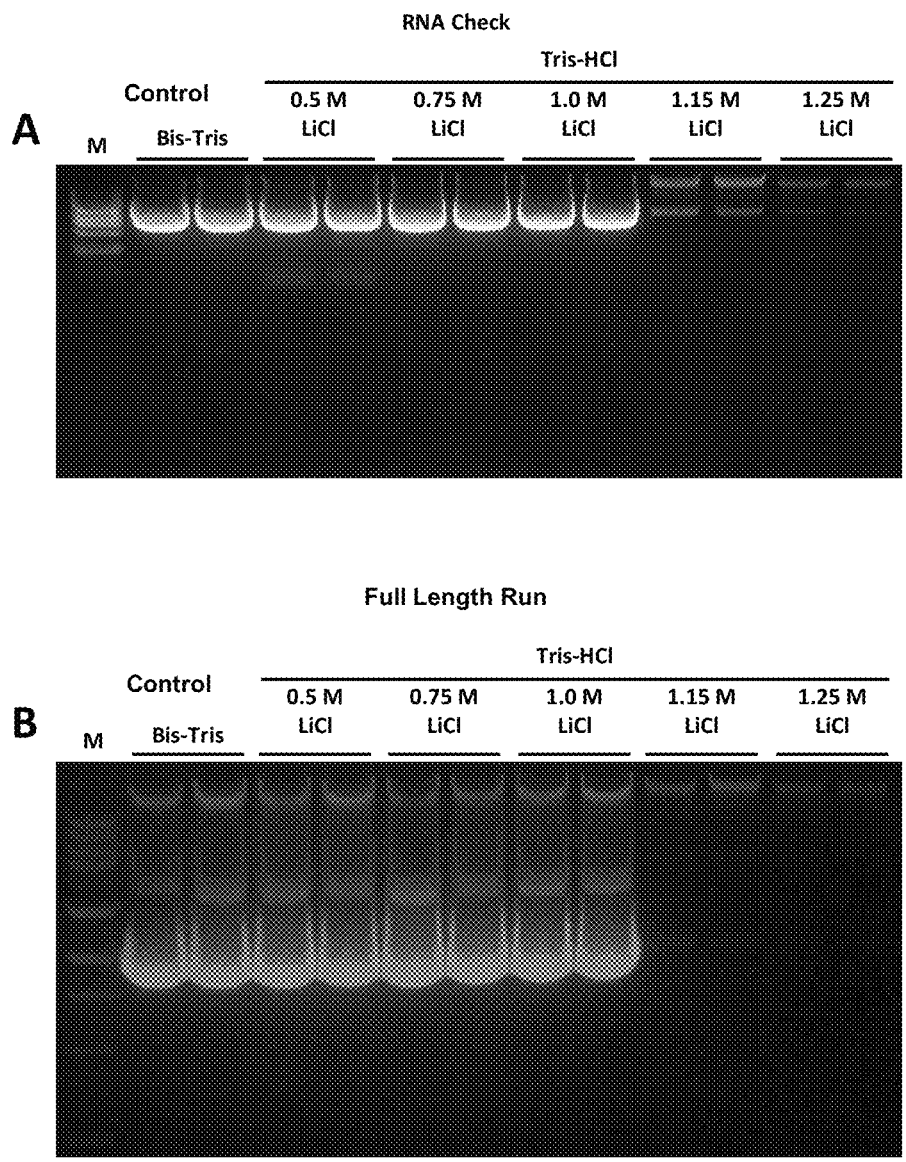
FIGs. 14A-B

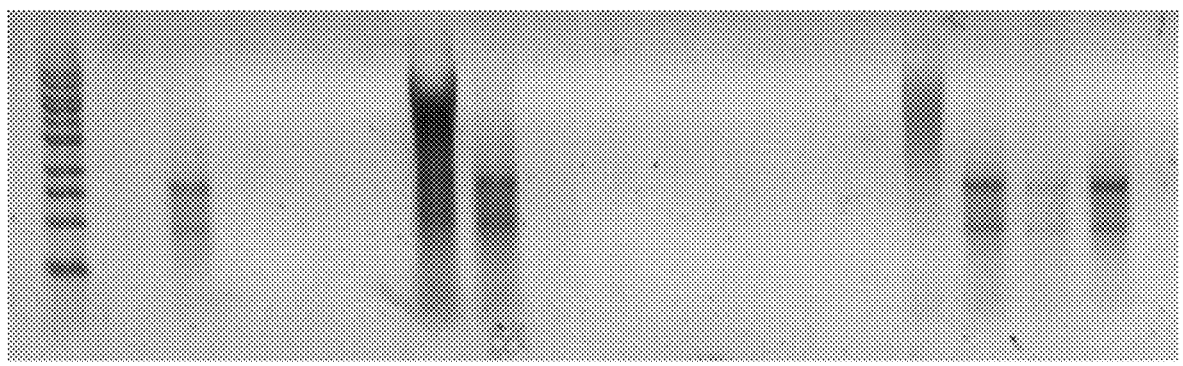
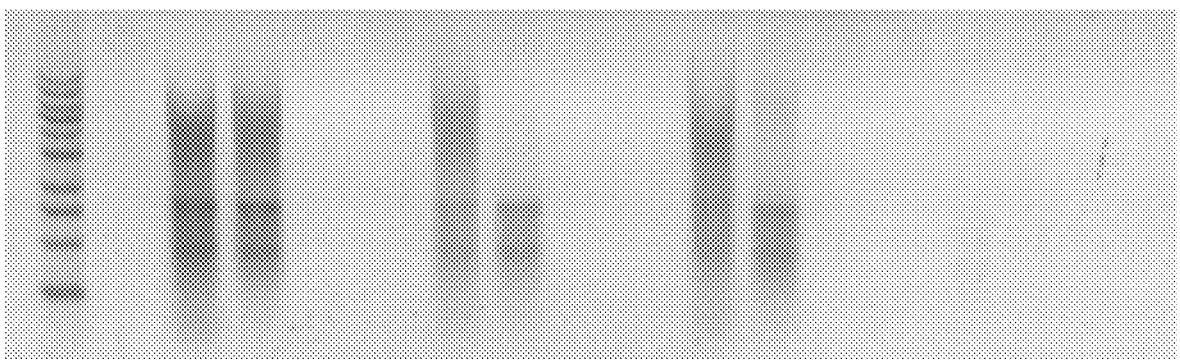
FIGs. 15A-B

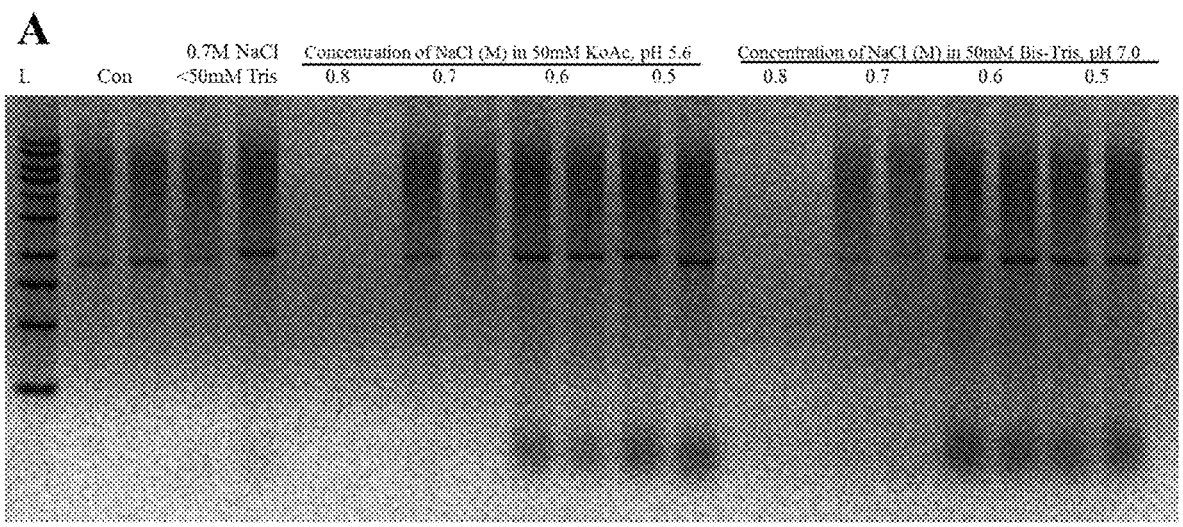
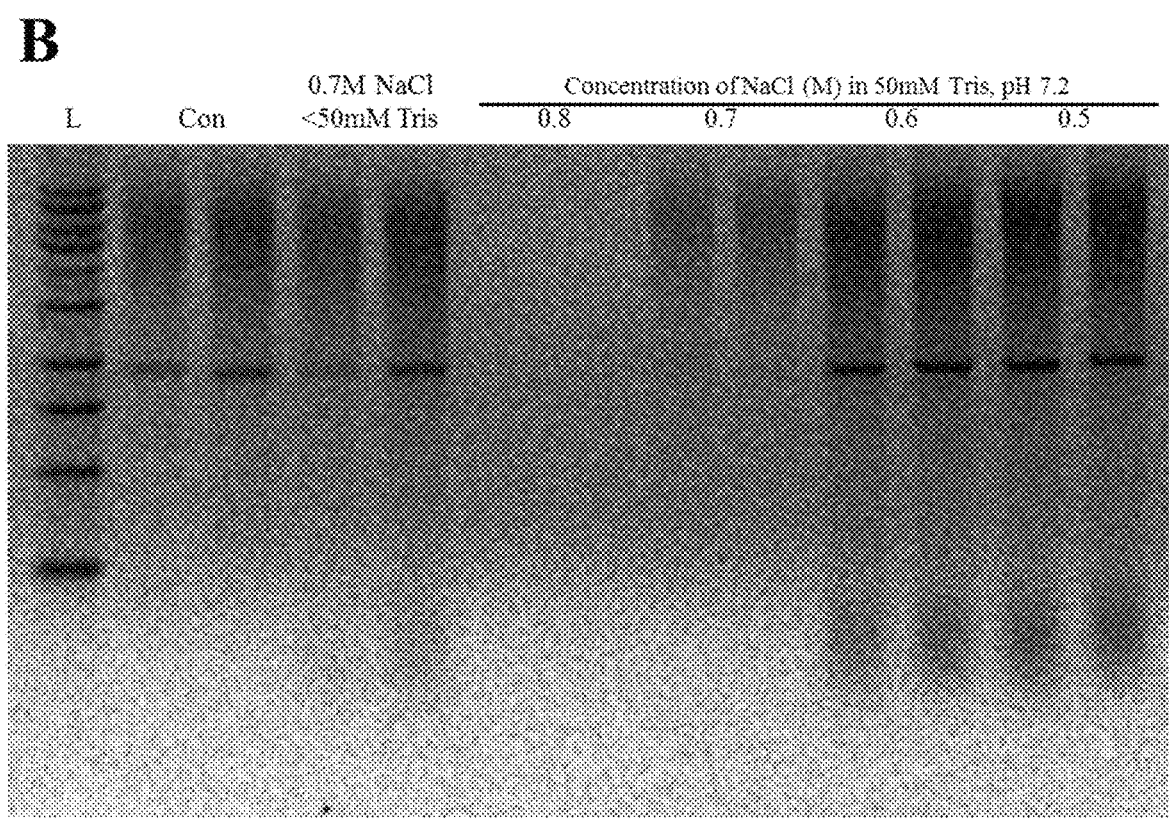
FIGs. 19A-B

METHODS FOR NUCLEIC ACID CAPTURE

This application is a divisional of U.S. patent application Ser. No. 14/619,037, filed Feb. 10, 2015, which claims the benefit of U.S. Provisional Patent Application No. 61/937,824, filed Feb. 10, 2014; 62/013,668, filed Jun. 18, 2014; and 62/079,358, filed Nov. 13, 2014, each of which is incorporated herein by reference, in its entirety.

BACKGROUND OF THE INVENTION

1. Field of the Invention

The present invention relates generally to the field of molecular biology. More particularly, it concerns nucleic acid purification, particularly the isolation of DNA.

2. Description of Related Art

The present invention relates to the purification of nucleic acids from source materials, especially genomic and plasmid DNA. In the case of genomic DNA, modern molecule biological techniques require substantially purified DNA samples and, in some cases it is highly desirable to purify genomic material having a limited amount of retained RNA and/or plasmid DNA. Likewise, in the purification of plasmid DNA from bacterial lysates, plasmid purity is critical for downstream recombinant DNA manipulations. The sensitive reactions commonly employed in molecular biology experiments of reverse transcription, transcription, DNA and RNA sequencing, polymerase chain reaction (PCR), restriction digests, ligation reactions, end modifications, among other similar base modification procedures require the DNA, or other nucleic acid molecules, be essentially free from contaminants. It is also desirable to isolate the nucleic acid in significant quantities to ensure a reliable source of material with which to proceed to additional experiments. In many instances there is a need to move a desired DNA, or fragment thereof, through several manipulations to reach the desired endpoint. Cloning procedures, for example, are often complex and involve numerous steps; therefore, methods that reliably isolate pure DNA, and other nucleic acids, in significant quantities are desired.

Conventional procedures for isolating plasmid DNA, for example, include harvesting the bacterial cells and obtaining the plasmid DNA, or other target nucleic acid, in a pure form via lysis, free from undesirable contaminating medium and cellular constituents. This is typically called a cleared bacterial or cellular lysate. The cell lysis may be performed in a variety of ways including mechanical sonication or blending, enzymatic digestion and also the traditional chemical means of alkaline lysis. The alkaline lysis based protocols remain the basis for many plasmid purification methods, though other procedures, such as the boiling lysis, triton lysis, and polyethylene glycol protocols, are also used (Bimboim and Dolly, 1979; Bimboim, 1983; Holmes and Quigley, 1981; Clewell and Helinski, 1970; Lis and Schleif, 1975).

Approaches that coupled alkaline lysis to cesium chloride gradient centrifugation and organic extraction with toxic and caustic phenol/chloroform and alcohols have largely been replaced by a variety of systems that use rapid and efficient chromatographic methods. The observation that DNA bound preferentially to ground glass or glass fiber disks in the presence of high concentrations of sodium iodide or sodium perchlorate allowed the development of new purification methodologies (Marko et al., 1981; Vogelstein et al., 1979). The use of the chaotropic salt solutions, such as guanidinium, iodide, perchlortate, and trichloroacetate, coupled to forms of silica-based or other chromatographic techniques, has resulted in a preferred methodology for plasmid as well as general nucleic acid purification. Despite these improvements and the development of numerous nucleic acid purification systems there remains a need to develop improved systems to satisfy demands for easier, faster protocols with increased yield and reliability for high-level quantity purification of plasmids and other nucleic acid materials.

SUMMARY OF THE INVENTION

In some embodiments, the present invention provides a fast, reliable, and efficient method for the isolation of substantially purified genomic or plasmid DNA. For example, in some aspects, methods detailed herein are based on an alkaline lysis procedure. In certain aspects, a process is provided that increases the quality and yield of DNA, or other nucleic acid isolated, in a small elution volume.

In certain embodiments, there is provided method for phase separating nucleic acids from a solution and capturing nucleic acids with a mineral matrix for purification comprising (a) contacting a nucleic acid-containing sample (e.g., a sample comprising plasmid DNA) with a phase separation reagent comprising a cationic surfactant of the embodiments and (b) capturing the phase separated nucleic acid with the mineral matrix (e.g., a silica-based matrix, such as borosilicate glass fiber). In some aspects, the method further comprises one or more of the following steps: c) treating the captured nucleic acid with a salt solution (e.g., thereby increasing the retention of nucleic acid); (d) washing the captured nucleic acid with an organic wash solution (e.g., thereby purifying the captured nucleic acid); and/or (e) eluting the captured nucleic acid from the mineral matrix, thereby isolating the nucleic acid. Thus, methods of the embodiments, involve the mixing of a number of reagents as part of the purification protocol. Through-out the application concentrations or various reagent constituents are, in some cases, listed for simplicity as those in the original solution (prior to any mixing). However, concentration of solution components are also provided as "a final concentration" (e.g., in w/v, v/v or M), which as used herein refers to the concentration of the component at the time of nucleic acid capture to a mineral matrix (e.g., just prior to a wash step).

Thus, in one embodiment there is provided a reagent for use in purification of nucleic acids, such as plasmid DNA, the reagent comprising a cationic surfactant of Formula I:

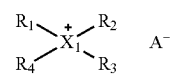

wherein:
$X_1$ is nitrogen, phosphorus, N-heteroaryl$_{(C \leq 18)}$ or substituted N-heteroaryl$_{(C \leq 18)}$, provided that when $X_1$ is N-heteroaryl$_{(C \leq 18)}$ or substituted N-heteroaryl$_{(C \leq 18)}$, then $R_2$, $R_3$, and $R_4$ are absent and when $R_2$, $R_3$, and $R_4$ are absent, then $X_1$ is N-heteroaryl$_{(C \leq 18)}$ or substituted N-heteroaryl$_{(C \leq 18)}$;
$R_1$ is alkyl$_{(C \leq 30)}$, alkenyl$_{(C \leq 30)}$, alkynyl$_{(C \leq 30)}$, aryl$_{(C \leq 30)}$, aralkyl$_{(C \leq 30)}$, heteroaryl$_{(C \leq 30)}$, heteroaralkyl$_{(C \leq 30)}$, a substituted version of any of these groups or —$Y_1$—$Z$—$Y_2$;
$Y_1$ is alkandiyl$_{(C \leq 6)}$, alkendiyl$_{(C \leq 6)}$, alkyndiyl$_{(C \leq 6)}$, arenediyl$_{(C \leq 6)}$, alkoxydiyl$_{(C \leq 6)}$, or a substituted version of any of these groups;

Z is —O—, —NH—, —S—, —C(O)O—, —OC(O)—, —NHC(O)—; or —C(O)NH—;

$Y_2$ is alkyl$_{(C\leq30)}$, alkenyl$_{(C\leq30)}$, alkynyl$_{(C\leq30)}$, aryl$_{(C\leq30)}$, aralkyl$_{(C\leq30)}$, heteroaryl$_{(C\leq30)}$, heteroaralkyl$_{(C\leq30)}$, or a substituted version of any of these groups;

$R_2$, $R_3$, and $R_4$ are each independently alkyl$_{(C\leq30)}$, alkenyl$_{(C\leq30)}$, alkynyl$_{(C\leq30)}$, aryl$_{(C\leq30)}$, aralkyl$_{(C\leq30)}$, heteroaryl$_{(C\leq30)}$, heteroaralkyl$_{(C\leq30)}$, a substituted version of any of these groups or —$Y_3$—Z—$Y_4$;

$Y_3$ is alkandiyl$_{(C\leq6)}$, alkendiyl$_{(C\leq6)}$, alkyndiyl$_{(C\leq6)}$, arenediyl$_{(C\leq6)}$, or a substituted version of any of these groups;

Z is —O—, —NH—, —S—, —C(O)O—, —OC(O)—, —NHC(O)—; or —C(O)NH—;

$Y_4$ is alkyl$_{(C\leq30)}$, alkenyl$_{(C\leq30)}$, alkynyl$_{(C\leq30)}$, aryl$_{(C\leq30)}$, aralkyl$_{(C\leq30)}$, heteroaryl$_{(C\leq30)}$, heteroaralkyl$_{(C\leq30)}$, or a substituted version of any of these groups; and A is bromide, chloride, iodide, phosphate, sulfate, acetate, formate, propionate, oxalate, or succinate, provided that when $R_2$, $R_3$ and $R_4$ are alkyl$_{(C\leq30)}$, alkenyl$_{(C\leq30)}$, alkynyl$_{(C\leq30)}$, aryl$_{(C\leq30)}$, aralkyl$_{(C\leq30)}$, heteroaryl$_{(C\leq30)}$, heteroaralkyl$_{(C\leq30)}$, or a halo substituted version of any of these groups and $X_1$ is nitrogen or phosphorus, then $R_1$ is —$Y_1$—Z—$Y_2$. For example, in some aspects, a phase separation reagent of the embodiments comprises about 0.1% to about 10% of a cationic surfactant of Formula I (e.g., 0.15% to about 10.0%, 0.15% to about 5.0%, 0.5% to about 2.0%, or 0.8% to about 1.2%). Thus, in some aspects, a cationic surfactant of Formula I is present in a final concentration (w/v) of 0.025% to about 2.5% (e.g., 0.0375% to about 2.5.0%, 0.0375% to about 1.25%, 0.125% to about 0.5%, or 0.2% to about 0.3%). In still further aspects, a phase separation reagent comprises a salt selected from the group consisting of NaCl, NaoAc, KCl, KoAc, LiCl, LioAc, sodium formate, potassium formate, lithium formate, calcium chloride, magnesium chloride and a mixture thereof. In yet further aspects, a phase separation reagent further comprises a pH buffering reagent, such as a Tris or Bis-Tris or KoAc. Thus, in some aspects, a phase separation reagent comprises a pH between about 3.5 and about 9.0, between about 5.0 and 8.0, between about 6.0 and 8.0; between about 6.5 and 7.5 or between about 6.7 and 7.3 (e.g., between 6.8 and 7.3).

In some aspects, a surfactant of Formula I is further defined as:

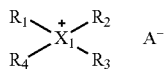

wherein: $X_1$ is nitrogen or phosphorus; $R_1$ is —$Y_1$—Z—$Y_2$; $Y_1$ is alkandiyl$_{(C\leq6)}$, alkendiyl$_{(C\leq6)}$, alkyndiyl$_{(C\leq6)}$, arenediyl$_{(C\leq6)}$, alkoxydiyl$_{(C\leq6)}$, or a substituted version of any of these groups; Z is —O—, —NH—, —S—, —C(O)O—, —OC(O)—, —NHC(O)—; or —C(O)NH—; $Y_2$ is alkyl$_{(C\leq30)}$, alkenyl$_{(C\leq30)}$, alkynyl$_{(C\leq30)}$, aryl$_{(C\leq30)}$, aralkyl$_{(C\leq30)}$, heteroaryl$_{(C\leq30)}$, heteroaralkyl$_{(C\leq30)}$, or a substituted version of any of these groups; $R_2$, $R_3$, and $R_4$ are each independently alkyl$_{(C\leq30)}$, alkenyl$_{(C\leq30)}$, alkynyl$_{(C\leq30)}$, aryl$_{(C\leq30)}$, aralkyl$_{(C\leq30)}$, heteroaryl$_{(C\leq30)}$, heteroaralkyl$_{(C\leq30)}$, a substituted version of any of these groups or —$Y_3$—Z—$Y_4$; $Y_3$ is alkandiyl$_{(C\leq6)}$, alkendiyl$_{(C\leq6)}$, alkyndiyl$_{(C\leq6)}$, arenediyl$_{(C\leq6)}$, or a substituted version of any of these groups; Z is —O—, —NH—, —S—, —C(O)O—, —OC(O)—, —NHC(O)—; or —C(O)NH—; $Y_4$ is alkyl$_{(C\leq30)}$, alkenyl$_{(C\leq30)}$, alkynyl$_{(C\leq30)}$, aryl$_{(C\leq30)}$, aralkyl$_{(C\leq30)}$, heteroaryl$_{(C\leq30)}$, heteroaralkyl$_{(C\leq30)}$, or a substituted version of any of these groups; and A is bromide, chloride, iodide, phosphate, sulfate, acetate, formate, propionate, oxalate, or succinate. In still further aspects, a cationic surfactant of Formula I is defined as:

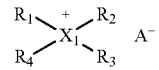

wherein: $X_1$ is nitrogen or phosphorus; $R_1$ is —$Y_1$—Z—$Y_2$; $Y_1$ is alkandiyl$_{(C\leq6)}$ or substituted alkandiyl$_{(C\leq6)}$; Z is —O—; $Y_2$ is alkyl$_{(C\leq30)}$, aryl$_{(C\leq30)}$, aralkyl$_{(C\leq30)}$, or a substituted version of any of these groups; $R_2$, $R_3$, and $R_4$ are each independently alkyl$_{(C\leq30)}$ or substituted alkyl$_{(C\leq30)}$; and A is bromide, chloride, iodide, phosphate, sulfate, acetate, formate, propionate, oxalate, or succinate. In still further aspects, a cationic surfactant of Formula I is defined as:

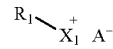

wherein $X_1$ is N-heteroaryl$_{(C\leq18)}$ or substituted N-heteroaryl$_{(C\leq18)}$; $R_1$ is alkyl$_{(C\leq30)}$, alkenyl$_{(C\leq30)}$, alkynyl$_{(C\leq30)}$, aryl$_{(C\leq30)}$, aralkyl$_{(C\leq30)}$, heteroaryl$_{(C\leq30)}$, heteroaralkyl$_{(C\leq30)}$, a substituted version of any of these groups or —$Y_1$—Z—$Y_2$; $Y_1$ is alkandiyl$_{(C\leq6)}$, alkendiyl$_{(C\leq6)}$, alkyndiyl$_{(C\leq6)}$, arenediyl$_{(C\leq6)}$, or a substituted version of any of these groups; Z is —O—, —NH—, —S—, —C(O)O—, —OC(O)—, —NHC(O)—; or —C(O)NH—; $Y_2$ is alkyl$_{(C\leq30)}$, alkenyl$_{(C\leq30)}$, alkynyl$_{(C\leq30)}$, aryl$_{(C\leq30)}$, aralkyl$_{(C\leq30)}$, heteroaryl$_{(C\leq30)}$, heteroaralkyl$_{(C\leq30)}$, or a substituted version of any of these groups; and A is bromide, chloride, iodide, phosphate, sulfate, acetate, formate, propionate, oxalate, or succinate.

Thus, in some aspects, a cationic surfactant according to Formula I comprises wherein a position A, which is bromide or chloride; $R_1$ is —$Y_1$—Z—$Y_2$; $R_2$ which is alkyl$_{(C\leq30)}$ (e.g., methyl); $R_3$ which is alkyl$_{(C\leq30)}$ (e.g., methyl); and/or $R_4$ which is alkyl$_{(C\leq30)}$ (e.g., methyl). In certain aspects, $R_1$ is alkyl$_{(C\leq30)}$, alkyl$_{(C\leq20)}$, alkyl$_{(C\leq10)}$, alkyl$_{(C\leq4)}$, decane, hexadecane, aryl$_{(C\leq30)}$, aryl$_{(C\leq20)}$, aryl$_{(C\leq10)}$, benzyl, ethyl or methyl. In still further aspects, $R_2$ is alkyl$_{(C\leq20)}$, alkyl$_{(C\leq10)}$, alkyl$_{(C\leq4)}$, ethyl or methyl. In yet further aspects, $R_3$ is methyl, ethyl, benzyl, aralkyl$_{(C\leq30)}$, alkyl$_{(C\leq20)}$, alkyl$_{(C\leq10)}$, alkyl$_{(C\leq4)}$ or dodecane. In yet still further aspects, $R_4$ is alkyl$_{(C\leq20)}$, alkyl$_{(C\leq10)}$, alkyl$_{(C\leq4)}$, ethyl or methyl. In still further aspects, $X_1$ is pyridinium, 4-carbamoylpyridinium, 1-decylimidazolium, 1-decyl-2-methyl-imidazolium, N-heteroaryl$_{(C\leq18)}$ or substituted N-heteroaryl$_{(C\leq18)}$.

In some further aspects, the $R_1$ position of a cationic surfactant of Formula I is —$Y_1$—Z—$Y_2$, and $Y_1$ is alkandiyl$_{(C\leq6)}$ (e.g., —CH$_2$CH$_2$— or —CH$_2$—), alkoxydiyl$_{(C\leq6)}$ (e.g., —CH$_2$CH$_2$OCH$_2$CH$_2$— or —CH$_2$OCH$_2$—); Z is —O—, —OC(O)— or —NHC(O)—; and $Y_2$ is aryl$_{(C\leq30)}$, aryl$_{(C\leq20)}$, aryl$_{(C\leq10)}$, phenyl, (2,4,4-trimethylpentan-2-yl)-benzene, dodecane, 9-decene or tridecane.

Thus, in some specific embodiments a cationic surfactant of Formula I is defined as:

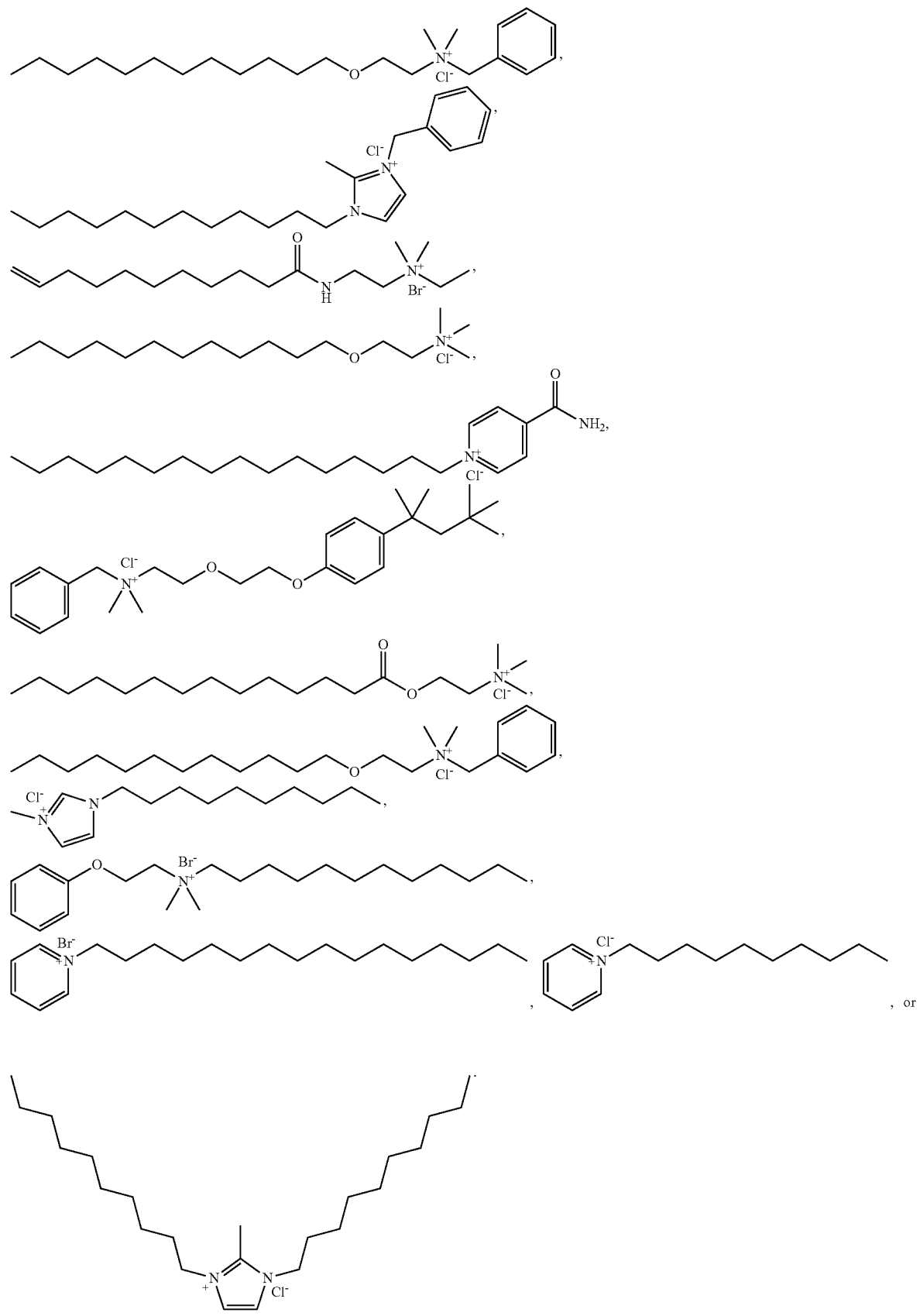

In certain very specific embodiments the cationic surfactant is domiphen bromide ((Dodecyldimethyl-2-phenoxyethyl)ammonium bromide); DB), myristoylcholine chloride, benzyldimethyl(2-dodecyloxyethyl)-ammonium chloride, benzethonium chloride, cetylpyridinium chloride, dodecylpyridinium chloride, 1-decyl-3-methylimidazolium chloride, 1,3-didecyl-2-methylimidazolium chloride, lauryl choline chloride, 1-dodecyl-2-methyl-3-benzimidazolium chloride, 4-carboyl-1-N-hexadecyl pyridinium chloride, N-ethyl-N,N-dimethyl-2-(10-undecenoylamino) ethanaminium bromide, or benzethonium chloride.

In further embodiment there is provided a nucleic acid binding mixture comprising: (a) an aqueous solution comprising (i) 0.5-20% of a phase separating agent of formula I and (ii) 0.05 M to 1.0 M salt, such as a lithium salt, sodium salt, potassium salt, magnesium salt, or calcium salt, and combinations thereof (e.g., LiCl or NaCl); (b) a mineral matrix of the embodiments; and (c) at least a first nucleic acid molecule (e.g., DNA). In some aspects, the binding mixture comprises 0.5-20% or 1-10% DB. In further aspects, the binding mixture comprises 0.05 M to 1.0 M LiCl, and optionally comprises KOAc. In certain aspects, the binding mixture comprises 0.5 M to 1.0 M NaCl, and optionally comprises KOAc. Thus, in a preferred embodiment, a binding mixture comprises (a) an aqueous solution comprising (i) 0.5-5% DB and (ii) 0.05 M to 1.0 M LiCl; (b) a mineral matrix of the embodiments; and (c) at least a first plasmid DNA molecule. In yet a further preferred embodiment, a binding mixture comprises (a) an aqueous solution comprising (i) 1-10% DB and (ii) 0.5 M to 1.0 M NaCl; (b) a mineral matrix of the embodiments; and (c) at least a genomic DNA molecule.

In yet a further embodiment there is provided a method of isolating DNA, comprising (a) obtaining a sample comprising DNA; (b) capturing the DNA to a mineral matrix with a phase separation solution comprising domiphen bromide (DB) and a salt (e.g., a lithium salt, sodium salt, potassium salt, magnesium salt, calcium salt or a mixtures thereof); (c) washing the mineral matrix and captured DNA with a wash solution; and (d) eluting the plasmid DNA, thereby isolating the DNA. For example, a sample for use according to the embodiments can be a cell lysate, such as a mammalian or bacterial cell lysate. Optionally, a method comprises treating the captured DNA with a salt solution (after the capturing), thereby increasing the retention of the captured DNA. For example, the salt solution can comprise a lithium salt, sodium salt, potassium salt, magnesium salt, calcium salt or a mixtures thereof. In some aspects, (b) capturing DNA to a mineral matrix is in the presence of 0.05% to 1% DB. In further aspects, the wash solution can be an organic was solution (e.g., a solution comprising phenol) or a solution comprising an alcohol (e.g., Ethanol (EtOH) and/or isopropanol). For example, a wash solution of the embodiments may comprise at least about 75%, 80%, 85%, 90% or 95% alcohol, such as a lower alcohol (e.g., EtOH). In certain preferred aspects, an isolated DNA produced by the methods of the embodiments is essentially free of RNA, endotoxin and/or PCR inhibitors. In further aspects, a mineral matrix for use herein is comprised in column, such a spin column adapted for use in centrifuge or microcentrifuge. In further aspects, obtaining a sample comprising DNA comprises obtaining a bacterial cell lysate by alkaline lysis. For example, such a method can comprise (i) lysing cells comprising nucleic acid including DNA with a basic solution thereby generating a lysate; (ii) neutralizing the lysate with an acidic solution thereby precipitating a genomic DNA fraction and proteins; and (iii) clearing the precipitate. In certain aspects, capturing plasmid DNA to a mineral matrix with a phase separation solution (b) and clearing the precipitate (iii) are performed concurrently (or essentially simultaneously).

In certain aspects, a method of the embodiments is defined as a method of selectively isolating genomic DNA. For example, in some aspects, such a method comprises (a) obtaining a sample comprising genomic DNA; (b) capturing the genomic DNA to a mineral matrix with a phase separation solution comprising domiphen bromide (DB) and a salt (e.g., a lithium salt, sodium salt, potassium salt, magnesium salt, calcium salt or a mixtures thereof); (c) washing the mineral matrix and captured genomic DNA with a wash solution; and (d) eluting the genomic DNA, thereby isolating the genomic DNA. Optionally, a method comprises treating the captured DNA with a salt solution (after the capturing), thereby increasing the retention of the captured DNA. For example, the salt solution can comprise a lithium salt, sodium salt, potassium salt, magnesium salt, calcium salt or a mixture thereof. In some cases, selectively isolating genomic DNA, comprises capturing the genomic DNA to a mineral matrix in the presence of DB and a sodium salt, such as sodium chloride. For example, in some cases, capturing the genomic DNA to a mineral matrix is in the presence of 0.05% to 1% DB and 0.5 M to 1.0 M NaCl. In further aspects, the capturing the genomic DNA to a mineral matrix is in the presence of DB, NaCl and KOAc. In still further aspects, the isolated genomic DNA is essentially free of plasmid DNA and/or RNA.

In yet further aspects, a method of the embodiments is defined as a method of selectively isolating plasmid DNA. For example, in some aspects, such a method comprises (a) obtaining a sample comprising plasmid DNA; (b) capturing the plasmid DNA to a mineral matrix with a phase separation solution comprising domiphen bromide (DB) and a salt (e.g., a lithium salt, sodium salt, potassium salt, magnesium salt, calcium salt or a mixtures thereof); (c) washing the mineral matrix and captured plasmid DNA with a wash solution; and (d) eluting the plasmid DNA, thereby isolating the plasmid DNA. Optionally, a method comprises treating the captured DNA with a salt solution (after the capturing), thereby increasing the retention of the captured DNA. For example, the salt solution can comprise a lithium salt, sodium salt, potassium salt, magnesium salt, calcium salt or a mixtures thereof. In some cases, selectively isolating plasmid DNA, comprises capturing the plasmid DNA to a mineral matrix in the presence of DB and a lithium salt, such as lithium chloride. For example, in some aspects, capturing the plasmid DNA to a mineral matrix is in the presence of 0.05% to 1% DB and 0.05 M to 1.0 M LiCl. In further aspects, the capturing the genomic DNA to a mineral matrix is in the presence of DB, LiCl and KOAc. In still further aspects, the isolated plasmid DNA is essentially free of genomic DNA and/or RNA.

In still a further embodiment, there is provided method for selectively condensing plasmid DNA and capturing the DNA to a mineral matrix for purification comprising (a) contacting a plasmid-containing sample (e.g., a bacterial lysate) with a phase separation reagent comprising a cationic surfactant of Formula I (e.g., DB) and (b) capturing the phase separated nucleic acid to the mineral matrix (e.g., a silica-based matrix, such as borosilicate glass fiber) in the presence of an effective amount of a salt selected from the group consisting of NaCl, NaoAc, KCl, KoAc, LiCl, LioAc, sodium formate, potassium formate, lithium formate, calcium chloride, and magnesium chloride, thereby selectively capturing plasmid DNA with the mineral matrix. For example, in some aspects, the salt solution comprises a lithium salt, e.g., LiCl present at a desired final concentration. In certain aspects, capturing the nucleic acid with the mineral matrix is in the presence of a final concentration (M) of about 0.025M-0.5M, about 0.125M-0.5M, about 0.15 M-0.375 M, about 0.25 M-0.375 M, about 0.3 M-0.4 M, about 0.2 M-0.4 M, or about 0.375 M-0.5 M LiCl and a final concentration (w/v) of about 0.05% to 5% or 10%, e.g., 0.05-1%, about 0.1-0.8%, about 0.2-0.5%, about 0.1-0.25%, about 0.2-0.3%, about 0.25-0.3%, about 0.25%-0.4%, about 0.25-0.5% of the cationic surfactant (e.g., DB). In certain preferred aspects, capturing the nucleic acid on mineral matrix is in the presence of a final concentration of LiCl of between about 0.05 M and 1.05 M; about 0.1 M and 0.65 M or about 0.1 M and 0.5 M. For example, in some aspects, the salt solution comprises a sodium salt, e.g., NaCl present at a desired final concentration. In certain aspects, capturing the nucleic acid with the mineral matrix is in the presence of a final concentration (M) of about 0.025M-0.5M, about 0.125M-0.5M, about 0.15 M-0.375 M, about 0.2 M-0.4 M, or about 0.375 M-0.5 M LiCl and a final concentration (w/v) of about 0.05-1%, about 0.1-0.8%, about 0.2-0.5%, about 0.1-0.25%, about 0.2-0.3%, about 0.25-0.3%, about 0.25%-0.4%, about 0.25-0.5% of the cationic surfactant (e.g., DB). In certain preferred aspects, capturing the nucleic acid on mineral matrix is in the presence of a final concentration of NaCl of between about 0.05 M and 1.05 M; about 0.1 M and 0.65 M or about 0.1 M and 0.5 M. For example, in some aspects, the salt solution comprises a potassium salt, e.g., KoAc present at a desired final concentration. In certain aspects, capturing the nucleic acid with the mineral matrix is in the presence of a final concentration (M) of about 0.025M-0.5M, about 0.125M-0.5M, about 0.15 M-0.375 M, about 0.2 M-0.4 M, or about 0.375 M-0.5 M KoAc and a final concentration (w/v) of about 0.05-1%, about 0.1-0.8%, about 0.2-0.5%, about 0.1-0.25%, about 0.2-0.3%, about 0.25-0.3%, about 0.25%-0.4%, about 0.25-0.5% of the cationic surfactant (e.g., DB). In certain preferred aspects, capturing the nucleic acid on mineral matrix is in the presence of a final concentration of LiCl, NaCl, or Potassium Acetate of between about 0.05 M and 1.05 M; about 0.1 M and 0.65 M or about 0.1 M and 0.5 M (e.g., between about 0.1, 0.2, 0.3, 0.4, 0.5, 0.6, 0.7, 0.8, 0.9 and about 1.0 M). In some aspects, a method of the embodiments further comprises adjusting the pH (e.g., using buffers such as Sodium Acetate, Tris HCl, Bis-Tris, Bis-Tris Propane and others). In some cases, adjusting pH can be used in controlling the selective binding properties of a cationic surfactant contemplated herein.

In a further embodiment, there is provided method for selectively condensing large DNA (e.g., genomic DNA) and capturing the DNA to a mineral matrix for purification comprising (a) contacting a nucleic acid containing sample (e.g., a bacterial or mammalian cell lysate) with a phase separation reagent comprising a cationic surfactant of Formula I (e.g., DB) and (b) capturing the phase separated nucleic acid to the mineral matrix (e.g., a silica-based matrix, such as borosilicate glass fiber) in the presence of an effective amount of a salt selected from the group consisting of NaCl, NaoAc, KCl, KoAc, LiCl, LioAc, sodium formate, potassium formate, lithium formate, calcium chloride, and magnesium chloride, thereby selectively capturing large DNA with the mineral matrix. For example, in some aspects, the salt solution comprises a lithium salt, e.g., LiCl present at a desired final concentration. In certain aspects, capturing the nucleic acid with the mineral matrix is in the presence of a final concentration (M) of about 0.05 M-1.0 M, about 0.25 M-0.9 M, about 0.5 M-0.7 M, about 0.55 M-0.7 M, or about 0.6 M-0.7 M LiCl and a final concentration (w/v) of about 0.05 to 5% or 10%, e.g., about 0.05-1%, about 0.1-0.8%, about 0.2-0.5%, about 0.1-0.25%, about 0.2-0.3%, about 0.25-0.3%, about 0.25%-0.4%, about 0.25-0.5% of the cationic surfactant (e.g., DB). For example, in some aspects, the salt solution comprises a sodium salt, e.g., NaCl present at a desired final concentration. In certain aspects, capturing the nucleic acid with the mineral matrix is in the presence of a final concentration (M) of about 0.05 M-1.0 M, about 0.25 M-0.9 M, about 0.5 M-0.7 M, about 0.55 M-0.7 M, or about 0.6 M-0.7 M NaCl and a final concentration (w/v) of about 0.05-1%, about 0.1-0.8%, about 0.2-0.5%, about 0.1-0.25%, about 0.2-0.3%, about 0.25-0.3%, about 0.25%-0.4%, about 0.25-0.5% of the cationic surfactant (e.g., DB). In certain aspects, capturing the nucleic acid with the mineral matrix is in the presence of a final concentration (M) of about 0.025M-0.5M, about 0.125M-0.5M, about 0.15 M-0.375 M, about 0.2 M-0.4 M, or about 0.375 M-0.5 M KoAc and a final concentration (w/v) of about 0.05-1%, about 0.1-0.8%, about 0.2-0.5%, about 0.1-0.25%, about 0.2-0.3%, about 0.25-0.3%, about 0.25%-0.4%, about 0.25-0.5% of the cationic surfactant (e.g., DB). In certain preferred aspects, capturing the nucleic acid on mineral matrix is in the presence of a final concentration of LiCl, NaCl, or Potassium Acetate of between about 0.05 M and 1.05 M; about 0.1 M and 0.65 M or about 0.1 M and 0.5 M (e.g., between about 0.1, 0.2, 0.3, 0.4, 0.5, 0.6, 0.7, 0.8, 0.9 and about 1.0 M). In certain preferred aspects, capturing the nucleic acid on mineral matrix is in the presence of a final concentration of NaCl, LiCl, or KoAc of between about 0.5 M and 0.8 M; about 0.5 M and 0.7 M or about 0.6 M and 0.7 M. As used herein "large DNA" refers to DNA segments longer than about 2 kb, 5 kb or 25 kb, such as genomic DNA. In some aspects, a method of the embodiments further comprises adjusting the pH (e.g., using buffers such as Sodium Acetate, Tris HCl, Bis-Tris, Bis-Tris Propane and others). In some cases, adjusting pH can be used in controlling the selective binding properties of a cationic surfactant contemplated herein.

In some aspects, a phase separation reagent for use according the embodiments comprises a final concentration (w/v) about 0.05-1%, about 0.1-0.8%, about 0.2-0.5%, about 0.1-0.25%, about 0.2-0.3%, about 0.25-0.3%, about 0.25%-0.4%, about 0.25-0.5% of a cationic surfactant of Formula I. In further aspects, a phase separation reagent and/or a salt solution for use according to the embodiments further comprises a pH buffer, such as a Tris or Bis-Tris buffer. Thus, in some aspects, a phase separation reagent and/or salt solution comprises a pH between about 6.0 and about 8.0.

In further aspects, a phase separation reagent (or a salt solution of step c of the instant methods) comprises a salt selected from the group consisting of NaCl, NaoAc, KCl, KoAc, LiCl, LioAc, sodium formate, potassium formate, lithium formate, calcium chloride, and magnesium chloride. Thus, in some aspects, a phase separation reagent or a salt solution for use according to the embodiments comprises a final concentration (M) of about 0.025M-1.05M, about 0.025M-0.5M, about 0.125M-0.5M, about 0.125M-0.6M, about 0.25M-0.375M, about 0.3M-0.4M, or about 0.375M-0.5M lithium chloride or sodium chloride or potassium acetate. In still further aspects, a method of the embodiments comprises contacting a nucleic acid to a mineral matrix in the presence of compound of a cationic surfactant of formula I and a lithium chloride salt. In still further aspects, a phase separation reagent and/or salt solution comprises both lithium chloride and sodium chloride. In still further aspects, a phase separation reagent and/or salt solution comprises both lithium chloride and potassium acetate.

Some aspects of the embodiments concern contacting a nucleic acid-containing sample with a phase separation reagent. In some cases the sample is contacted with the phase separation reagent at different ratios. For example, a ratio of between about 10:1 and 1:10; 6:1 and about 1:2; or about 4:1, 3:1, 2:1 or 1:1 sample:reagent represent different embodiments. Other sample:reagent ratios would be apparent to one skilled in the art and represent additional embodiments where the final concentration of each constituents present in the solution remains the same no matter the ratio of the components that are added in, including the cationic surfactants disclosed herein, prior to bringing the sample in contact with a "Solid Support Carrier" to isolate nucleic acids. In further aspects, eluting a nucleic acid comprises eluting using water or a Tris buffered solution.

In still a further embodiment there is provided a method of isolating plasmid DNA by alkaline lysis, comprising (a) resuspending cells comprising a plasmid (e.g., bacterial cells) in a first aqueous solution; (b) lysing a sample with a second solution; (c) neutralizing the sample and precipitating genomic DNA and proteins with a third solution; (d) capturing of the plasmid DNA to a mineral matrix with a phase separation reagent comprising a cationic surfactant of Formula I; (e) treating the captured plasmid DNA with a salt solution, thereby enhancing the retention of captured nucleic acid; (f) washing the captured plasmid DNA with an organic wash solution; and (g) eluting the plasmid DNA, thereby isolating the plasmid DNA. The use of enzymatic, chemical lysis techniques, or physical lysis such as heat could also be used for isolation of plasmid DNA. In still a further embodiment there is provided a method of isolating plasmid DNA, comprising (a) obtaining a plasmid DNA sample (e.g., a cell lysate produced by enzymatic, chemical or physical lysis); (b) capturing of the plasmid DNA to a mineral matrix with a phase separation reagent comprising a cationic surfactant of Formula I; (c) treating the captured plasmid DNA with a salt solution, thereby enhancing the retention of captured nucleic acid; (d) washing the captured plasmid DNA with an organic wash solution; and (e) eluting the plasmid DNA, thereby isolating the plasmid DNA.

In certain aspects, resuspending cells in a first solution comprises resuspending cells in a buffered solution comprising a chelator, such a Tris buffered solution comprising EDTA. In still further aspects, a second solution (for use in lysing step according to the embodiments) comprises sodium hydroxide, sodium dodecyl sulfate. In some cases, a lysing in step (b) is performed for less than about 10 minutes, such as for 1-2, 1-5 or 1-8 minutes. In further aspects, a third solution (for use in neutralizing the sample) comprises potassium acetate (e.g., in a=concentration of about 0.1-3M, about 0.1-2M, about 0.1-1M, about 0.1M to 0.3M, or about 0.25M) and that may optionally contain RNAse A as this may also be present in the resuspension buffer (P1). In some cases, a method of the embodiments further comprises clearing the precipitate after the neutralizing step (step (c)), such as by filtration using cellulose paper, silica, or glass fiber or by centrifugation. In still further aspects, the first solution, second solution, third solution, and/or the phase separation reagent comprise a dye. In preferred aspects, the first solution, second solution, third solution, and/or the phase separation reagent comprise dyes having different colors.

In certain aspects, a method of the embodiments comprises a phase separation reagent comprising a cationic surfactant or an ionic liquid. For example, the phase separation reagent cation can be domiphen bromide, myristoylcholine chloride, benzyldimethyl(2-dodecyloxyethyl)-ammonium chloride, benzethonium chloride, cetylpyridinium chloride, dodecylpyridinium chloride, 1-decyl-3-methylimidazolium chloride, 1,3-didecyl-2-methylimidazolium chloride, lauryl choline chloride, 1-dodecyl-2-methyl-3-benzimidazolium chloride, 4-carboyl-1-N-hexadecyl pyridinium chloride, N-ethyl-N,N-dimethyl-2-(10-undecenoylamino) ethanaminium bromide, or benzethonium chloride. In preferred aspects, the phase separation reagent is an ammonium cationic surfactant. In further preferred aspects, the cationic surfactant is domiphen bromide. In still further aspects, a phase separation reagent comprises an ammonium cationic surfactant and an anionic surfactant. For example, the anionic surfactant can be present in a final concentration of between about 0.001 and 1% or between about 0.001 and 0.1%.

In some embodiments, methods provided herein employ silica based chromatography that allows for elution into small volumes of water, TE, or elution buffer. However, other forms of chromatography are also contemplated. The resulting nucleic acid whether it be genomic DNA, plasmid DNA, cell-free DNA, or RNA, is suitable for any molecular biological application, including, PCR, restriction digestions, transfection, sequencing, transcriptions, ligations, cloning, among others sensitive applications. The stability of DNA including genomic DNA and plasmid DNA isolated by this novel method is enough that they may be stored for prolonged times at room temperature.

It is also recognized that specific embodiments of this invention can be adapted for isolation of any nucleic acid from a variety of sources. For example, nucleic acids may be isolated from cultured cells, bacteria, yeast, blood, solid tissues, plant tissues, sputum, lymph fluid, Cerebrospinal fluid (CSF), urine or serum samples. In some aspects, a sample for nucleic acid isolation is a bacterial culture, a fungal culture, a urine sample or a serum sample.

In still a further embodiment there is provided a kit for nucleic acid (e.g., genomic DNA, plasmid, and RNA) purification comprising a phase separation reagent comprising a cationic surfactant of Formula I. Such a kit may further comprise a mineral matrix, a first suspension solution, a second lysis solution, a third neutralization solution, a phase separation solution, a treatment solution, a wash solution, an elution solution, columns (or plates), a reservoir, a filter (e.g., a syringe filter), collection tubes (or plates), and/or instructions for using the kit.

In still yet a further embodiment there is provided a composition comprising (i) a cationic surfactant of Formula I; (ii) a salt selected from the group consisting of NaCl, NaoAc, KCl, KoAc, LiCl, LioAc, sodium formate, potassium formate, lithium formate, calcium chloride, and magnesium chloride; and (iii) a mineral matrix, comprising nucleic acid molecules (e.g., genomic DNA or plasmid DNA molecules) captured thereto. For example, the prepared sample composition may comprise final concentrations immediately prior to contacting the solution with a solid support carrier of about 0.05-1%, about 0.1-0.8%, about 0.2-0.5%, about 0.1-0.25%, about 0.2-0.3%, about 0.25-0.3%, about 0.25%-0.4%, about 0.25-0.5% final concentration (w/v) of a cationic surfactant of Formula I (e.g., DB). In further aspects, the composition comprises about 0.05 M-1.0 M, about 0.2 M-0.9M about 0.25 M-0.8 M, about 0.5 M-0.7 M, about 0.55 M-0.7 M, or about 0.6 M-0.7 M about 0.1 M, about 0.2 M about 0.3 M about 0.4 M, about 0.5 M about 0.6 M about 0.7 M about 0.8 M, about 0.9 M about 1 M salt, such a lithium salt (e.g., lithium chloride), final concentrations (M). In still further aspects, the mineral matrix of the composition is a silica-based matrix, such as borosilicate glass fiber. In further aspects, the composition comprises about 0.05 M-1.0 M, about 0.2 M-0.9M about 0.25 M-0.8 M, about 0.5 M-0.7 M, about 0.55 M-0.7 M, or about 0.6 M-0.7 M about 0.1 M, about 0.2 M about 0.3 M about 0.4 M, about 0.5 M about 0.6 M about 0.7 M about 0.8 M, about 0.9 M about 1 M salt, such a sodium salt (e.g., sodium chloride), final concentrations (M). In still further aspects, the mineral matrix of the composition is a silica-based matrix, such as borosilicate glass fiber. In further aspects, the composition comprises about 0.05 M-1.0 M, about 0.2 M-0.9M about 0.25 M-0.8 M, about 0.5 M-0.7 M, about 0.55 M-0.7 M, or about 0.6 M-0.7 M about 0.1 M, about 0.2 M about 0.3 M about 0.4 M, about 0.5 M about 0.6 M about 0.7 M about 0.8 M, about 0.9 M about 1 M salt, such a potassium salt (e.g., potassium acetate), final concentrations (M). In still further aspects, the mineral matrix of the composition is a silica-based matrix, such as borosilicate glass fiber. In further aspects, the composition comprises a mixture of lithium salts such as lithium chloride, sodium salts such as sodium chloride, and potassium salts such as potassium acetate. The composition comprises about 0.05 M-1.0 M, about 0.2 M-0.9M about 0.25 M-0.8 M, about 0.5 M-0.7 M, about 0.55 M-0.7 M, or about 0.6 M-0.7 M about 0.1 M, about 0.2 M about 0.3 M about 0.4 M, about 0.5 M about 0.6 M about 0.7 M about 0.8 M, about 0.9 M about 1 M salt, or some denomination of each of the salts in combination or denomination described. In some aspects, a method of the embodiments further comprises adjusting the pH (e.g., using buffers such as Sodium Acetate, Tris HCl, Bis-Tris, Bis-Tris Propane and others).

In a further embodiment, there is provided a method for purification of DNA (e.g., genomic DNA) from an adhesion resin. For example, in some aspects, methods of the embodiments can be used to isolate genomic DNA from a soluble tape that is used to lift cells from a surface (e.g., from a fingerprint).

As used herein the phrase "elution profile" refers to the proportion of nucleic acid eluted from a binding matrix in a first elution versus successive elutions (e.g., a second and third elution). Methods of the embodiments preferable produce elution profile wherein the majority proportion of the DNA (e.g., greater than 50%, 60%, 70%, 80% or 90%) bound to a matrix is eluted in a first elution relative to a second (or second and third) elution.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-B—Titration of NaCl with 1-decyl-3-methylimidazolium chloride. Agarose gel electrophoresis of a solution of pDNA/degraded RNA purified using a sodium chloride titration with 1-decyl-3-methylimidazolium chloride. Each lane is labeled with the concentration of NaCl (M). L=1 kb ladder. pDNA=plasmid DNA. (A) Five minute run time (RNA check). (B) Forty-five minute run time.

FIGS. 3A-D—Titration of NaCl with cetylpyridinium bromide. Agarose gel electrophoresis of nucleic acid samples purified from bacterial culture using a sodium chloride titration of various cetylpyridinium bromide (CPB) concentrations. Each lane is labeled with the concentration of NaCl (M). L=1 kb ladder. pDNA=plasmid DNA. RNA=degraded RNA. Gels were electrophoresed for 5 minutes as an RNA check. (A) 1% CPB. (B) 0.75% CPB. (C) 0.5% CPB. (D) 0.25% CPB.

FIGS. 4A-B—Titration of NaCl with decylpyridinium chloride. Agarose gel electrophoresis of nucleic acid samples purified from bacterial culture using a sodium chloride titration of decylpyridinium chloride. Each lane is labeled with the concentration of NaCl (M). L=1 kb ladder. pDNA=plasmid DNA. RNA=degraded RNA. (A) Five minute run time (RNA check). (B) Forty-five minute run time.

FIGS. 5A-B & 5C-E—Titration of NaCl and LiCl with domiphen bromide using nucleic acids in solution. Agarose gel electrophoresis of a solution of pDNA/degraded RNA purified using either a sodium chloride titration or a lithium chloride titration of domiphen bromide (DB). Each lane is labeled with the concentration of NaCl (M) or LiCl (M). *=Control. L=1 kb ladder. pDNA=plasmid DNA. (A and B) Five minute run time (RNA check). (C-E) Forty-five minute run time.

*=Control Plasmid DNA. L=1 kb ladder. pDNA=plasmid DNA. RNA=degraded RNA. (A and C) Five minute run time (RNA check). (B and D) Forty-five minute run time. (E) Agarose gel image depicting the quantities of plasmid DNA isolated after using varying concentrations of LiCl (M) in the first wash buffer. Each lane is labeled with the concentration of LiCl (M).

FIGS. 7A-B; 7C-D; and 7E-F—Evaluation of various salts and their effects on total recovery and selectivity of nucleic acids recovered. Agarose gel electrophoresis of nucleic acid samples purified from bacterial culture using various salt titrations of DB. Each lane is labeled with the concentration of salt (M). L=1 kb ladder. pDNA=plasmid DNA. RNA=degraded RNA. (A, C, and E) Five minute run time (RNA check). (B, D, and F) Forty-five minute run time. (C and D) * indicate supplementation with 0.5 M LiCl.

FIGS. 8A-B and 8C-D—Effect of pH on capture capacity and RNA elimination while using 1 M KoAc using DB. Agarose gel electrophoresis of nucleic acid samples purified from bacterial culture using LiCl titration of DB at various pH values and N-Lauroylsarcosine sodium salt concentrations. L=1 kb ladder. pDNA=plasmid DNA. RNA=degraded RNA. Circled concentrations indicate the "window" in which the small nucleic acid fragments were selectively removed. (A and B) Each lane is labeled with the concentration of LiCl. (C and D) Each lane is labeled with the concentration of N-Lauroylsarcosine. (A and C) Five minute run time (RNA check). (B and D) Forty-five minute run time.

FIGS. 9A-B—Evaluation of various salts, pH, and N-Lauroylsarcosine sodium salt to determine an optimal condition for capturing DNA using DB. Agarose gel electrophoresis of nucleic acid samples purified from bacterial culture using various LiCl concentrations, various pH values, and various N-Lauroylsarcosine concentrations. L=1 kb ladder. BL=blank. pDNA=plasmid DNA. Each lane is labeled with a sample ID (see, Table 2). (A) Five minute run time (RNA check). (B) Forty-five minute run time.

FIGS. 10A-B—Determination of capture conditions. Agarose gel electrophoresis of nucleic acid samples purified from bacterial culture using various pH values and LiCl concentrations. L=1 kb ladder. pDNA=plasmid DNA. 2× indicates that two preps were loaded through the same column. 1 h indicates a 1 hour incubation in the phase separation buffer prior to loading onto the column. Each lane is labeled with a sample ID (see, Table 3). (A) Five minute run time. (B) Forty-five minute run time.

Figure 11:
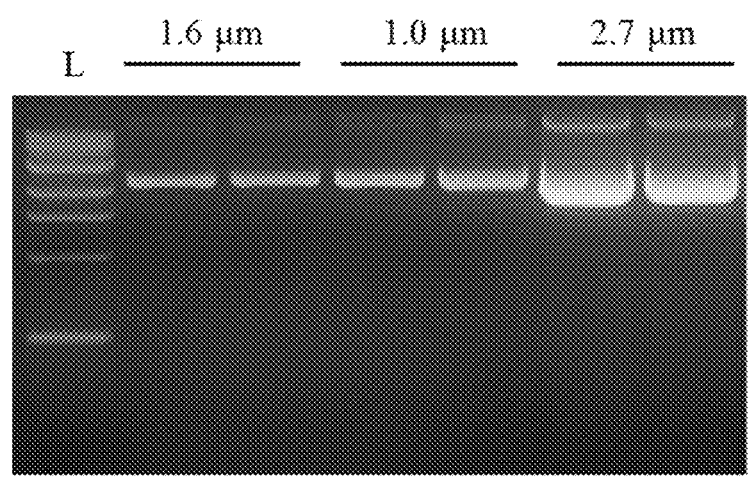

FIG. 11—Matrix porosity vs. nucleic acid recovery. Neutralized bacterial lysate prepared from 35 mL of overnight culture was loaded onto a spin column containing borosilicate glass fiber with a nominal particle retention rating of either 1.0 μm (Porex Grade B), 1.6 μm (Porex Grade A), or 2.7 μm (Porex Grade D) using a CTAB solution.

Figure 12:
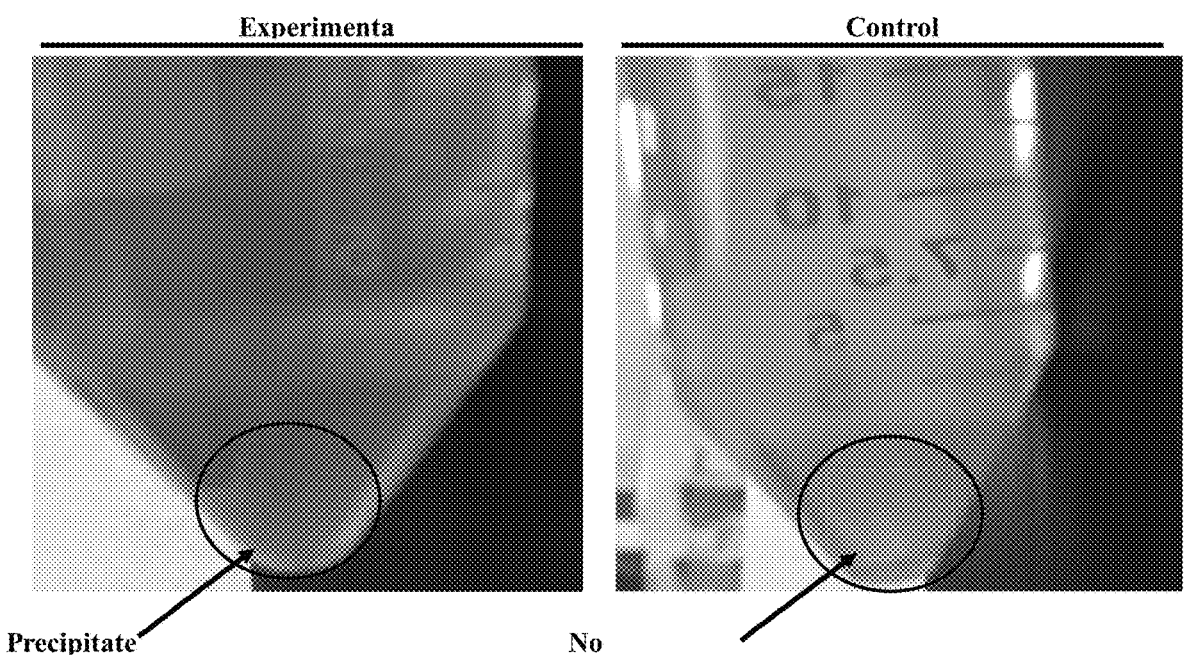

FIG. 12—Capture of Plasmid. Neutralized bacterial lysate prepared from 50 mL of overnight culture was centrifuged to examine if a precipitate (ppt) formed after addition of a P4 buffer (left Experimental with ppt, right control (no ppt).

Figure 13:
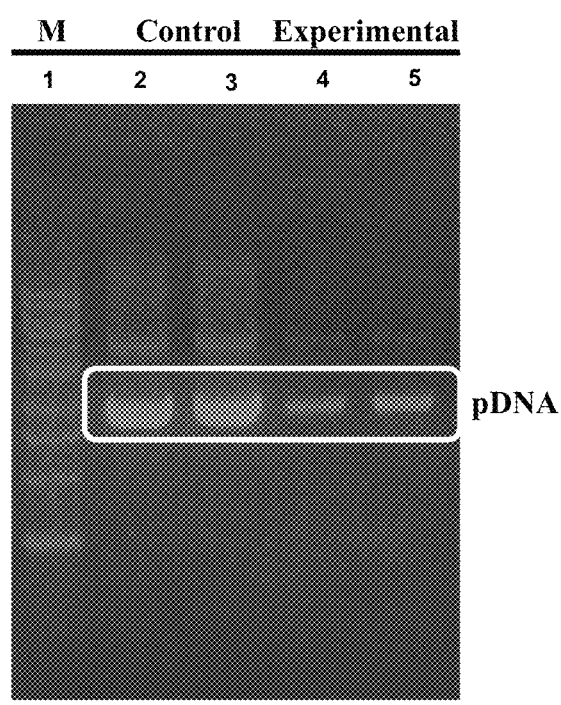

FIG. 13—Capture of Plasmid Gel. Approximately 10 μl of elution from Experimental and controls from Example 11 were run on an agarose gel to visualize the DNA (1M: 1 kb Marker, 2-3 Experimental, 4-5: Control).

FIGS. 14A-B—Evaluation of Tris-HCl Buffer. Substitution of Bis-Tris for Tris-HCl shifts optimal LiCl concentration of Domiphen Bromide based phase separation buffer. About 10 μl of elution was visualized following 20 min (A) to check for undesirable RNA contamination (RNA Check) and 60 min (B) in a full length run to examine plasmid isolation in agarose gel electrophoresis. In each FIG. 12 A-B the first two lanes are controls with Bis-Tris as the buffer component. LiCl concentrations of 0.5M, 0.75M, 1.0M, 1.15M, and 1.25M are shown to titrate the preferred LiCl concentration for plasmid capture. The Marker (M) is a 1 kb DNA Marker.

FIGS. 15A-B—Evaluation of various cationic surfactants for nucleic acid isolation. Agarose gel electrophoresis of nucleic acid samples purified from bacterial culture using various NaCl concentrations and various cationic surfactants with a forty-five minute run time. L=1 kb ladder. Each group of lanes is labeled with the cationic surfactant and then within each group the different NaCl concentrations are indicated.

Figure 16:
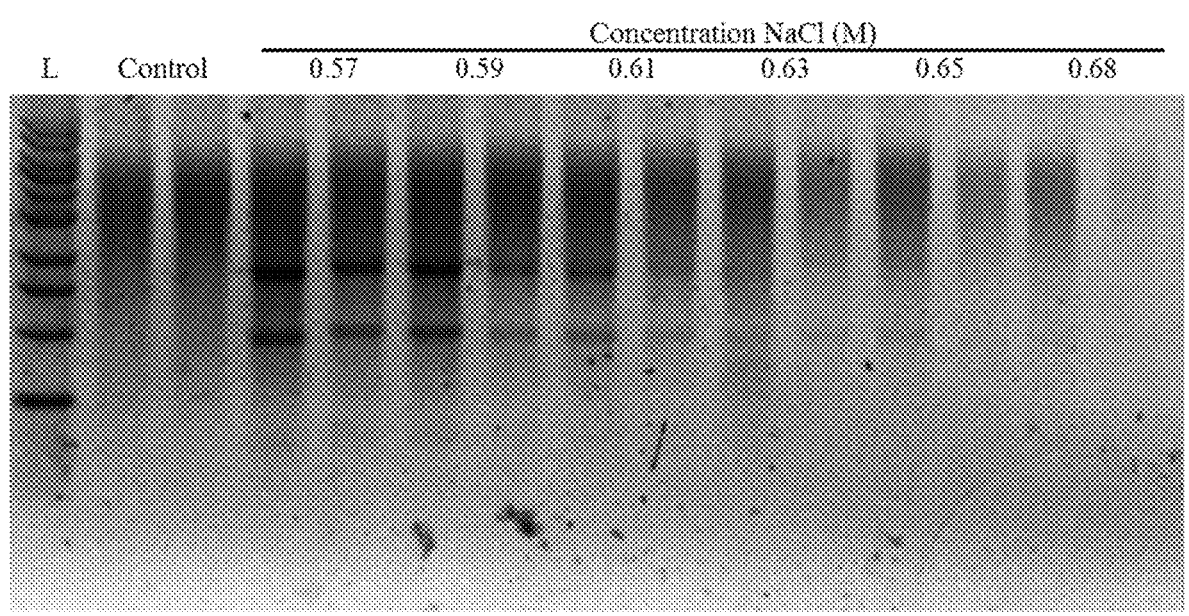
Figure 17:
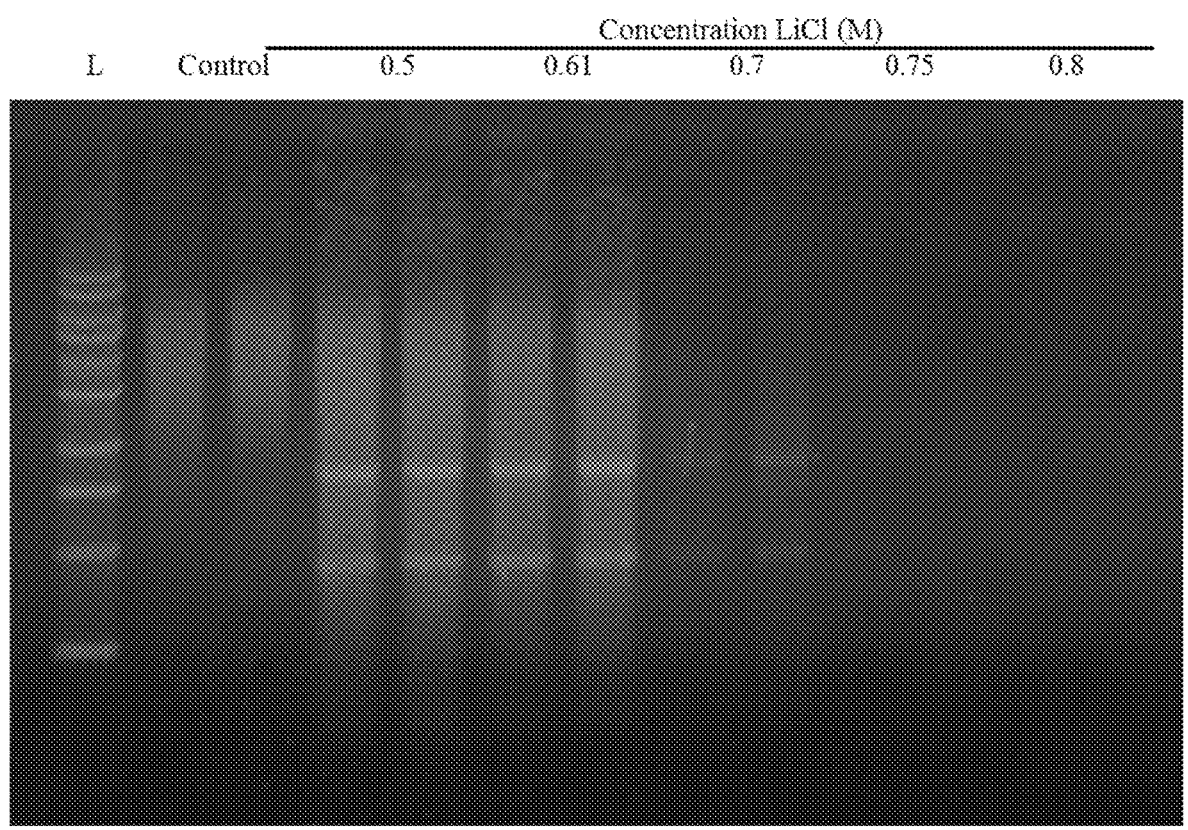

FIGS. 16-17—Genomic DNA Isolation using Domiphen Bromide. Agarose gel electrophoresis of nucleic acid samples purified from HeLa cell culture using various NaCl (FIG. 16) and LiCl (FIG. 17) concentrations with a forty-five minute run time. L=1 kb ladder. Two samples at each concentration indicated are shown.

Figure 18:
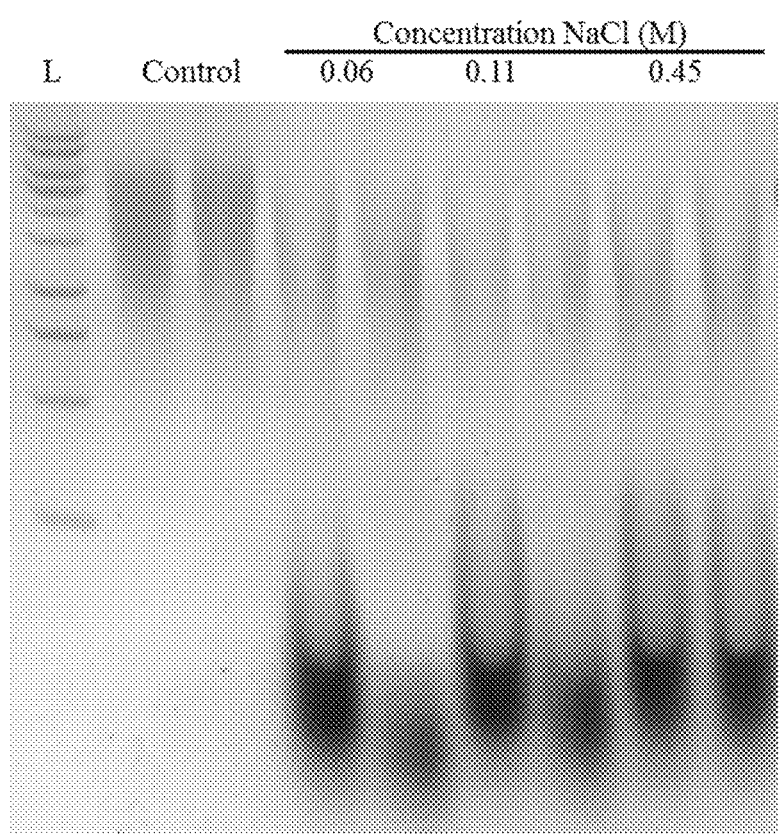

FIG. 18—Binding the Surfactant-Nucleic Acid Complex to Magnetic Beads using Domiphen Bromide. Agarose gel electrophoresis of nucleic acid samples purified from yeast culture using magnetic-silica particles as the solid phase carrier in various NaCl concentrations with a forty-five minute run time. L=1 kb ladder.

FIGS. 19A-B—Titration of buffer, pH, and NaCl to optimize Genomic DNA binding using Domiphen Bromide. Agarose gel electrophoresis of nucleic acid samples purified from bacterial culture using various NaCl concentrations and pH values. L=1 kb ladder. Con=Control.

Figure 20A:
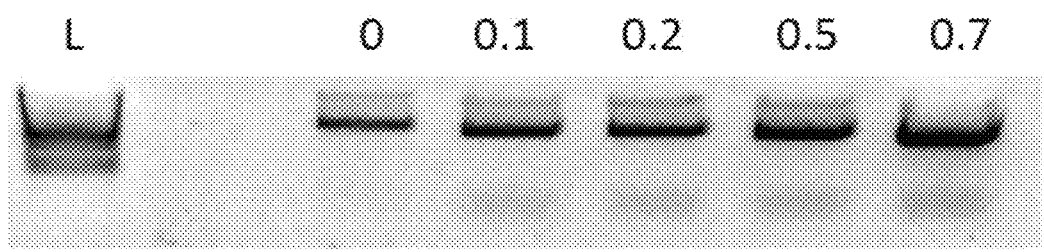
Figure 20B:
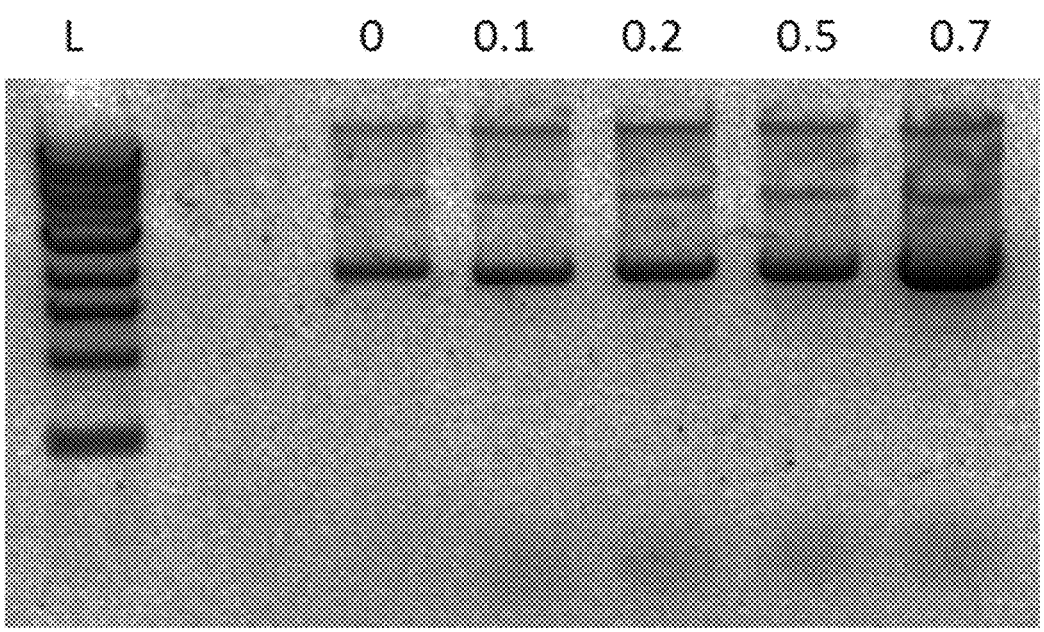

FIG. 20A-B—Treatment solution was evaluated with increasing concentrations of sodium chloride. Agarose gel electrophoresis of nucleic acid samples was performed from purified from E. coli culture using 0, 0.1, 0.2, 0.5, 0.7 M NaCl. Each lane is labeled with the concentration of NaCl (M). L=1 kb ladder. (A) Five minute run time (RNA check). (B) Forty-five minute run time.

DESCRIPTION OF ILLUSTRATIVE EMBODIMENTS

Embodiments of the present invention provides an efficient, safe and inexpensive method for the isolation and/or cleaning of nucleic acids such as genomic DNA or plasmid DNA using a phase separation reagent such as domiphen bromide (DB) with high selectivity (e.g. capture of DNA versus RNA) and tunability (e.g. controlling capture of large plasmids over other sized species). The use of such surfactants allows for the ability to isolate nucleic acids in high purity at high concentrations using inexpensive materials, such as glass fiber membranes. Furthermore, the use of DB in particular increased the capture capacity of silica by nearly 17 fold as compared to using chaotropic salt-driven binding. This high recovery of plasmid per milligram of mineral matrix over other nucleic acids such as RNA allows for high selectivity and the production of excellent elution profiles and highly concentrated plasmid. High plasmid recovery in also unexpectedly enhanced or boosted with DB by treatment of captured plasmid with salt solutions. Further with DB the elution profile can be fortuitously tuned or controlled to isolate preferentially large DNA species such as genomic DNA or plasmid DNA. Such DB mediated elution can be defined as the fraction of DNA released each time a low salt solution or water is added to the matrix which is then separated by convenient methods such as centrifugation. Other phase separation reagents failed to display similar selectivity or tunability for nucleic acid capture compared to DB. A desired elution profile is one that reflects a 100% release of nucleic acids, preferentially plasmid DNA, from the mineral matrix in a single elution however generally an 80-90% release of the nucleic acids on the first elution is highly desirable. Approximately, 80-90% is a representative elution profile is attained using the cationic surfactants disclosed herein.

Certain embodiments of the present invention allow for the concentration of nucleic acids from large volumes of liquid by capture by primarily precipitation with different phase separation reagents, from samples including, but not limited to sputum, lymph fluid, cerebrospinal fluid (CSF), urine, serum, sweat, various aspirates, and other liquid biological sources, without the need for excessively large volumes of ethanol, isopropanol, or other commonly used DNA precipitating agents.

Embodiments of the present invention as provide a method of rapidly purifying nucleic acids and selectively genomic DNA and plasmid over smaller degraded nucleic acids such as RNase A digested RNA in a genomic or plasmid preparation. The present method can be performed at the same speed as chaotropic salt-based methods, achieves recoveries similar to that of anion exchange based chromatography and purity greater than both of these methods directly from a spin column. This is especially critical when dealing with large sample sizes such as bacterial cultures of 100 ml, 1 L, or larger, since the amount of silica required using chaotropic salt driven binding methods requires excessively large quantities of mineral matrix. In addition this method does not suffer from the extremely slow processing times of anion exchange methods that can require up to 3 hours to purify DNA.

Mineral matrices that could be implemented with embodiments of the present invention include a porous or non/porous carrier composed of metal oxides and or mix metal oxides. These metal oxides include materials commonly used in the art such as silicon-oxygen based compounds. Borosilicate or silicate in the form of glass fibers, silica gel, zeolites, or diatomaceous earth are most commonly used due their inexpensive and non-toxic properties, however other minerals such as aluminum oxide, titanium dioxide, zirconium dioxide or a mixture thereof could be used in different embodiments.

In addition cellulose based resins and or other membranes that can exclude based on size could be used in various embodiments of the invention. Other commonly used filtration techniques and matrix compositions or resins could also be used, e.g. ion exchange.

Alkaline lysis embodiments of the present invention may incorporate the use of dyes in the purification buffers for visual monitoring of the steps for preparing the bacterial lysate filtrate. See, U.S. Pat. No. 7,754,873, incorporated herein by reference.

Nucleic acids specifically genomic DNA can be isolated from microbial fermentation and/or eukaryotic cellular cultures or biological body fluids (e.g. sputum, lymph fluid, cerebrospinal fluid (CSF), urine, serum, sweat, various aspirates, and other liquid biological sources) and solid tissues. Nucleic acids specifically plasmid DNA can be isolated from microbial fermentation. The plasmid DNA can be preferentially isolated from *Escherichia coli* (*E. coli*) strains that are used to produce such material for molecular biology manipulations. It is recognized that other prokaryotic bacterial or eukaryotic species can also be used as vehicles for the purification of nucleic acids and plasmid DNA. The nucleic acid to be purified is typically DNA especially, or genomic DNA or plasmid DNA and like vectors of a variety of sizes, but could also be RNA, in alternative embodiments. In the case of plasmid DNA and like vectors it may or may not contain foreign DNA sequences, though generally will for most applications.

The cellular culture can be grown in a variety of culture mediums that can be modified to alter or regulate replication of the plasmid DNA, RNA, or other nucleic acid molecules. The cells are harvested by centrifugation and the culture media removed to provide a cell pellet. In a preferred embodiment the nucleic acid that is isolated is plasmid DNA that can be of a variety of sizes with specific control elements that either comprises heterologous DNA or synthetic sequences that are commonly known in the art.

The isolation of plasmid DNA is a preferred embodiment of the present invention. All steps of the preferred embodiment of the present invention may be carried out at room temperature, about 15-30° C. Isolation of plasmid DNA is well known in the art. A preferred method of plasmid isolation comprises modified mild alkaline lysis of host cells containing a plasmid, sodium hydroxide (NaOH) and sodium dodecyl sulphate (SDS), NaOH/SDS, denaturation, and precipitation of unwanted cellular macromolecular components as an insoluble precipitate, coupled to column-based silica, or other chromatography or purification methods. Isolation buffers based on alkaline lysis protocols are well known in the art and variations of compositions are contemplated as embodiments of the present invention that are compatible with various commercially available chromatographic columns and technologies. Alkaline lysis procedures generally use sodium acetate, potassium acetate, as well as a variety of other salts, including chaotropic salts. Ribonuclease RNAase A is commonly added to degrade contaminating RNA from the lysate. The clarification of the lysate can be performed by centrifugation or filtration methods both of which are known in the art. The plasmid is pure, typically with an OD260/280 ratio above 1.8. The plasmid DNA is suitably pure for use in the most sensitive experiments.

Yeast species (e.g. *Saccharomyces cerevisiae*), fungi species, other microorganisms, human (*Homo sapiens*) liquid tissue (e.g. sputum, lymph fluid, cerebrospinal fluid (CSF), urine, serum, sweat, various aspirates, and other liquid biological sources) solid tissue, or tissue from a variety of species commonly used in diagnostic, research or clinical laboratories are contemplated as compatible with this purification procedure as sources of DNA and are all alternative embodiments of the present invention. Procedures for handling and preparing samples from these various species are well known in the art and are reported in the scientific literature.

I. GENERAL PROTOCOL FOR ISOLATING GENOMIC DNA

Certain embodiments of the invention provide a method of selectively isolating genomic DNA from a sample, such as a cell lysate. For example, in some aspects, such a method comprises (a) obtaining a sample comprising genomic DNA; (b) capturing the genomic DNA to a mineral matrix with a phase separation solution comprising DB and a salt (e.g., a potassium and/or sodium salt); (c) washing the mineral matrix and captured genomic DNA with a wash solution; and (d) eluting the genomic DNA, thereby isolating the genomic DNA. A sample, for use according to the embodiments may be any sample that comprises genomic DNA. In some cases, the sample can be a sample from mammalian cells, such as a tissue or cell sample. For example, the sample can a fingerprint residue (e.g., in an adhesive matrix), hair or hair follicle, urine, fecal matter, mucus membrane secretion (e.g., saliva) or a blood sample. Methods for lysis of such samples are well known in the art and can be used in conjunction with the DNA isolation methods disclosed herein.

Thus, in some aspects, there is provided method for selectively condensing large DNA (e.g., genomic DNA, artificial chromosomes, cosmids, plasmid) and capturing the DNA to a mineral matrix for purification comprising (a) contacting a nucleic acid containing sample (e.g., a bacterial or mammalian cell lysate) with a phase separation reagent comprising a cationic surfactant of Formula I (e.g., DB) and (b) capturing the phase separated nucleic acid to the mineral matrix (e.g., a silica-based matrix, such as borosilicate glass fiber) in the presence of an effective amount of a salt selected from the group consisting of lithium salts, sodium salts, potassium salts, magnesium salts, calcium salts and mixtures thereof (e.g., NaCl, NaoAc, KCl, KoAc, LiCl, LioAc, sodium formate, potassium formate, lithium formate, calcium chloride, and magnesium chloride), thereby selectively capturing large DNA with the mineral matrix. For example, in some aspects, the salt solution comprises a lithium salt, e.g., LiCl present at a desired final concentration. In certain aspects, capturing the nucleic acid with the mineral matrix is in the presence of a final concentration (M) of about 0.05 M-1.05 M, about 0.25 M-0.9 M, about 0.5 M-0.7 M, about 0.55 M-0.7 M, or about 0.6 M-0.7 M LiCl and a final concentration (w/v) of about 0.05 to 5% or 10%, e.g., about 0.05-1%, about 0.1-0.8%, about 0.2-0.5%, about 0.1-0.25%, about 0.2-0.3%, about 0.25-0.3%, about 0.25%-0.4%, about 0.25-0.5% of the cationic surfactant (e.g., DB). In some aspects, the salt solution comprises a sodium salt, e.g., NaCl present at a desired final concentration. In certain aspects, capturing the nucleic acid with the mineral matrix is in the presence of a final concentration (M) of about 0.05 M-1.0 M, about 0.25 M-0.9 M, about 0.5 M-0.7 M, about 0.55 M-0.7 M, or about 0.6 M-0.7 M NaCl and a final concentration (w/v) of about 0.05-1%, about 0.1-0.8%, about 0.2-0.5%, about 0.1-0.25%, about 0.2-0.3%, about 0.25-0.3%, about 0.25%-0.4%, about 0.25-0.5% of the cationic surfactant (e.g., DB). In certain aspects, capturing the nucleic acid with the mineral matrix is in the presence of a final concentration (M) of about 0.025M-0.5M, about 0.125M-0.5M, about 0.15 M-0.375 M, about 0.2 M-0.4 M, or about 0.375 M-0.5 M KoAc and a final concentration (w/v) of about 0.05-1%, about 0.1-0.8%, about 0.2-0.5%, about 0.1-0.25%, about 0.2-0.3%, about 0.25-0.3%, about 0.25%-0.4%, about 0.25-0.5% of the cationic surfactant (e.g., DB). In certain preferred aspects, capturing the nucleic acid on mineral matrix is in the presence of a final concentration of LiCl, NaCl, or Potassium Acetate of between about 0.05 M and 1.05 M; about 0.1 M and 0.65 M or about 0.1 M and 0.5 M (e.g., between about 0.1, 0.2, 0.3, 0.4, 0.5, 0.6, 0.7, 0.8, 0.9 and about 1.0 M). In further preferred aspects, capturing the nucleic acid on mineral matrix is in the presence of a final concentration of NaCl, LiCl, or KOAc of between about 0.5 M and 0.8 M; about 0.5 M and 0.7 M or about 0.6 M and 0.7 M. As used herein "large DNA" refers to DNA segments longer than about 2 kb, 5 kb, 10 kb, 20 kb or 25 kb, such as genomic and plasmidDNA or other forms such as artificial chromosomes, cosmids and the like. In some aspects, a method of the embodiments further comprises adjusting the pH (e.g., using buffers such as Sodium Acetate, Tris HCl, Bis-Tris, Bis-Tris Propane and others). In some cases, adjusting pH can be used in controlling the selective binding properties of a cationic surfactant contemplated herein.

In preferred aspects, selectively isolating genomic DNA from a sample, comprises capturing the genomic DNA to a mineral matrix in the presence of DB and a sodium salt, such as sodium chloride. For example, in some cases, capturing the genomic DNA to a mineral matrix is in the presence of 0.05% to 1% DB and 0.05 M to 1.0 M NaCl. In further aspects, the capturing the genomic DNA to a mineral matrix is in the presence of DB, NaCl, LiCl and KOAc. In still further aspects, the isolated genomic DNA is essentially free of endotoxins, and PCR inhibitors.

II. GENERAL PROTOCOL FOR ISOLATING PLASMID DNA

Methods of nucleic acid isolation using chaotropic salts comprise (a) alkaline lysis of the starting material, (b) neutralization/precipitation and subsequent capture of the nucleic acids with a solid phase mineral matrix such as with a glass or silica membrane, which is located on a solid support in a centrifuge column; (c solid support carrier with a salt solution that promotes retention of nucleic acids on the mineral or glass matrix, (d) washing of the captured nucleic acids with an organic solvent such as lower alcohols (i.e., C1-5 alcohols); and (e) elution of the nucleic acids with water or a buffer of low ionic strength.

In a preferred embodiment below, the volume of each solution added in steps a-d are equal in volume. Other concentrations/volume ratios could be readily made by those skilled in the art, and represent alternative embodiment. Methods of nucleic acid isolation using the present invention comprise (a) suspension of pelleted bacterial culture in TE buffer (50 mM Tris-Cl, pH 8.0, 10 mM EDTA) (Solution P1). (b) Lysis of cells/sample for a specified amount of time depending on the scale of the prep using a common lysis buffer, e.g., Solution P2 (200 mM NaOH, 1% SDS). Preferably, the incubation lasts from about 1-5 minutes. (c) Neutralization of the alkaline lysis solution and precipitation of genomic DNA and proteins using a common neutralization buffer, (Solution P3) that contains about 1-3 M potassium acetate (KoAc) and about 200 μg/mL RNAse A. Clearance of the precipitated genomic DNA and proteins using a filtration method, such as Whatman cellulose paper, silica, glass fiber, membranes or other commonly used filters. (d) Addition of a phase separation solution (Buffer P4), comprising a phase separating agent of the embodiments. In one preferred embodiment, Solution P4 comprises 0.1-10% (e.g., 1%) domiphen bromide, 0.2 M-2.0 M (e.g., 1.1 M) Tris-HCl, pH 6.0-8.0 (e.g., 7.2), 0.1 M-1.5 M (e.g., 0.8M) lithium chloride and, optionally, 0.1-1.5 M KOAc. The solution containing the cleared lysate and the phase separation buffer is mixed and loaded onto a mineral matrix, e.g., silica or glass fiber. The sample is washed with a salt solution buffered with Tris and protected from heavy metals by EDTA. One preferred embodiment for the wash solution comprises 0.1 M-1.0 M (e.g., 0.45 M) NaCl/5 mM-100 mM (e.g., 40 mM) Tris pH 7-9.5 (e.g., 8.5)/0.05 mM-1.5 mM (e.g., 0.5 mM) EDTA; however, a range of types and concentrations of salts, such as sodium chloride, lithium chloride, or potassium chloride, etc, can be used. The sample is washed with an organic wash that solubilizes the surfactants but forces the nucleic acid to remain precipitated on the mineral matrix. One preferred embodiment for the organic solvent wash solution is greater than 80% (e.g., about 95%)

ethanol. Elution of the nucleic acid from the glass or mineral matrix can be done using water or any standard low salt solution, such as TE.

Although the volume of each buffer changes depending on the volume of bacterial culture used, the volume of each buffer relative to the others is equal in the context of the experiments disclosed herein. For example: 5 mL P1, 5 mL P2, 5 mL P3, and 5 mL P4 was used when 30 ml of bacterial culture was the sample source. However, this is not an absolute requirement of the method, as those skilled in the art could easily adjust the ratios and concentrations of the buffers with routine experimentation. It should be noted that all concentrations are listed in many cases for simplicity as those in the original solution or buffer, not by the final concentration after mixing the four solutions. In other cases the same solutions or buffers may be indicated as final concentrations (w/v, v/v or M) to illustrate preferred compositions. For example, a concentration of 2 M NaCl in Buffer P4 translates to a 0.5 M NaCl final concentration. In a preferred embodiment a phase separation solution comprising starting concentrations of about 0.1-10% (e.g., 1%) domiphen bromide, about 0.2 M-2.0 M (e.g., 1.1 M) Tris-HCl, pH 6.0-8.0 (e.g., 7.2), 0.1 M-1.5 M (e.g., 0.8M) lithium chloride which is added to a cleared lysate where the cleared lysate is the supernatant collected post filtration of the precipitated debris. This translates to a phase separation solution comprising a final concentration comprising about 0.025-2.5% (e.g., 0.25%) domiphen bromide (w/v), about) 0.05 M-0.5M (e.g., 0.275M) Tris-HCl, pH pH 6.0-8.0 (e.g., 7.2), and about 0.025 M-0.375M (e.g., 0.2M) lithium chloride. This phase separation solution allows the capture/retention of Domiphen bromide—Nucleic Acid (DB-NA) complex onto a glass or mineral carrier. This phase separation solution has the unique ability of selectively capturing nucleic acids based upon size. The phase separation solution can be tuned by changing concentrations such that size selection of nucleic acids can be accomplished. The phase separation solution also shows greatly enhanced recovery as compared to chaotropic salts methods. In addition use of DB-NA methodology prevents problems of guandinium contamination which is inhibitory to many downstream applications and notoriously difficult to completely remove.

In a preferred embodiment following the step of capturing nucleic acids with a surfactant such as DB to a glass or mineral matrix further comprises treating the captured nucleic acid with a salt solution which increases retention of nucleic acid on the mineral silica matrix or membrane. This treatment with the salt solution comprises, for example, treatment with a solution comprising 0.1-1.0 M salt, such as NaCl. In some aspects, the salt solution further comprises a pH buffer and/or a chelator. An exemplary salt solution comprises 0.1-1.0 M (e.g., 0.45 M) NaCl, 5 mM-100 mM (e.g., 40 mM) Tris pH 7.0-9.5 (e.g., 8.5) and 0.05 mM-1.5 mM (e.g., 0.5 mM) EDTA. The treatment results in the added retention of nucleic acid on the mineral silica matrix or membrane which dramatically enhances the recovery of nucleic acid. The treatment with the salt buffer is also pertinent to the cleaning of the sample by means of removing weakly bound contaminating molecules that were not removed by the selective capture step. Unlike CTAB-NA-mineral matrix complexes, DB-NA-mineral matrix complexes when treated with a salt solution do not aid in the removal of smaller nucleic acids such as degraded RNA (0113348). However, a salt treatment of the DB-NA-Mineral Matrix has the unexpected effect of dramatically enhancing or boosting retention and therefore recovery of nucleic acid. Further, when using DB, removal of potentially undesirable nucleic acids (e.g.: washing away of small contaminating nucleic acids such as degraded RNA) at this step is unexpectedly achieved indirectly by the high degree of selectivity gained in the capture step effectively removing such unwanted nucleic acid species.

The treatment with the salt buffer is followed by a wash, with a wash solution comprising an organic solvent, such as lower alcohols. If the matrix is not washed with an appropriate organic solvent that removes the detergent then little or no DNA will be removed from the column during the elution step. Without being bound to a particular theory the organic solvent wash solutions are thought to force the nucleic acids to remain precipitated and/or captured to the matrix, while the surfactants are solvated and removed. The alcohol content must be sufficiently high enough or some fraction of the nucleic acids will be lost during the wash step. Common wash buffers known in the art containing ≥70% ethanol could be implemented. However, the preferred wash solutions for the removal of the cationic surfactants disclosed herein comprise about 95% ethanol, or about 90% isopropanol, or about 90% butanol, or about 75% Ethanol/17% Isopropanol/8% water/0.4 mM Tris pH 8.5, 0.004 mM EDTA. The higher alcohol content in these solutions was found to greatly improve retention and therefore recovery of the isolated nucleic acid. In other systems, especially those that use chaotropic salts such as guanidinium thiocyanate require a lower percentage of alcohol in order to ensure that the salts are efficiently removed, which can cause some loss of captured nucleic acids, thereby decreasing overall recovery. These salts are considered harmful to most downstream applications and therefore the user must be particularly careful to prevent salt contamination.

In addition, the protocol is suitable to scale up from small cultures for use in large scale methods for use with mid to large sized cultures, e.g. from about 0.1 mL to several liters or industrial sized cultures using fermentation equipment known in the art, all of which are embodiments of the present invention.

In the following examples the ratios disclosed are preferred, however, this is not an absolute requirement of the method, as those skilled in the art could easily adjust the ratios and concentrations of the buffers with routine experimentation to generate fully functional embodiments.

In one example, 1-5 mL of pelleted bacterial culture may be resuspended in 300 µL of Buffer P1. To this, 300 µL each of Buffer P2, Buffer P3, and Buffer P4 may be added during the course of the protocol. In this example, the treatment to increase yield is performed with 400 µL of salt buffer solution and the wash is performed twice with 400 µL of the organic wash solution.

In another example, 30-50 mL of pelleted bacterial culture may be resuspended in 5 mL of Buffer P1. To this, 5 mL each of Buffer P2, Buffer P3, and Buffer P4 may be added during the course of the protocol. In this example, the treatment to increase yield is performed with 800 µL of salt buffer solution and the critical wash is performed with 800 µL of the organic solvent wash solution.

In yet another example, 100-200 mL of pelleted bacterial culture may be resuspended in 15 mL of Buffer P1. To this, 15 mL each of Buffer P2, Buffer P3, and Buffer P4 may be added during the course of the protocol. In this example, the treatment to increase yield is performed with 5 mL of salt buffer solution and the critical wash is performed with 5 mL of the organic solvent wash solution.

In yet another example, 1-2 L of pelleted bacterial culture may be resuspended in 150 mL of Buffer P1. To this, 15 mL each of Buffer P2, Buffer P3, and Buffer P4 may be added during the course of the protocol. In this example, the treatment to increase yield is performed with about 40 to 50 mL of salt buffer solution and the critical wash is performed with about 80 to 100 mL of the organic solvent wash solution.

Modified Alkaline Lysis Protocol

In further aspects a modified alkaline lysis protocol may be used as disclosed in U.S. Pat. No. 7,867,751, incorporated herein by reference. Thus, in some aspects, there is provided a method for isolating plasmid DNA from bacteria by alkaline lysis, the method comprising the steps of: (a) providing a bacterial suspension comprising bacteria having plasmid DNA; (b) adding a modified P2 reagent directly to the bacterial suspension, wherein the P2 reagent comprises an alcohol to reduce SDS precipitation; (c) adding a modified P3 reagent to the bacterial suspension to produce an alkaline lysate, wherein the modified reagent comprises a chaotropic agent; (d) removing cell debris from the alkaline lysate by filtration or centrifugation to obtain a lysate filtrate; (e) contacting the lysate filtrate with a phase separating agent of the embodiments (e.g., DB) and, optionally, a salt in presence of a mineral matrix thereby capturing DNA to the matrix; (e) washing the plasmid DNA bound to the matrix; and (f) eluting the plasmid DNA.

The cell debris may be removed by centrifugation and transferring the cleared lysate (lysate filtrate) to a DNA capture device or similar device having a DNA binding matrix. The cell debris may also be removed using a filtration apparatus and transferring the lysate filtrate to a DNA capture device or similar device having a DNA binding matrix.

In some aspects, step (d) and (e) are performed concurrently. For example, the filtering can be in the presence of a phase separating agent (and optionally a salt of the embodiments). In this case, the alkaline lysate is passed through a lysate filtration device having a (i) filtering medium and (ii) a DNA binding matrix. For example, the filtering and capturing can be performed using a single centrifugation or pressure step. The lysate filtration device and DNA capture device may be discrete components or a single assembly, i.e., a combined DNA isolation apparatus.

One example of how this method could be performed is through the use of concentrated or otherwise modified lysis and neutralization solutions with buffers (e.g. binding buffer) of the present invention. One skilled in the art would recognize that by adjusting the concentration or form (semisolid, dry solids) of reagents in the modified or unmodified P2 (lysis solution), modified or unmodified P3 (neutralization solution), or P4 (phase separation solution) have been contemplated and would be considered routine optimization. Alternative contemplated embodiments include separating the lysis solution into two solutions wherein the sodium hydroxide is added separately from the SDS. In some cases the neutralization solution may or may not contain guanidine salts. In some cases the modified P2 may or may not contain alcohol to improve solubility of SDS.

Further provided are modified P2 and P3 reagents for use in methods of alkaline lysis. For example, the modified P2 reagent may be a liquid comprising alcohol (to reduce SDS precipitation). Examples of suitable alcohols include isopropanol, 1-propanol, and ethanol. In some case a modified P3 reagent is a liquid comprising a chaotropic agent, and, in some cases, potassium chloride. In still further aspects, a modified P3 reagent may comprise a phase separating agent of the embodiments. In further aspects, the P3 reagent is a solid, comprising a solid acid. Again, in the case of a solid P3, the reagent may comprise a phase separating agent of the embodiments. Alkaline lysis may be performed using liquid, solid, or immobilized P2 or P3 reagents.

III. PHASE SEPARATING AGENTS AND CHEMICAL DEFINITIONS

In certain aspects, the phase separation reagents for use according to the embodiments are heterocycles containing a cationic nitrogen or phosphorous or tetra substituted cationic nitrogen or phosphorous molecule with a long alkyl chain a minimum of 8 carbons long. However, the length of the primary hydrocarbon chain only contributes to the total hydrophobicity of the molecule why the total hydrocarbon content is equally important due to its effect on how the heterocyclic or quaternary ammonium/phosphonium ions interact with the biological molecules. Without being bound to a particular the mechanism by which these molecules act to bind nucleic acids to a mineral matrix is thought to rely on their ability to form micelles with the nucleic acids in aqueous systems. Therefore, based on this theory the only requirement is that the hydrophobic interactions are favorable enough to facilitate micelle formation. A 6 carbon chain with an aromatic residue or two attached may be able to facilitate micelles formation, for example benzethonium chloride. Functional groups, such as ethers, esters, amides, ketones, aldehydes, and halogens, ultimately should not affect the functionality of these molecules so long as micelles can still form, however they can provide previously un-described and surprising beneficial characteristics as in the case of the preferred molecule—domiphen bromide of enhances selectivity and tunability for nucleic acid isolation.

The results disclosed herein show that each surfactant has unique properties that cannot be predicted. That is to say, that the behavior of each phase separation reagent based upon each unique functional group(s) cannot be explicitly predicted by the literature currently available. The preferred surfactant, domiphen bromide, meets the requirements described herein and due to the phenoxyethyl functional group the molecule acquired the ability to select for nucleic acids based upon size. The binding functionality of DB also imparted a significant boost in recovery of DNA when a salt solution was used as a treatment prior to washing with an organic solvent. Such increased recovery of nucleic acids and in particular DNA is not observed for other phase separation agents such as cationic surfactants (U.S. Pat. App. 2008/0113348 and U.S. Pat. No. 8,679,744).

Accordingly, in some aspects, a cationic surfactant comprises the general of Formula I:

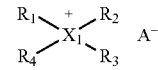

wherein: $X_1$ is nitrogen, phosphorus, N-heteroaryl$_{(C \leq 18)}$ or substituted N-heteroaryl$_{(C \leq 18)}$, provided that when $X_1$ is N-heteroaryl$_{(C \leq 18)}$ or substituted N-heteroaryl$_{(C \leq 18)}$, then $R_2$, $R_3$, and $R_4$ are absent and when $R_2$, $R_3$, and $R_4$ are absent, then $X_1$ is N-heteroaryl$_{(C \leq 18)}$ or substituted N-heteroaryl$_{(C \leq 18)}$; $R_1$ is alkyl$_{(C \leq 30)}$, alkenyl$_{(C \leq 30)}$, alkynyl$_{(C \leq 30)}$, aryl$_{(C \leq 30)}$, aralkyl$_{(C \leq 30)}$, heteroaryl$_{(C \leq 30)}$, heteroaralkyl$_{(C \leq 30)}$, a substituted version of any of these groups or —Y$_1$—Z—Y$_2$; $Y_1$ is alkandiyl$_{(C \leq 6)}$, alkendiyl$_{(C \leq 6)}$, alkyndiyl$_{(C \leq 6)}$, arenediyl$_{(C \leq 6)}$, alkoxydiyl$_{(C \leq 6)}$, or a substituted version of any of these groups; Z is —O—, —NH—, —S—, —C(O)O—, —OC (O)—, —NHC(O)—; or —C(O)NH—; $Y_2$ is alkyl$_{(C≤30)}$, alkenyl$_{(C≤30)}$, alkynyl$_{(C≤30)}$, aryl$_{(C≤30)}$, aralkyl$_{(C≤30)}$, heteroaryl$_{(C≤30)}$, heteroaralkyl$_{(C≤30)}$, or a substituted version of any of these groups; $R_2$, $R_3$, and $R_4$ are each independently alkyl$_{(C≤30)}$, alkenyl$_{(C≤30)}$, alkynyl$_{(C≤30)}$, aryl$_{(C≤30)}$, aralkyl$_{(C≤30)}$, heteroaryl$_{(C≤30)}$, heteroaralkyl$_{(C≤30)}$, a substituted version of any of these groups or —$Y_3$—Z—$Y_4$; $Y_3$ is alkandiyl$_{(C≤6)}$, alkendiyl$_{(C≤6)}$, alkyndiyl$_{(C≤6)}$, arenediyl$_{(C≤6)}$, or a substituted version of any of these groups; Z is —O—, —NH—, —S—, —C(O)O—, —OC(O)—, —NHC(O)—; or —C(O)NH—; $Y_4$ is alkyl$_{(C≤30)}$, alkenyl$_{(C≤30)}$, alkynyl$_{(C≤30)}$, aryl$_{(C≤30)}$, aralkyl$_{(C≤30)}$, heteroaryl$_{(C≤30)}$, heteroaralkyl$_{(C≤30)}$, or a substituted version of any of these groups; and A is an inorganic or organic anion such as fluoride, chloride, bromide, iodide, phosphate, sulfite, sulfate, hydrogen sulfate, thiosulfate, perchlorate, chlorite, carbonate, bicarbonate, phosphate, nitrate, nitrite, acetate, formate, propionate, oxalate, or succinate, malanate, borate, cyanate, thiocyanate, hydroxide or other common anions known in the art such as benzoate, salicylate, or p-toluenesulfonate; provided that when $R_2$, $R_3$ and $R_4$ are alkyl$_{(C≤30)}$, alkenyl$_{(C≤30)}$, alkynyl$_{(C≤30)}$, aryl$_{(C≤30)}$, aralkyl$_{(C≤30)}$, heteroaryl$_{(C≤30)}$, heteroaralkyl$_{(C≤30)}$, or a halo substituted version of any of these groups and $X_1$ is nitrogen or phosphorus, then $R_1$ is —$Y_1$—Z—$Y_2$. In some aspects, a cationic surfactant comprises a structure according to formula I wherein if $X_1$ is a nitrogen or phosphorous and if $R_1$ is not a substituted N-heteroaryl or a N-heteroaryl, then, $Y_1$ is alkandiyl$_{(C≤6)}$, alkendiyl$_{(C≤6)}$, alkandiyl$_{(C≤6)}$, arenediyl$_{(C≤6)}$, alkoxydiyl$_{(C≤6)}$, or a substituted version of any of these groups; Z is —O—, —NH—, —S—, —C(O)O—, —OC(O)—, —NHC(O)—; or —C(O)NH—; and $Y_2$ is alkyl$_{(C≤30)}$, alkenyl$_{(C≤30)}$, alkynyl$_{(C≤30)}$, aryl$_{(C≤30)}$, aralkyl$_{(C≤30)}$, heteroaryl$_{(C≤30)}$, heteroaralkyl$_{(C≤30)}$, or a substituted version of any of these groups.

Preferably, the cationic detergent is an ammonium cationic surfactant with functional groups that tether the alkyl chains, saturated or unsaturated, rings or aryl groups to the central nitrogen by means of an ether, thioether, ester, or amide. However, all cationic detergents that involve a heterocyclic ring structure, such as imidazole or pyridine, are contemplated as alternative embodiments of the invention.

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means NH$_2$; "hydroxyamino" means —NHOH; "nitro" means —NO$_2$; imino means=NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means=S; "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "====" represents a single bond or a double bond. Thus, for example, the structure

includes the structures

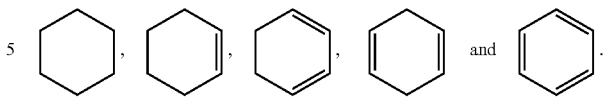

As will be understood by a person of skill in the art, no one such ring atom forms part of more than one double bond. The symbol "〜〜", when drawn perpendicularly across a bond indicates a point of attachment of the group. It is noted that the point of attachment is typically only identified in this manner for larger groups in order to assist the reader in unambiguously identifying a point of attachment. The symbol "◄" means a single bond where the group attached to the thick end of the wedge is "out of the page." The symbol "⦀⦀" means a single bond where the group attached to the thick end of the wedge is "into the page". The symbol "〜〜" means a single bond where the conformation (e.g., either R or S) or the geometry is undefined (e.g., either E or Z). Similarly, the covalent bond symbol "—", when connecting stereogenic atom, does not indicate any preferred stereochemistry, it does cover all stereoisomers, including the "◄" and "⦀⦀" forms.

Any undefined valency on an atom of a structure shown in this application implicitly represents a hydrogen atom bonded to the atom. A bold dot on a carbon atom indicates that the hydrogen attached to that carbon is oriented out of the plane of the paper. When a group "R" is depicted as a "floating group" on a ring system, for example, in the formula:

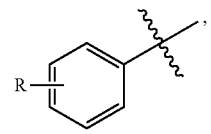

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

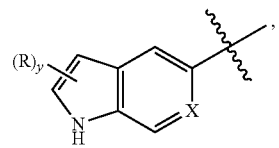

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "saturated" as used herein means the compound or group so modified has no carbon-carbon double and no carbon-carbon triple bonds, except as noted below. The term does not preclude carbon-heteroatom multiple bonds, for example carbon oxygen double bonds or a carbon nitrogen double bonds. Moreover, it does not preclude a carbon-carbon double bond that may occur as part of keto-enol tautomerism or imine/enamine tautomerism.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl). Where the term "aliphatic" is used without the "substituted" modifier, then only carbon and hydrogen atoms are present. When the term is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups —CH$_3$ (Me), —CH$_2$CH$_3$ (Et), CH$_2$CH$_2$CH$_3$ (n-Pr or propyl), —CH(CH$_3$)$_2$ (i-Pr, $^i$Pr or isopropyl), —CH(CH$_2$)$_2$ (cyclopropyl), CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$—(methylene), —CH$_2$CH$_2$—, —CH$_2$C(CH$_3$)$_2$CH$_2$—, —CH$_2$CH$_2$CH$_2$—, and

are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting example of a haloalkyl. An "alkane" refers to the compound H—R, wherein R is alkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups. An "alkane" refers to the compound H—R, wherein R is alkyl.

The term "alkenyl" when used without the "substituted" modifier refers to an monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

are non-limiting examples of alkenediyl groups. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —CH=CHF, —CH=CHCl and —CH=CHBr, are non-limiting examples of substituted alkenyl groups. An "alkene" refers to the compound H—R, wherein R is alkenyl.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH$_3$, and —CH$_2$C≡CCH$_3$, are non-limiting examples of alkynyl groups. When alkynyl is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. An "alkyne" refers to the compound H—R, wherein R is alkynyl.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl group (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and the monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of arenediyl groups include:

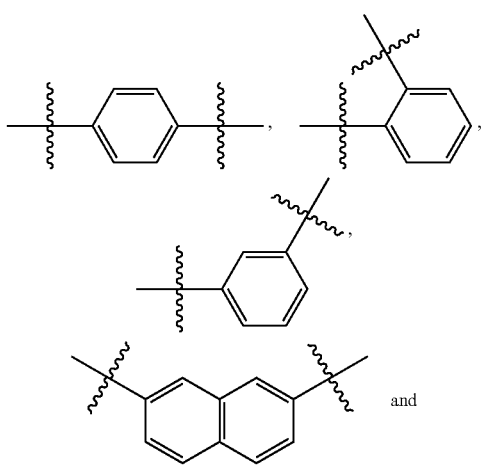

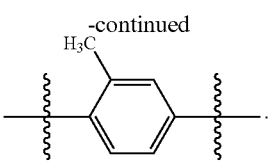

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. An "arene" refers to the compound H—R, wherein R is aryl. Benzene and toluene are non-limiting examples of arenes.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term is used with the "substituted" modifier one or more hydrogen atom from the alkanediyl and/or the aryl has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroarenediyl groups include:

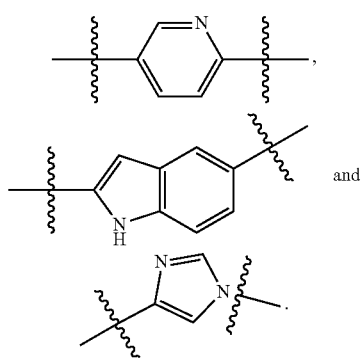

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "alkoxy" when used without the "substituted" modifier refers to the group —OR, in which R is an alkyl, as that term is defined above. Non-limiting examples of alkoxy groups include: —OCH$_3$ (methoxy), —OCH$_2$CH$_3$ (ethoxy), —OCH$_2$CH$_2$CH$_3$, —OCH(CH$_3$)$_2$ (isopropoxy), —O(CH$_3$)$_3$ (tert-butoxy), —OCH(CH$_2$)$_2$, —O-cyclopentyl, and —O-cyclohexyl. The terms "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is alkenyl, alkynyl, aryl, aralkyl, heteroaryl, heterocycloalkyl, and acyl, respectively. The term "alkoxydiyl" refers to the divalent group —O— alkanediyl-, —O— alkanediyl-O—, or -alkanediyl-O-alkanediyl-. The term "alkylthio" and "acylthio" when used without the "substituted" modifier refers to the group —SR, in which R is an alkyl and acyl, respectively. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The term "alcohol" corresponds to an alkane, as defined above, wherein at least one of the hydrogen atoms has been replaced with a hydroxy group. Similarly, the term "ether" corresponds to an alkane, as defined above wherein at least one of the hydrogen atoms has been replaced with an alkoxy group.

IV. RELATIONSHIP BETWEEN THE TYPE OF SALT AND THE TYPE OF DETERGENT USED

Variable results are observed for each unique cationic detergent examined in embodiments of this invention indicating that one cannot predict a particular phase separating agent (e.g. cationic detergent) nucleic capture properties simply based upon the fact that it contains a cation with a hydrophobic tail. Each cationic detergent behaves differently as indicated by the results provided in the Examples. Moreover, the cationic surfactants not only interact differently with the nucleic acids, but they also are strongly and uniquely affected by the salts and buffering components added to the solution. Both the cation and the anion play unique and unexpected roles in how the surfactants bind nucleic acids (see, e.g. Example 6). A preferred molecule, domiphen bromide, possesses the unique property of tunability. Tunability is the ability to control of the size of the nucleic acids phased separated by the surfactant-nucleic acid complex by varying conditions including but not limited to salts, pH, and other surfactants both ionic and non-ionic in the solution. This tunability of domiphen bromide allowed for highly efficient removal of small contaminating nucleic acids such as RNA. Domiphen bromide (DB) also possessed the interesting property of providing for enhanced (i.e. a boost) in recovery after a treatment with a salt wash after capturing the DB-NA complex with a mineral matrix such as glass fibers.

Specifically, acetates and citrates drastically change the phase separation and capture properties of domiphen bromide. DB, unlike CTAB, MTAB, cetylpyridinium bromide, etc., showed no affinity for the small nucleic acids, such as the degraded RNA commonly found in plasmid isolation that includes RNAse A. However, in the presence of the potassium acetate, which is commonly used in the neutralization buffer, small nucleic acids were bound and recovered. Capturing such small RNA species is undesirable since RNA is a contaminant for plasmid DNA isolation.

To rescue DB's ability to selectively bind the larger nucleic acids, the conditions in the phase separation solution had to be tuned, referred to herein as tunability. A reduced concentration of potassium acetate in the neutralization buffer and high concentrations of Bis-Tris or Tris in the phase separation buffer was necessary (about 0.8 to about 1.1 M Bis-Tris or Tris) along with an adjustment of the concentration of lithium chloride to about 0.4-1.8 M. The original concentrations of potassium acetate used varied in the range of about 1.0-3 M. This translates to a final concentration (M) of about 0.1 M-0.45M LiCl and about 0.275M Bis-Tris or Tris and a range of about 0.25M-1M potassium acetate used for the same solution. Reducing the potassium acetate concentration alone was not as effective at rescuing DB's selectivity. However, under the preferred conditions, the DB-based phase separation buffer became more effective at selecting for larger nucleic acids than CTAB-containing buffer. This highly desirable and surprising rescue of high purity plasmid capture was derived from DBs unique tunability which allows for selective capture of nucleic acid species.

In the case of CTAB the buffer alone was not effective at providing size selective capture of only the desired nucleic acid, a salt wash was required for the effective removal of degraded RNA (U.S. Pat. App. 2008/0113348 and U.S. Pat. No. 8,679,744). However, the first wash buffer, which uses salts to remove weakly interacting nucleic acids, was not sufficient in the DB-based system to remove the degraded RNA as no removal was observed (See Example 18). Instead a treatment solution containing salts such as sodium chloride or lithium chloride in the range of 0.1-0.7 M (e.g. 0.1M, 0.2M, 0.3M, 0.4M, 0.5M, 0.6M, and 0.7M) enhanced the retention of nucleic acids acting as a significant boost to recovery yields. This is contrary to the popular surfactant CTAB and similar cationic surfactants as disclosed by Thorsten Singer, where it is indicated that a special wash buffer is required to remove contaminating RNA to obtain the additional selectivity required to clean the sample. DB attains this selectivity for nucleic acid capture solely within the phase separation buffer and does not require a wash to remove contaminating RNA. The selective phase separation/capture properties for DB effectively removes unwanted nucleic acid species (i.e. degraded RNA in a plasmid preparation). Such RNA species are simply not captured to the matrix.

In the case of Tris-HCl, substitution of Tris-HCl for Bis-Tris (control) for shifts the preferred LiCl concentration of Domiphen Bromide capture pf plasmid DNA. Preferred LiCl concentration of between about 0.6 M to about 1.05M with about 0.7M, about 0.8 M, about 0.9M and about 1.0M LiCl being preferred with a Tris-HCL based capture buffer.

V. DEFINITIONS

As used herein, the term "Capture" means both adsorption and absorption and further includes but is not limited to trapping of phase separated nucleic acid-cationic surfactant complexes by a Solid Support Carrier (e.g., a mineral matrix).

As used herein, the term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. For example, the present invention includes chimeric DNA molecules that comprise a DNA sequence and a heterologous DNA sequence which is not part of the DNA sequence. A heterologous expression regulatory element is such an element that is operatively associated with a different gene than the one it is operatively associated with in nature. In the context of the present invention, a gene encoding a protein of interest is heterologous to the vector DNA in which it is inserted for cloning or expression, and it is heterologous to a host cell containing such a vector, in which it is expressed.

As used herein, the term "isolated" means that the referenced material is removed from the environment in which it is normally found. Thus, an isolated biological material can be free of cellular components, i.e., components of the cells in which the material is found or produced. Isolated nucleic acid molecules include, for example, genomic DNA, a PCR product, RNA including an isolated mRNA, a cDNA, or a restriction fragment. Isolated nucleic acid molecules also include, for example, sequences inserted into plasmids, cosmids, artificial chromosomes, and the like. An isolated nucleic acid molecule is preferably excised from the genome in which it may be found, and more preferably is no longer joined to non-regulatory sequences, non-coding sequences, or to other genes located upstream or downstream of the nucleic acid molecule when found within the genome. An isolated protein may be associated with other proteins or nucleic acids, or both, with which it associates in the cell, or with cellular membranes if it is a membrane-associated protein.

As used herein, "Plasmid" includes but is not limited to plasmids, cosmids, phage vectors, expression vectors, viral vectors, yeast shuttle vectors, and yeast artificial chromosomes. Reference to Plasmids includes constructs or vectors of the present invention that may comprise DNA sequences that facilitate the cloning and propagation of the DNA including but not limited to DNA other than that of the host organism (i.e. often heterologous DNA). A large number of plasmids vectors, including bacterial and fungal shuttle vectors, have been described for replication and/or expression in a variety of eukaryotic and prokaryotic host cells and are encompassed by this definition.

As used herein, "Selectivity" means the ability to bind nucleic acids based on size anf type of the nucleic acid, for example by binding genomic DNA or plasmid DNAs, preferentially over RNA and or degraded RNA using phase separation reagents.

As used herein, "Tunability" means the ability to control the size selection of the phase separation reagent by varying conditions including but not limited to salts, pH, and other surfactants both ionic and non-ionic in the solution.

As used herein, "Solid Support Carrier" means mineral matrices that could be implemented with embodiments of the present invention and include porous or non/porous carrier composed of metal oxides and mix metal oxides. Such metal oxides include materials commonly used in the art such as silicon-oxygen based compounds. Borosilicate or silicate in the form of glass fibers, silica gel, zeolites, or diatomaceous earth are most commonly used due their inexpensive and non-toxic properties, however other minerals such as aluminum oxide, titanium dioxide, zirconium dioxide or mixtures thereof are included in this term as alternative embodiments.

As used herein, "Prepared Sample" means a sample prior to the isolation of nucleic acid therefrom (e.g. Plasmid via a solid support carrier) comprising the final concentration of each constituent present, including but not limited to cationic surfactants, salt solutions, buffers or other constituents known in the art or disclosed herein. The final concentration of each constituent in a Prepared Sample can be measured by any standard analytical technique including commonly used metrics including but not limited to molarity (M), molality (m), volume to volume (v/v) percentage, weight to volume (w/v) percentage, and weight to weight (w/w) percentage.

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Titration of NaCl with 1-decyl-3-methylimidazolium chloride (DMIC)

A solution of plasmid DNA (pDNA) and degraded RNA was used to test the ability of 1-decyl-3-methylimidazolium chloride (DMIC) to selectively bind DNA in the presence of varying concentrations of salt. The plasmid DNA used was pGEM, which is a 3.2 kb plasmid. The degraded DNA used was RNA digested with RNAse A, which runs as a smear below the 1 kb ladder on an agarose gel.

A TE solution (50 mM Tris-HCl pH 8.0/10 mM EDTA) containing pDNA and RNAse A degraded RNA was mixed with P4. The P4 solution (1% DMIC with titration of 0-2M NaCl) was added to the aqueous solution containing the pDNA and degraded RNA and mixed thoroughly by inversion (1 ml of P4 was added for every 3 ml of sample volume). The sample was subsequently loaded onto a glass fiber matrix in a spin column, and the captured nucleic acids were washed with 700 µl 0.5 M NaCl/80 mM Tris pH 8.5/0.5 mM EDTA and subsequently washed with 700 µl 95% ethanol. Finally, the nucleic acids were eluted from the glass fiber matrix using a microcentrifuge. Each reaction was visualized by agarose gel electrophoresis at 5 min as an RNA check and again at 45 min to evaluate the full-length run (FIGS. 1A-B). Under these conditions, the DMIC selectively captured the larger DNA and removed the degraded RNA.

Example 2—Titration of NaCl with 1,3-didecyl-2-methylimidazolium chloride (DDMIC)

A solution of plasmid DNA (pDNA) and degraded RNA was used to test the ability of 1,3-didecyl-2-methylimidazolium chloride (DDMIC) to selectively bind DNA in the presence of varying concentrations of salt. The plasmid DNA used was pGEM, which is a 3.2 kb plasmid. The degraded DNA used was RNA digested with RNAse A, which runs as a smear below the 1 kb ladder on an agarose gel.

Figure 2:
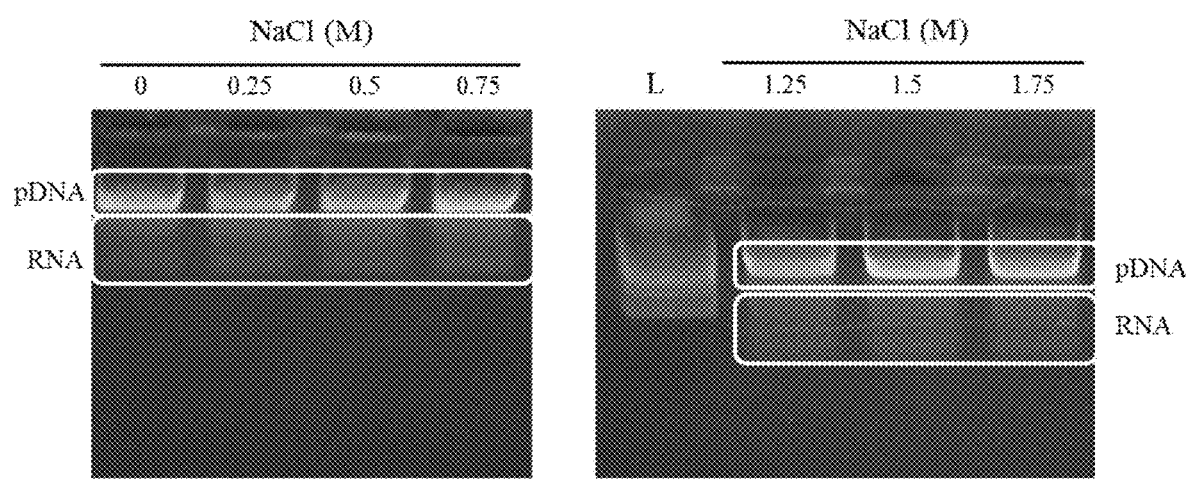
FIG. 2—Titration of NaCl with 1,3-didecyl-2-methylimidazolium chloride. Agarose gel electrophoresis of a solution of pDNA/degraded RNA purified using a sodium chloride titration with 1,3-di decyl-2-methylimidazolium chloride. Each lane is labeled with the concentration of NaCl (M). L=1 kb ladder. pDNA=plasmid DNA. RNA=degraded RNA. Gels were electrophoresed for 5 minutes as an RNA check.

A TE solution (50 mM Tris-HCl pH 8.0/10 mM EDTA) containing pDNA and RNAse A degraded RNA was mixed with P4. The P4 solution (1% DDMIC with titration of 0-2M NaCl) was added to the aqueous solution containing the pDNA and degraded RNA and mixed thoroughly by inversion. (1 ml of P4 was added for every 3 ml of sample volume.) Next, P4 buffer (1% didecylimidazole with titration of 0-2 M NaCl) was added to the cleared solution and mixed thoroughly by inversion. After loading the solution onto a glass fiber matrix in a spin column, the solution was washed with 700 µl 0.5 M NaCl/80 mM Tris pH 8.5/0.5 mM EDTA and then washed with 700 µl 95% ethanol. Finally, the nucleic acid was eluted from the glass fiber matrix. Each reaction was visualized by agarose gel electrophoresis at 5 min to check for the presence of degraded RNA (FIG. 2).

1,3-Didecyl-2-methylimidazolium chloride successfully captured plasmid DNA; however, it did not selectively remove degraded RNA as NaCl was titrated into the buffer. After 1.75 M NaCl, this solution began to phase separate before being adding to the the sample. Therefore, 1.75 M NaCl was as high as this buffer could be titrated using NaCl. Other salts could potentially be used to further tune the selectivity of this phase separation reagent, but for the purpose of this initial examination only NaCl was investigated.

Example 3—Titration of NaCl with Cetylpyridinium Bromide (CPB)

A solution of Cetylpyridinium bromide (CPB) was evaluated with increasing concentrations of sodium chloride to determine the optimal concentrations of the salt and phase separation reagent for selective capture of plasmid DNA while removing degraded RNA. For this, a culture containing JM109 transformed with pGEM was grown overnight for 16 hours. The cells contained in 35 ml of culture were pelleted and suspended in 5 ml P1 buffer. The cells were then lysed using 5 ml P2 buffer for 3 minutes and the solution was neutralized and genomic DNA/proteins were precipitated using 5 ml P3 buffer that contained 1.5 M potassium acetate at about a pH 4.9. The precipitated cellular debris were cleared by using a glass fiber filter. 5 ml P4 buffer (0.25%-1% CPB with titration of 0-1.75 M NaCl) was added prior to loading the solution onto a glass fiber matrix in a spin column. The matrix was washed with 700 µl 0.5 M NaCl/80 mM Tris pH 8.5/0.5 mM EDTA and then washed with 700 µl of 95% ethanol. Finally, the captured nucleic acid was eluted. Each reaction was visualized by agarose gel electrophoresis at 5 min to check for the presence of degraded RNA (FIGS. 3A-D).

By varying the w/v % of CPB from 0.25%-1% while titrating NaCl from 0-1.75 M, it was found that the degraded RNA found below the lowest band of the 1 kb ladder was not completely removed using NaCl alone. Cetylpyridinium surfactants have the unique property of having very little tunability or selectivity even in the presence of many different salts, surfactants or buffer conditions. These molecules tend to form Surfactant-NA complexes very strongly with all sizes of nucleic acids despite the conditions and for this reason these molecules may be interesting for the precipitation or capture of cell free DNAs, microRNAs, or other smaller nucleic acids to a mineral matrix.

Example 4—Titration of NaCl with Decylpyridinium Chloride (DPC)

A solution of decylpyridinium chloride (DPC) was evaluated with increasing concentrations of sodium chloride to determine the optimal concentrations of the salt and phase separation reagent for selective capture of plasmid DNA while removing degraded RNA For this, JM109 cells transformed with pGEM were grown overnight for 16 hours. The cells contained in 35 ml of culture were pelleted and suspended in 5 ml P1 buffer. The cells were then lysed using 5 ml P2 buffer for 3 minutes and the solution was neutralized and genomic DNA/proteins were precipitated using a 5 ml P3 buffer that contained 1.5 M potassium acetate about pH 4.9 and 200 µg/ml RNAse A. The precipitated cellular debris were cleared by using a glass fiber filter. 5 ml P4 buffer (1% DPC with titration of 0-2 M NaCl) was added and mixed thoroughly prior to loading the solution onto a glass fiber matrix. The matrix was washed with 700 µl 0.5 M NaCl/80 mM Tris pH 8.5/0.5 mM EDTA and then washed with 700₁1.195% ethanol. Finally, the captured nucleic acid was eluted. Each reaction was visualized by agarose gel electrophoresis at 5 min as to check for the presence of degraded RNA again at 45 min to evaluate overall quality (FIGS. 4A-B).

DPC behaved similarly to cetylpyridinium bromide in that it does not appear to remove degraded RNA with a simple salt titration; however it has exceptionally improved solubility. The pyridinium salts as a class appear to efficiently provide for the recovery of nucleic acids with very limited or no ability to select for size. This indicates that the utility of each phase separation reagent is highly dependent on the goals of the purification and that these reagents do not follow the trends at all that have been observed for binding and other properties some of the commonly used cationic surfactants (e.g. CTAB).

Example 5—Titration of NaCl and LiCl with Domiphen Bromide (DB)

Nucleic acids in solution. A solution of plasmid DNA (pDNA) and degraded RNA was used to test the ability of domiphen bromide (DB) to selectively bind DNA in the presence of varying concentrations of salt. The plasmid DNA used was pGEM, which is a 3.2 kb plasmid. The degraded RNA used was RNA digested with RNAse A, which runs as a smear below the 1 kb ladder on an agarose gel.

A TE solution (50 mM Tris-HCl pH 8.0/10 mM EDTA) containing pDNA and RNAse A degraded RNA was mixed with P4. The P4 solution (1% DB with titration of 0-3M NaCl and 0-3.75M LiCl) was added to the aqueous solution containing the pDNA and degraded RNA and mixed thoroughly by inversion (1 ml of P4 was added for every 3 ml of sample volume). The sample was subsequently loaded onto a glass fiber matrix in a spin column, and the captured nucleic acids were washed with 700 µl 0.5 M NaCl/80 mM Tris pH 8.5/0.5 mM EDTA and finally washed with 700 µl 95% ethanol. Finally, the nucleic acid was eluted from the glass fiber matrix. Each reaction was visualized by agarose gel electrophoresis at 5 min to check for the presence of degraded RNA and again at 45 min to evaluate the overall quality.

The results from these experiments using DB to isolate plasmid DNA (FIGS. 5A-E) indicated that DB very effectively precipitates and selectively binds large nucleic acids to the glass fiber matrix. The results showed high recovery and greater selectivity and tunability by isolating preferred sized large nucleic acids (i.e. plasmids) over small nucleic acids (i.e. RNA species) compared to an optimized system that uses CTAB. DB also showed capture of large sized nucleic acids (plasmid) was linearly affected by increasing salt concentration. These results indicate that alkyl surfactants such as CTAB do not behave similarly to the functionalized or heterocyclic phase separation reagents discussed herein. It was highly unexpected that the phase separation reagents showed unique and distinct differences in nucleic acid capture characteristics depending on the particular reagent chosen. The behavior of each phase separation reagent cannot be predicted based upon the information currently available due to structure alone. For example some surfactants such as cetlypyridinium bromide show little selectivity and capture all nucleic acids exceptionally well.

Notably, the amount of pDNA recovered increased with increasing concentrations of salt (both NaCl and LiCl) indicating the DB-NA complex was enhanced by the ionic strength of the solution. When sodium chloride was titrated into the phase separation buffer indicated in the publication (US2008/01223348 A1), increased concentrations of salt actually decreased total capture of nucleic acids. Domiphen bromide-NA complexes were weakened only after ionic strength of the solution disrupted the interaction in its entirety.

Bacterial Culture.

A solution of DB was evaluated with increasing concentrations of lithium chloride to determine how DB behaves in the context of a plasmid isolation using alkaline lysis. For this, JM109 cells transformed with pGEM were grown overnight for 16 hours. The cells contained within 35 ml of culture were pelleted and suspended in 5 ml P1 buffer. The cells were then lysed using 5 ml P2 buffer for 3 minutes and the solution was neutralized and genomic DNA/proteins were precipitated using a 5 ml P3 buffer that contained 1.5 M potassium acetate at about pH 4.9 and 200 µg/ml RNAse A. The precipitated cellular debris was cleared by using a glass fiber filter. 5 ml P4 buffer (1% DB with titration of either 1-2.75 M LiCl and subsequently narrowly with 1.55-1.7M LiCl) was added prior to loading the solution onto a glass fiber matrix. The matrix was washed with 700 µl 0.65 M LiCl and then washed with 700 µl 95% ethanol. Finally, the captured nucleic acid was eluted. Each reaction was visualized by agarose gel electrophoresis at 5 min as to check for the presence of RNA and again at 45 min to evaluate the full-length run (FIGS. 6A-D). See Table 1 for the quantification of plasmid DNA recovered for the titration of 1.55-1.7M LiCl. The range of LiCl concentration present in the phase separation buffer translates to final concentration (M) range of about 0.3875M-0.425M LiCl in the prepared sample.

Under the conditions of typical alkaline lysis, isolation of plasmid DNA from bacterial culture is very different than that of pure water or a TE solution. After clearing the cell debris, the solution that remains contains primarily potassium acetate, pH 5.5, DNA, degraded RNA, and residual proteins or other debris that do not precipitate after the SDS precipitation. Interestingly, nucleic acid recovery was enhanced using this system as compared to a simplified example previously discussed. However DB appeared to have lost its ability to selectively bind large nucleic acids over small nucleic acids such as degraded RNA. Upon, addition of lithium chloride the selectivity of the system was partly restored where plasmid DNA was preferentially captured over degraded RNA. However it appeared that lithium chloride alone in the presence of a cleared lysate was not sufficient to prevent the smaller fragments of degraded RNA from being copurified without the further tuning of the phase separation buffer, as small amounts of degraded RNA appeared to be retained. Lithium chloride facilitated enrichment of plasmid DNA over degraded RNA, but it did not restore the selective properties observed when using DB. Furthermore, as if the sample was not processed immediately after the addition of DB theDB-RNA interactions became more pronounced indicating the interaction was not completely inhibited under these conditions. (Data not shown). Without being bound to a particular theory it was believed that the potassium acetate caused the dramatic change in the capture profile of domiphen bromide (See example 6).

TABLE 1

Domiphen bromide/LiCl titration from cleared lysate

| Treatment Group | [pDNA] (ng/µL) | Avg. [pDNA] | Std Dev |
|---|---|---|---|
| 1.5M LiCl | 591.8 | 663.1 | 100.83 |
| 1.5M LiCl | 734.4 | | |
| 1.55M LiCl | 761.95 | 676.77 | 120.47 |
| 1.55M LiCl | 591.58 | | |
| 1.6M LiCl | 542.89 | 556.39 | 19.08 |
| 1.6M LiCl | 569.88 | | |
| 1.65M LiCl | 445.47 | 514.17 | 97.16 |
| 1.65M LiCl | 582.87 | | |
| 1.7M LiCl | 699.85 | 575.43 | 175.96 |
| 1.7M LiCl | 451.01 | | |
| 1.75M LiCl | 393 | 387.15 | 8.27 |
| 1.75M LiCl | 381.3 | | |

Yield Boosting Treatment Buffer Optimization.

Figure 6E:
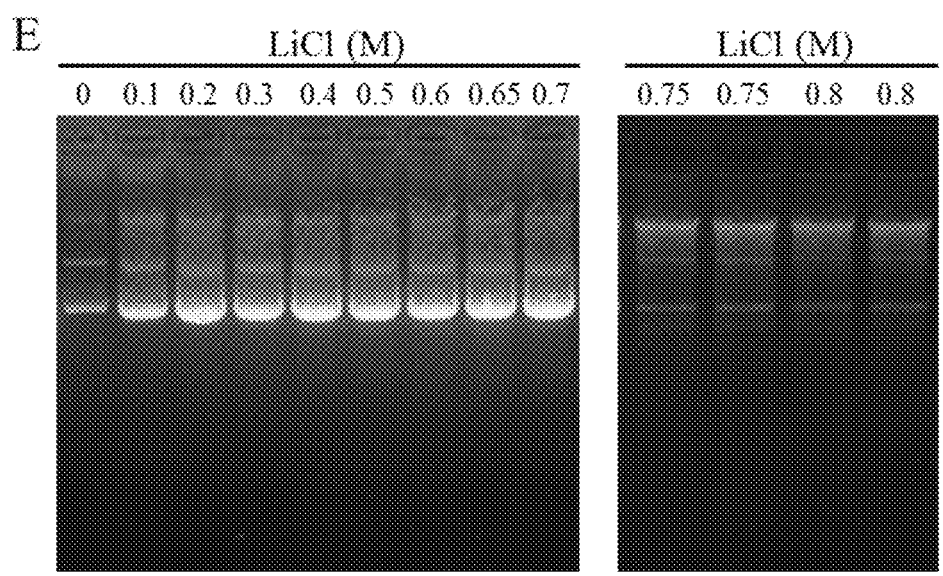
FIGS. 6A-B; 6C-D; and 6E—Titration of LiCl with domiphen bromide using bacterial cultures. (A-D) Agarose gel electrophoresis of nucleic acid samples purified from bacterial culture using a lithium chloride titration of DB. Each lane is labeled with the concentration of LiCl (M).

An experiment was performed to determine the preferred salt concentration in the treatment solution with respect to increasing retention of plasmid and thus overall yield. The salt concentration used strongly affected the total plasmid recovered as indicated in FIG. 6E. Note that at 0 M LiCl the intensity of the plasmid is greatly reduced (lower yield), however upon the addition of even 0.1 M LiCl there is a substantial boost in the recovery of plasmid. As the concentration of salt in this treatment buffer was increased the boost in retention and recovery of the captured nucleic acid increased until at which point the ionic strength of the solution disrupted the phase separation reagent nucleic acid complex and washed away the nucleic acid The presence of salt in this treatment greatly increased the retention and recovery of plasmid in comparison to just a treatment containing water only or skipping the treatment and only performing the organic wash step. This titration indicated that 0.7 M LiCl corresponded to the highest recovery of plasmid examined. However, after 0.7 M LiCl the plasmid recovery was drastically reduced, which is likely due to the disruption of the interaction between the phosphate backbone of the nucleic acids and the phase separation reagent. Common inorganic salts such as sodium chloride could also be used to boost the retention and recovery of the target nucleic acid(s) being isolated. The preferred range of salt solution depends on the salt used however the range of salt concentration that could be used lies between about 0.1M and about 1.0M LiCl, NaCl, or KCl. More specifically the preferred range is between about 0.35 and about 0.55M LiCL, NaCl, or KCl.

The original intent of adding salts in the first treatment solution was to remove molecules that weakly interact with the domiphen bromide, however as one can see it had the unexpected result of also greatly increasing the recovery of the plasmid DNA. In contrast a similar solution applied to a nucleic acid/plasmid isolation system with CTAB (Application US2008/0113348) was used to remove RNA contamination however their results indicate no increase in overall nucleic acid yield including genomic DNA and plasmid DNA yield. In the CTAB system the recovery of total nucleic acids decreased with increasing concentrations of salt. However we found by using domiphen bromide as the phase separation/capture agent, there was unexpectedly a dramatic increase in recovery of large fragments that increased with increasing salt concentration in this treatment step and no visible change in capture of small nucleic acids such as degraded RNA. There was a point at which overall recovery was diminished due to salt likely interfering with the DB-Nucleic Acid-Borosilicate matrix interactions; however within the range of about 0.1-0.7 M there was a significant improvement in recovery versus no salt buffer solution treatment. The salt treatment used in the DB system had the unique property of increasing retention of nucleic acid thus boosting the yield in addition to the originally intended contaminant removal, which further exemplifies the unexpected nature of these phase separation reagents especially functionalized and heterocyclic ammonium surfactants.

Example 6—Evaluation of Various Salts for their Effect on Total Recovery and Selectivity of Nucleic Acids Recovered Using Domiphen Bromide (DB)

Various salts were evaluated to determine how the affect total recovery and selectivity of domiphen bromide in the context of plasmid preps based on alkaline lysis. For this experiment, JM109 was transformed with pGEM and cultures were grown overnight for about 16 hours. The cells contained within 35 ml of culture were pelleted and suspended in 5 ml P1 buffer. The cells were then lysed using 5 ml P2 buffer for 3 minutes and the solution was neutralized and genomic DNA/proteins were precipitated using a 5 ml P3 buffer that contained 1.0 M potassium acetate pH 4.9 and 200 µg/ml RNAse A. The precipitated cellular debris was cleared by using a glass fiber filter. 5 ml P4, a 1% domiphen bromide solution containing varying concentration of salts, was added to the cleared lysate prior to loading the solution onto a glass fiber matrix. The matrix was washed with 700 µl 0.6 M LiCl and then washed with 700 µl 95% ethanol. Finally, the captured nucleic acid was eluted using water.

The following salts were investigated for their effects on selectivity and total recovery: sodium citrate (0.25-1 M; FIGS. 7C-D), lithium bromide (0.5-1 M), lithium acetate (1-2.25 M; FIGS. 7A-B), magnesium chloride (0.1-1.25 M; FIGS. 7A-B), sodium formate (1-2.25 M; FIGS. 7C-D), potassium acetate (1-2.25 M; FIGS. 7E-F), potassium chloride (1-2.25 M; FIGS. 7E-F), and sodium acetate (1-2.25 M; FIGS. 7E-F). Each reaction was visualized by agarose gel electrophoresis at 5 min to check for the presence of degraded RNA and again at 45 min to evaluate the full-length run.

The results indicated that potassium chloride, magnesium chloride, and sodium formate were able to selectively recover plasmid DNA. Lithium bromide caused the phase separation reagent, domiphen bromide, to precipitate immediately and was therefore not used.

The lithium acetate and sodium citrate did not increase the selectivity of the phase separation reagent for large nucleic acids as indicated by the presence of degraded RNA at concentrations up to 2.25 M lithium acetate.

By qualitative examination of the gel electrophoresis results the increased potassium acetate appeared to slowly mitigate small nucleic acids from being recovered; however, it began to cause the buffer to precipitate at concentrations higher than 2 M KoAc and was therefore removed from consideration. Without being bound to a particular theory it is believed that that slow decrease in recovery of degraded RNA was based on the potassium cation as potassium chloride facilitated removal of small fragments.

The above salts are functional in that they allowed capture and some of the salts even enhanced capture (e.g., sodium acetate). However, none of the salts added appeared to facilitate a large degree of size selection, and therefore, were deemed suboptimal. Both the cation and the anion in these salts directly affect what and how much is captured. For instance, the acetate ion favored capture of all nucleic acids, as indicated by the difference in selectivity for large DNA between potassium chloride and potassium acetate. Domiphen bromide in solution-based experiments that did not contain potassium acetate showed no capture of small nucleic acids, such as degraded RNA (See example 4).

Example 7—Evaluation of the Effect of pH and Salt Effect on Capture Capacity and RNA Elimination while Using 1 M KoAc and Domiphen Bromide (DB)

The purpose of the following experiment was to determine the effect of pH on the capture of nucleic acids from a cleared lysate using domiphen bromide (DB). The interest was to examine changes in both total recovery and selective recovery of specific sized nucleic acids.

For this experiment, JM109 was transformed with pGEM and cultures were grown overnight for 16 hours. The cells contained within 35 ml of culture were pelleted and suspended in 5 ml P1 buffer. The cells were then lysed using 5 ml P2 buffer for 3 minutes and the solution was neutralized and genomic DNA/proteins were precipitated using a 5 ml P3 buffer that contained 1.0 M potassium acetate pH 4.9 and 200 µg/ml RNAse A. The precipitated cellular debris was cleared by using a glass fiber filter. 5 ml P4, a 1% domiphen bromide solution containing varying concentration of salts, Bis-Tris or Tris to control the pH, and or N-Lauroylsarcosine sodium salt to see the effect of using an anionic detergent, was added to the cleared lysate prior to loading the solution onto a glass fiber matrix to capture the nucleic acids. The matrix was washed with 700 µl 0.6 M LiCl and then washed with 700 µl 95% ethanol. Finally, the captured nucleic acid was eluted.

All the phase separation buffers were titrated with lithium chloride to determine the effect of pH or N-Laurylsarcosine sodium salt had on recovery or selective recovery of nucleic acids. Four different buffers were tested: (1) 1.1 M Tris pH 8.5, 0.5-1.75 M LiCl, 1% DB (FIGS. 8A-B); (2) 1.1 M Bis-Tris pH 7.0, 0.5-1.75 M LiCl, 1% DB (FIGS. 8A-B); (3)

1.5-2.25 M LiCl, 1% DB (FIGS. 8A-B); and (4) 1.5 M LiCl, 0.01-0.25% (w/v) N-Lauroylsarcosine, 1% DB (FIGS. 8C-D). Each reaction was visualized by agarose gel electrophoresis at 5 min to check for the presence of degraded RNA and again at 45 min to evaluate the full-length run.

Without being bound to a particular theory it is thought that the salts that composed the buffer played an equally important role as the effect of pH on controlling DB's selectivity for capture of large nucleic acids over small nucleic acids such as degraded RNA. It is interesting that the effect of pH on DB's ability to size select behaves exactly opposite to reports on CTAB behavior ((U.S. Pat. App. 2008/0113348). This result was unexpected and further demonstrates the unpredictable and highly tunable nature of the functionalized and heterocyclic ammonium surfactants such as DB.

Selective Capture Window.

Without being bound to a particular theory it is thought that the DB based cationic surfactant-nucleic acid complex is facilitated to some extent by the presence of salts and chemicals (e.g. buffers). The formation of the micelle is facilitated by an increase in ionic strength of the solution, however there is a point as which the salt concentration begins to strongly interfere with the cationic surfactant-nucleic acid complex. Which means that in the case of the "tunable" surfactants, show this behavior, it was found that there is a "window" of opportunity where one can select for the nucleic acid size that is desirable, remove contaminants, and maximize total recovery due to facilitating micelle formation. DB, being a highly tunable surfactant allowed for selection to take place under the conditions of salt/pH discussed in this experiment. The results of this experiment indicate that adjusting the pH using Bis-Tris and Tris did not dramatically change the total recovery of nucleic acid; however, it did affect the selectivity. These changes in pH and the addition of Bis-Tris/Tris salts affected the "window" (FIGS. 8A-D, circled concentrations) in which the small nucleic acid fragments were selectively removed. Note that the "window" in which the degraded RNA is absent is much larger in the solutions containing Tris and Bis-Tris as compared to the control solution that contained varying concentrations of LiCl buffered by KoAc at pH 4.9. This increase in the "window" of opportunity for selective plasmid isolation is a key component to designing a kit for the isolation of pure plasmid DNA. It should be noted that the effect of pH from salts and chemical (e.g. buffers) is unpredictable since Bis-Tris and Tris although similar are quite different molecules, and both similarly affected the selectivity but at different salt concentrations.

N-Lauroylsarcosine sodium salt also contributed to selectivity in that it showed a propensity to remove smaller nucleic acids; however, the system is very sensitive to small changes in N-Lauroylsarcosine sodium salt concentration and therefore would not be an ideal candidate for aiding selectivity. It also appeared to enhance total recovery at 0.1% (w/v) N-Lauroylsarcosine sodium salt. This translates to a final concentration (w/v) of 0.025% (w/v) N-Lauroylsarcosine sodium salt. The conditions that showed the most promise were titrated further (see, Example 8).

There are two principle nucleic acid types that must be removed when creating a plasmid isolation kit. The first is genomic DNA, which is classically removed during the SDS/KoAc precipitation step, and RNA, which is digested by RNAse A. However, the RNAse does not completely remove the RNA, it simply digests it into smaller fragments that range in size from about 1-100 bp. Therefore, in order to create a kit that is free of nucleic acid contaminants, the selective removal of small nucleic acids from the plasmid prep is fundamental to its design.

Endotoxin Removal.

The wide range of selective capture provided by this method for large nucleic acids preferentially over small parallels another key feature of plasmid isolation method—endotoxin removal. Other compounds that have weaker affinity for the cationic surfactant could also be selectively removed. This means that endotoxins are expected to be selectively removed by the "Phase separation solution" if the proper ratio of salts and the correct pH is achieved (see, circled concentrations). Therefore, contamination could be problematic if the system is not robustly buffered against slight changes in volumes due to user handling or changes in volume of cleared lysate recovered post filtration.

The plasmid pGEM was isolated from 100 ml of a JM109 E. coli culture grown overnight and the average EU/µg of plasmid DNA for the preps was 0.985 when measured using the Pyrochrome Endotoxin Specific Assay (Associates of Cape Cod, Inc). Compared to standard chaotropic salt based methodology the phase separation solution is approximately 1,200 times better at removing endotoxins. It achieves approximately half the endotoxins of 2×CsCl gradient centrifugation and about 9-10 times less endotoxins compared to classic anion exchange methodology as estimated using commercially available information for commercially available products offered by QIAGEN'.

Example 8—Evaluation of Various Salts, pH, and N-Lauroylsarcosine Sodium Salt to Determine Preferred Capture Conditions for DNA Using Domiphen Bromide (DB)

For this experiment, JM109 was transformed with pGEM and cultures were grown overnight for 16 hours. The cells contained within 35 ml of culture were pelleted and suspended in 5 ml P1 buffer. The cells were then lysed using 5 ml P2 buffer for 3 minutes and the solution was neutralized and genomic DNA/proteins were precipitated using 5 ml P3 buffer that contained 1.0 M potassium acetate pH 4.9 and 200 µg/ml RNAse A. The precipitated cellular debris was cleared by using a glass fiber filter. 5 ml P4, a 1% domiphen bromide solution containing varying concentrations of salts, Tris or Bis-Tris, and N-Lauroylsarcosine sodium salt, was added to the cleared lysate prior to loading the solution onto a glass fiber matrix. The matrix was washed with 700 µl 0.6 M LiCl and then washed with 700 µl 95% ethanol. Finally, the captured nucleic acid was eluted. The various solutions are provided in Table 1. Each reaction was visualized by agarose gel electrophoresis at 5 min to check for the presence of RNA and again at 45 min to evaluate the full-length run.

This experiment showed that all of the above solutions provided a high degree of selectivity as indicated by the absence of degraded RNA in the gels (FIGS. 9A-B), with comparable recoveries of plasmid DNA (Table 2, bold values). 1% DB/2 M LiCl provided the highest recovery; however, it has a narrow window of selectivity and is therefore potentially more susceptible to deviations in volumes and concentrations. The higher sensitivity to user handling is not preferred despite the slightly higher recovery. Bis-Tris pH 7.0 appears to provide the highest recovery with reliability. Furthermore, (data not shown) as previously discussed, increasing salt concentration alone appeared to remove RNA degradation if processed immediately, however after short incubations the DB-RNA complex began to form again and was subsequently captured.

1.1 M Bis-Tris pH 7.0/1.5 M lithium chloride/1% domiphen bromide provided the second highest recovery at 709.1 ng/μL, which is only 30 ng/μL less than the 1% DB/2 M LiCl; however, it provided a larger window of selectivity as shown above. Currently the preferred solution for phase separation contains between about 0.25%-4% domiphen bromide between about 0.4-2.25 LiCl, between about 0-1.5 M Tris or Bis-Tris pH between about 7-8.5.

TABLE 2

Effect of pH, LiCl, and Sarcosine on capture capacity and RNA elimination

| Molarity of LiCl | pDNA (ng/μL) |
|---|---|
| Tris pH 8.5 (1.1M) | |
| 1 | 557.2 |
| 1.25 | 596.5 |
| Tris pH 8.5 (1.1M)/0.05% w/v Sarcosine | |
| 1 | 427.1 |
| 1.25 | 510.7 |
| Tris pH 8.5 (1.1M)/0.1% w/v Sarcosine | |
| 1 | 542.1 |
| 1.25 | 20.4 |
| Bis-Tris pH 7.0 (1.1M) | |
| 1.25 | 403.1 |
| 1.5 | 709.1 |
| Bis-Tris pH 7.0 (1.1M)/0.05% w/v Sarcosine | |
| 1.25 | 593.3 |
| 1.5 | 21.3 |
| Bis-Tris pH 7.0 (1.1M)/0.1% w/v Sarcosine | |
| 1.25 | 106.2 |
| 1.5 | 8.3 |
| Standard DB/LiCl only buffer | |
| 2 | 739.8 |
| Standard DB/LiCl/0.05% w/v Sarcosine | |
| 2 | 28.8 |
| Standard DB/LiCl/0.1% w/v Sarcosine | |
| 2 | N/A |

Example 9—Determination of Preferred Capture Conditions

For this experiment, JM109 was transformed with pGEM and cultures were grown overnight for 16 hours. The cells were contained within 35 ml of culture pelleted and suspended in 5 ml P1 buffer. The cells were then lysed using 5 ml P2 buffer for 3 minutes and the solution was neutralized and genomic DNA/proteins were precipitated using 5 ml P3 buffer that contained 1.0 M potassium acetate pH 4.9 and 200 μg/ml RNAse A. The precipitated cellular debris was cleared by using a glass fiber filter. 5 ml P4, a 1% DB solution containing varying concentration of salts, Tris or Bis-Tris, was added to the cleared lysate prior to loading the solution onto a glass fiber matrix. The matrix was washed with 700 μl 0.6 M LiCl and then washed with 700 μl 95% ethanol. Finally, the captured nucleic acid was eluted.

Three parameters evaluated using the three preferred phase separation buffer solutions. The parameters (see, Table 3) tested are as follows: total recovery from a standard prep, total recovery if two preps were loaded through the same column (indicated as 2x), and lastly if a 1 hour incubation in the phase separation buffer prior to loading it on the column affected recovery. Each reaction was visualized by agarose gel electrophoresis at 5 min to check for the presence of degraded RNA and again at 45 min to evaluate the full-length run (FIGS. 10A-B).

1.1 M Bis-Tris pH 7.0/1.5 M LiCl/1% DB outperformed the other two candidates and achieved the highest recovery of 231 μg and displayed the most consistent results (Table 3). 1% DB/1.1 M Bis-Tris pH 7.0/1.5 M LiCl was determined to be the preferred phase separation buffer based upon its high degree of selectivity and robustness in its recoveries. The recoveries were highly consistent which indicates that the system is robust in its ability to tolerate user handling. It is also highly selective in that the recoveries listed in the table were free of contaminating degraded RNA.

TABLE 3

Determination of capture conditions

| Phase Separation Buffer | Avg pDNA (ng/μL) | Std Dev | Total pDNA (μg) |
|---|---|---|---|
| 1.1M Tris pH 8.5/1.25M LiCl/1% DB | 544.7 | 68.0 | 108.9 |
| 1.1M Bis-Tris pH 7.0/1.5M LiCl/1% DB | 603.0 | 1.1 | 120.6 |
| 2M LiCl/1% DB | 635.6 | 42.5 | 127.1 |
| 1.1M Tris pH 8.5/1.25M LiCl/1% DB | 917.8 | 160.8 | 183.6 |
| 1.1M Bis-Tris pH 7.0/1.5M LiCl/1% DB | 1158.2 | 176.4 | 231.6 |
| 2M LiCl/1% DB | 976.9 | 129.5 | 195.4 |
| 1.1M Tris pH 8.5/1.25M LiCl/1% DB | 584.1 | 262.3 | 116.8 |
| 1.1M Bis-Tris pH 7.0/1.5M LiCl/1% DB | 653.3 | 39.5 | 130.7 |
| 2M LiCl/1% DB | 543.8 | 16.0 | 108.8 |

In order to further validate the preferred phase separation buffer conditions, plasmid DNA was "spiked" into the cleared lysate prior to adding the buffer. This was done to determine the maximum capture capacity using the 3 ply Alhstrom 141 (15 mg matrix) on the Zymo Spin V column. A stock solution of 542 ng/μL was used to add 100, 200, or 400 μL of pDNA solution. This solution was then mixed with 5 mL of phase separation buffer and loaded onto the column. Total recovery was measured using a Nanodrop™ (Table 4).

TABLE 4

Determining Recovery

| Volume of pGEM Added (ul) | pDNA (ng/ul) | Avg pDNA (ng/ul) | Fraction of pDNA Recovered |
|---|---|---|---|
| 100 | 606.60 | 668.40 | 0.72 |
| 100' | 730.20 | | |
| 200 | 856.70 | 898.50 | 0.75 |
| 200' | 940.30 | | |
| 400 | 1468.90 | 1488.60 | 0.86 |
| 400' | 1508.30 | | |

Example 10—Matrix Porosity vs. Nucleic Acid Recovery

The following experiment used neutralized bacterial lysate prepared from 35 mL of overnight culture that was loaded onto spin columns containing borosilicate glass fiber with a nominal particle retention rating of either 1.0 μm (Porex Grade B), 1.6 μm (Porex Grade A), or 2.7 μm (Porex Grade D) using a previously reported CTAB buffer. There was an enormous difference in the capture capacity between each of the grades of glass used that strongly correlates to the nominal particle retention rating (FIG. 11). This is counter intuitive as one would logically reason that a denser less porous matrix would be more effective at capture and collection of the CTAB/nucleic acid complex. The mostly likely reason for the slightly higher capture between the Porex Grade B and the Porex Grade A glass fibers is because the grade B had an additional 1-2 mg of matrix, thereby providing a slightly larger surface area for the CTAB/DNA complex to bind to. Despite the slight difference in recovery between Grade B and Grade A, the Grade D clearly demonstrated an unexpected significantly higher yield.

Example 11—Capture of Plasmid

Approximately 50 ml of culture containing JM109 transformed with pGEM plasmid was used for each preparation. About 8 ml of P1 was used to resuspend the cells. About 8 ml of P2 was used to lyse the cells for about 3 minutes. About 8 ml of P3 was used to neutralize the lysis buffer and precipitate debris such as protein and genomic DNA. The solution was cleared of precipitate by passing the solution through a filter. About 8 ml of P4 was added and mixed thoroughly.

Two of the samples (controls) were processed by directly loading them onto the silica filter followed by about 5 ml of a first wash and two 5 ml second washes.

Two other samples were centrifuged at 4,000×g for 15 minutes (experimental). A precipitate appeared at the bottom of these experimental samples following this centrifugation (FIG. 12, left). The supernatant was poured onto the silica filter and washed using the regiment described above. Both samples were eluted using 200 µl of 10 mM Tris pH 8.5 and 0.1 mM EDTA.

The plasmid DNA is selectively precipitated by the addition of the domiphen bromide under the conditions described above as indicated by the formation of a precipitate for the experimental sample but not for the controls (FIG. 12, left and right arrows respectively). Further confirmation that the precipitate does in fact contain plasmid DNA was determined by processing the supernatant of the samples post centrifugation (Table 5).

The samples that showed a supernatant contained approximately 10% of the DNA that the control groups contained indicating the precipitate contained a majority of the DNA. Therefore it appears that the capture mechanism by which the Domiphen bromide-DNA complex is retained is based on trapping it on the silica membrane (Table 5).

TABLE 5

Domiphen bromide Precipitation of Nucleic Acid.

| Sample (ng/ml) | Experimental | Control |
| --- | --- | --- |
| 1 | 64.0 | 353.3 |
| 2 | 38.0 | 315.6 |

Example 12—Further Evaluation of Tris-HCl and Bis-Tris Plasmid Preparation Using DB Substitution of Tris-HCl for Bis-Tris (control) for shifts the preferred LiCl concentration of Domiphen Bromide capture of plasmid DNA. The pGEM plasmid was purified from about 50 ml of overnight JM109 *E. coli* culture in duplicate using approximately 1% Domiphen Bromide, 1.40 M LiCl in 1.1 M Bis-Tris, pH 7.0 or alternately in approximately 1% Domiphen Bromide in 1.1 M Tris-HCl, pH 7.20 containing the LiCl concentrations shown. Samples were processed essentially as described in Example 9. About 10 µl of elution was visualized following 20 min (A) to check for undesirable RNA contamination (RNA Check) and 60 min (B) in a full length run to examine plasmid isolation in agarose gel electrophoresis. In each FIGS. 14 A-B the first two lanes are controls with Bis-Tris as the buffer component. LiCl concentrations are shown to titrate the preferred LiCl concentration. The Marker (M) is a 1 kb DNA Marker (Zymo Research Corp.) (FIG. 14). This experiment shows a preferred LiCl concentration of between about 0.6 M to about 1.05M with about 0.7 M, about 0.8 M, about 0.9M and about 1.0M LiCl being preferred with a Tris-HCL based capture buffer.

Example 13—Genomic DNA Extraction Using Novel Phase Separation Reagents

Various phase separation reagents were used to isolate nucleic acids from *E. coli* as a model for genomic DNA and RNA isolation to examine the widely unpredictable characteristics of such phase separation reagents to determine if genomic DNA could be efficiently isolated by the following protocol. The protocol for the ZR Fungal/Bacterial DNA MiniPrep was followed according to the manufacture suggested protocol to isolate DNA and as a measure of extraction efficiency. Approximately, 1 ml of bacterial culture was used for each experiment. Samples were centrifuged at 900×g for 1.5 minutes to pellet the cells, supernatants were discarded, the pellets were washed with 200 µl 1×PBS, centrifuged again at 900×g for 1.5 minutes to pellet the cells, supernatants discarded, and then the cells were resuspended using 200 µl of a solution containing 10 mM Tris HCl pH 8.5 and 0.1 mM EDTA prior to processing. The samples were pooled to ensure homogeneity during processing and subsequently lysed using 0.5 mm high-density beads (Zymo, ZR BeadBashing™ Kit) vortexed at 6.5 m/s in Sodium Chloride (NaCl) solutions of increasing final concentrations (see Table 6). The final concentration of NaCl in the samples tested ranged from about 0.5 M to about 1.0 M. Different cationic surfactants were added to a final concentration of 0.25%. The sample was loaded onto a commercially available Zymo Spin III-P column centrifuged at 10,000×g and subsequently washed with 700 µl 0.6 M LiCl and 700 µl and 95% ethanol (×2). The ZR Fungal/Bacterial DNA MiniPrep Kit was used as a control to for extraction efficiency according to the manufacture suggested protocol. The sample was by pelleting and bead bashing steps described as above utilizing the manufactures supplied Lysis Solution and adding three volumes of Genomic Lysis Buffer to the lysate. The sample was loaded onto a Zymo-Spin IIC column centrifuged at 16,000×g and subsequently washed with 200 µl DNA Pre-Wash Buffer and 500 µl g-DNA Wash Buffer. All samples were eluted in 100 µl DNA Elution Buffer (Zymo Research Corp.) after 5 min incubation at room temp.

TABLE 6

Evaluation of the extraction efficiency of different cationic detergents.

| | | Concentration (ng/µl) | Yield (µg) |
| --- | --- | --- | --- |
| 0.5M NaCl | 0.25% Lauroylcholine chloride hydrate | 40.3 | 4.03 |
| 0.7M NaCl | 0.25% Lauroylcholine chloride hydrate | 1.8 | 0.18 |

TABLE 6-continued

Evaluation of the extraction efficiency of different cationic detergents.

| | | Concentration (ng/μl) | Yield (μg) |
|---|---|---|---|
| 0.9M NaCl | 0.25% Lauroylcholine chloride hydrate | 1.4 | 0.14 |
| 1M NaCl | 0.25% Lauroylcholine chloride hydrate | 0 | 0 |
| 0.5M NaCl | 0.25% 1,3-dideoyl-2-methylimidazolium chloride | 229.3 | 22.93 |
| 0.7M NaCl | 0.25% 1,3-dideoyl-2-methylimidazolium chloride | 101.5 | 10.15 |
| 0.9M NaCl | 0.25% 1,3-dideoyl-2-methylimidazolium chloride | 8.4 | 0.84 |
| 1M NaCl | 0.25% 1,3-dideoyl-2-methylimidazolium chloride | 6.5 | 0.65 |
| 0.5M NaCl | 0.25% octylimidazolium chloride | 2.4 | 0.24 |
| 0.7M NaCl | 0.25% octylimidazolium chloride | 1.7 | 0.17 |
| 0.9M NaCl | 0.25% octylimidazolium chloride | 1.4 | 0.14 |
| 1M NaCl | 0.25% octylimidazolium chloride | 1.2 | 0.12 |
| 0.5M NaCl | 0.25% 1-dodecyl-2-methyl-3-benzylimidazolium chloride | 42.2 | 4.22 |
| 0.7M NaCl | 0.25% 1-dodecyl-2-methyl-3-benzylimidazolium chloride | 76.2 | 7.62 |
| 0.9M NaCl | 0.25% 1-dodecyl-2-methyl-3-benzylimidazolium chloride | 55.8 | 5.58 |
| 1M NaCl | 0.25% 1-dodecyl-2-methyl-3-benzylimidazolium chloride | 6.9 | 0.69 |
| 0.5M NaCl | 0.25% Domiphen Bromide | 208.8 | 20.88 |
| 0.7M NaCl | 0.25% Domiphen Bromide | 158.1 | 15.81 |
| 0.9M NaCl | 0.25% Domiphen Bromide | 1.3 | 0.13 |
| 1M NaCl | 0.25% Domiphen Bromide | 6.3 | 0.63 |
| 0.5M NaCl | 0.25% cetylpyridinium chloride | 133.3 | 13.33 |
| 0.7M NaCl | 0.25% cetylpyridinium chloride | 84.4 | 8.44 |
| 0.9M NaCl | 0.25% cetylpyridinium chloride | 0.1 | 0.01 |
| 1M NaCl | 0.25% cetylpyridinium chloride | 0 | 0 |
| 0.5M NaCl | 0.25% benzethonium chloride | 216 | 21.6 |
| 0.7M NaCl | 0.25% benzethonium chloride | 147.9 | 14.79 |
| 0.9M NaCl | 0.25% benzethonium chloride | 5.3 | 0.53 |
| 1M NaCl | 0.25% benzethonium chloride | 3.4 | 0.34 |
| 0.5M NaCl | 0.25% 1-dodecyl pyridinium chloride hydrate | 11.6 | 1.16 |
| 0.7M NaCl | 0.25% 1-dodecyl pyridinium chloride hydrate | 3.9 | 0.39 |
| 0.9M NaCl | 0.25% 1-dodecyl pyridinium chloride hydrate | −0.1 | −0.01 |
| 1M NaCl | 0.25% 1-dodecyl pyridinium chloride hydrate | 0 | 0 |

The efficiency for DNA extraction and selectivity of the cationic surfactants was evaluated via spectrophotometry and visualized by agarose gel electrophoresis after 45 min (FIGS. 15A-B). Varying selectivity was observed for DNA and RNA for the different cationic detergents tested. Laurylcholine chloride hydrate showed nearly no binding of genomic DNA at the concentrations of NaCl evaluated (e.g. about 0.5 M to about 1.0 M). At about 0.5 M sodium chloride the RNA was selectively bound which was a completely unexpected phenomenon. The surfactant 1,3 didecyl-2-methylimidazolium chloride demonstrated an ability to selectively bind nucleic acids (tunability) as seen by the selective binding of genomic DNA and RNA at 0.5 and 0.7 M NaCl respectively (FIG. 15A). This trend is the opposite of what was observed for domiphen bromide in the context of the plasmid DNA isolation embodiments described in other embodiments where the smaller nucleic acids were selectively removed as NaCl was added under both near neutral and basic conditions. Under acidic conditions the degraded RNA was not robustly and efficiently removed. In the range of concentrations tested another surfactant octylimidazolium did not bind nucleic acids. Still another surfactant 1-dodecyl-2-methylimidazolium chloride showed the ability to selectively remove large nucleic acids while retaining RNA (tunability). Furthermore, DNA was selectively bound in preference to RNA at lower concentrations of NaCl. Domiphen bromide was not tunable using salt alone under the conditions used for genomic DNA isolation. The surfactant Cetylpyridinium chloride contrary to its performance for the plasmid DNA isolation embodiments selectively removed large DNA molecules showing tunability. The surfactant Benzethonium chloride behaved similarly to Cetylpyridinium chloride. The surfactant 1-dodecyl pyridinium chloride did not bind nucleic acids under any of the conditions which were unexpected, as this molecule showed exemplary binding of all sized nucleic acids under the conditions of the plasmid preparation. These results show that genomic DNA can be efficiently isolated with the described phase separation reagents but that each individual phase separation reagent displays different properties.

In addition to the isolation of genomic DNA from the cells, the phase separation reagents also showed an ability to selectively isolate RNA (example: cetylpyridinium chloride.) Furthermore, the phase separation reagents all show varying capabilities to isolate RNA. For example, under the conditions tested Lauroylcholine chloride hydrate, 1,3-dideoyl-2-methylimidazolium chloride, and 1-dodecyl-2-methyl-3-benzylimidazolium chloride indicated an ability to selectively isolate smaller RNA molecules in preference to larger genomic DNA.

Example 14—Genomic DNA Isolation Using Domiphen Bromide

Domiphen Bromide was further examined for the selective isolation of genomic DNA as well as RNA from human cells (HeLa cells) by the following protocol. The protocol for the Quick-gDNA MiniPrep was followed according to the manufacture suggested protocol. Approximately, 1.5 million cells were resuspended using 200 μl of a pH 8.5, 10 mM Tris 0.1 mM EDTA solution, pooled to ensure homogenous mixtures, and bead bashed for 30 seconds using 0.5 mm high-density beads vortexed at 6.5 m/s in NaCl or LiCl solutions of increasing final concentrations of about 0.5-0.8M (see Tables 7 and 8). The Quick-gDNA MiniPrep was used as a control to for extraction efficiency. The control samples were processed using the manufacturer's provided lysis solution for bead bashing. Three volumes of Genomic Lysis Buffer were added to the lysate. The sample was loaded onto a Zymo-Spin IIC column centrifuged at 16,000×g and subsequently washed with 200 μl DNA Pre-Wash Buffer and 500 μl g-DNA Wash Buffer. For experimental groups, Domiphen bromide was added to a final concentration of about 0.25%. The sample was loaded onto a column (Zymo Spin III-P column), and centrifuged at 10,000×g, for 1 minute, washed with 700 μl 0.6 M LiCl and centrifuged at ≥16,000×g, for 1 minute more, and then twice washed with 700 μl 95% ethanol and centrifuged at ≥16,000×g, for 1 minute more. All samples were eluted in 100 μl DNA Elution Buffer (Zymo Research Corp.) after 5 min incubation at room temperature (RT). Each sample was also evaluated via spectrophotometry and visualized by agarose gel electrophoresis at 5 min to check for the presence of degraded RNA and again at 45 min to evaluate the full-length run (FIGS. 16-17).

TABLE 7

Determination of binding conditions using NaCl.

|  | Average Recovery (ng/μl) | Standard Deviation (St. Dev.) | Average Yield (μg) |
|---|---|---|---|
| Control | 31.60 | 0.85 | 3.16 |
| 0.57M Nacl | 64.35 | 10.96 | 6.44 |
| 0.59M NaCl | 48.80 | 20.08 | 4.88 |
| 0.61M NaCl | 31.70 | 9.19 | 3.17 |
| 0.63M NaCl | 20.95 | 11.38 | 2.10 |
| 0.65M NaCl | 13.55 | 8.70 | 1.36 |
| 0.68M NaCl | 7.65 | 4.60 | 0.77 |

TABLE 8

Determination of binding conditions using LiCl.

|  | Average Recovery (ng/μl) | Stdev | Average Yield (μg) |
|---|---|---|---|
| Control | 15.70 | 1.56 | 1.57 |
| 0.5M LiCl | 89.80 | 11.17 | 8.98 |
| 0.61M LiCl | 97.70 | 4.38 | 9.77 |
| 0.7M LiCl | 13.15 | 2.19 | 1.32 |
| 0.75M LiCl | 2.10 | 1.13 | 0.21 |
| 0.8M LiCl | 0.45 | 0.21 | 0.05 |

Domiphen bromide displayed enrichment of isolated genomic DNA when various salts such as sodium chloride and lithium chloride were increased in concentration. For example, Domiphen bromide in the presence of increasing the concentrations of NaCl demonstrated the ability to selectively bind larger DNA while smaller nucleic acids passed through the filter (FIG. 16). When Lithium chloride (LiCl) was used it proved to be less selective showing decreased ability to selectively bind different sized DNA fragments over the conditions tested (FIG. 17) Indicating that the type of cation used affects the selective power of Domiphen bromide.

Example 15—Binding the Surfactant-Nucleic Acid Complex to Magnetic Beads

Domiphen Bromide was further evaluated for isolation of genomic DNA as well as RNA using magnetic-silica particles as the solid phase carrier. The following experiments used *Saccharomyces cerevisiae* as the model organism. The protocol for the ZR Fungal/Bacterial DNA MiniPrep was followed according to the manufacture suggested protocol. Approximately, 50 mg wet weight of yeast cells was resuspended using 200 μl of a Tris-EDTA solution, pooled to ensure homogenous mixtures, and lysed by vortexing (bead bashed) using 0.5 mm high-density beads at 6.5 m/s to lyse the yeast cells in NaCl solutions of increasing final concentrations. For the control group, the manufacturer's provided lysis solution was utilized for bead bashing. Three volumes of Genomic Lysis Buffer were added to the lysate. The sample was loaded onto a Zymo-Spin II column centrifuged at 16,000×g and subsequently washed with 200 μl DNA Pre-Wash Buffer and 500 μl g-DNA Wash Buffer. For experimental groups, Domiphen Bromide was added to a final concentration of about 0.25%. Approximately, 30 μl of Magnetic Beads were added to each sample and were washed with 700 μl 0.6 M LiCl and 700 μl 95% ethanol (×2). All samples were eluted in 45 μl DNA Elution after 5 min incubation at room temperature Buffer (Zymo Research Corp.). Each sample was evaluated via spectrophotometry and visualized by agarose gel electrophoresis after 45 min (FIG. 18).

TABLE 9

Compatibility of novel surfactants for nucleic acid purification.

|  | Average Recovery (ng/μl) | Stdev | Average Yield (μg) |
|---|---|---|---|
| Column Control | 81.70 | 1.56 | 8.17 |
| MagBead - 0.06M NaCl | 2233.70 | 79.05 | 223.37 |
| MagBead - 0.11M NaCl | 2329.05 | 32.88 | 232.91 |
| MagBead - 0.45M NaCl | 2048.00 | 60.81 | 204.80 |

This experiment demonstrated that the Domiphen bromide-nucleic acid complex binds directly to magnetic-silica beads. This was unexpected as precipitation was demonstrated in embodiments utilizing centrifugation. Therefore, without being bound to a particular theory it appears that the mode of capture is unexpectedly of a dual action—both precipitation and binding.

Example 16—Titration of Buffer, pH, and NaCl to Optimize Genomic DNA Binding Using Domiphen Bromide Experiments using *E. coli* as the model system for genomic DNA isolation were performed with Domiphen Bromide to assess the effects of buffer composition and pH in order to better understand isolation efficiencies, selectivity, and tunability. The protocol for the ZR Fungal/Bacterial DNA MiniPrep was followed according to the manufacture suggested protocol and approximately 1 ml of bacterial culture was used for each isolation. Samples were centrifuged to pellet the cells, supernatants were discarded, the pellets were washed with 200 μl 1×PBS, centrifuged, supernatants discarded, and then the cells were resuspended using 200 μl of a solution containing 10 mM Tris HCl pH 8.5 and 0.1 mM EDTA prior to processing. The samples were pooled to ensure homogeneity during processing and subsequently lysed (bead bashed) using 0.5 mm high-density beads at 6.5 m/s in NaCl solutions of increasing final concentrations. The ZR Fungal/Bacterial DNA MiniPrep was used as a control to for extraction efficiency. For the control group, the manufacturer's provided lysis solution was utilized for bead bashing. Three volumes of Genomic Lysis Buffer were added to the lysate. The sample was loaded onto a Zymo-Spin II column centrifuged at 16,000×g and subsequently washed with 200 μl DNA Pre-Wash Buffer and 500 μl g-DNA Wash Buffer. For experimental groups, the final concentration of NaCl in the samples tested ranged from about 0.5 to about 1 M. Domiphen Bromide was added to a final concentration of about 0.25% along with a Tris, KoAC, or Bis-Tris based buffers at about 50 mM final concentration. Domiphen Bromide was added to a final concentration of about 0.25%. The sample was loaded onto a column (Zymo Spin III-P column), and centrifuged at 10,000×g, for 1 minute, washed with 700 μl 0.6 M LiCl and centrifuged at ≥16,000×g, for 1 minute more, and then twice washed with 700 μl 95% ethanol and centrifuged at ≥16,000×g, for 1 minute more. All samples were eluted in 100 μl DNA Elution Buffer after a 5 min incubation at room temp (Zymo Research Corp.). The efficiency and selectivity of the cationic surfactants was evaluated via spectrophotometry and visualized by agarose gel electrophoresis after 45 min (FIGS. 19A-B).

TABLE 10

Genomic DNA binding in the presence of a buffer.

| Con | | Average Recovery (ng/μl) | Stdev | Average Yield (μg) |
|---|---|---|---|---|
| Con | Control | 19.45 | 5.30 | 1.95 |
| 1 | 0.7 NaCl <50 mM Tris 8.0 | 41.95 | 15.91 | 4.20 |
| 2 | 0.8M NaCl 50 mM KoAc pH 5.6 | 1.65 | 1.06 | 0.17 |
| 3 | 0.7M NaCl 50 mM KoAc pH 5.6 | 26.10 | 7.64 | 2.61 |
| 4 | 0.6M NaCl 50 mM KoAc pH 5.6 | 67.15 | 6.29 | 6.72 |
| 5 | 0.5M NaCl 50 mM KoAc pH 5.6 | 76.20 | 0.42 | 7.62 |
| 6 | 0.8M NaCl 50 mM Bis-Tris pH 7.0 | 1.05 | 0.78 | 0.11 |
| 7 | 0.7M NaCl 50 mM Bis-Tris pH 7.0 | 20.65 | 4.31 | 2.07 |
| 8 | 0.6M NaCl 50 mM Bis-Tris pH 7.0 | 69.85 | 5.59 | 6.99 |
| 9 | 0.5M NaCl 50 mM Bis-Tris pH 7.0 | 79.15 | 5.16 | 7.92 |
| 10 | 0.8M NaCl 50 mM Tris pH 7.2 | 1.50 | 0.28 | 0.15 |
| 11 | 0.7M NaCl 50 mM Tris pH 7.2 | 11.65 | 0.64 | 1.17 |
| 12 | 0.6M NaCl 50 mM Tris pH 7.2 | 71.10 | 8.06 | 7.11 |
| 13 | 0.5M NaCl 50 mM Tris pH 7.2 | 78.05 | 3.61 | 7.81 |

Both acidic and neutral conditions appeared to enhance the selectivity of nucleic acid binding using domiphen bromide with increasing concentrations of sodium chloride (FIGS. 19A-B). As concentration of sodium chloride increased smaller nucleic acids such as RNA were selectively removed. At lower concentrations of NaCl domiphen bromide facilitated binding of all nucleic acids. This is contrary to what was observed using the popular surfactant CTAB disclosed by Thorsten Singer (U.S. Pat. App. 2008/0113348) who showed that acidic conditions favored binding of both large and small fragments, meaning domiphen bromide has completely different and unique characteristics that could not have been predicted based upon the literature currently available.

Example 16—Isolation of DNA from an Adhesive

The objective of this experiment is to determine if water soluble tape that could be used for lifting cells from a surface for applications such forensics will inhibit DNA purification and downstream applications. The tape evaluated was Scotch brand No. 5414 Water Soluble Wave Solder Tape. It was found that using chaotropic salt based purification techniques that the Solder Tape interfered with purification. However the phase separation reagent technology allowed for purification to be achieved that was usable in PCR.

E. coli transformed with pGEM® and grown for 16 hours was used for proof of principle. 1 ml of culture was centrifuged and the supernatant was discarded. The cells were resuspended with 200 μl water that was dissolved in water. 0.5 inches of tape was dissolved by allowing it to incubate for 15 minutes at 55° C. The control sample was resuspended using 200 μl water. 200 μl of the mixture was transferred to BeadBashing Lysis Tube (0.5 mm). 550 μl of 0.91 M NaCl in pH 8.0 Tris/EDTA. The sample was mechanically lysed using MP Bio Fastprep-24 to bead bash the cells. Other methods of lysis such as direct chemical lysis are also possible methods of achieving the same result. The BeadBashing Lysis Tubes were centrifuged for 1 min at 10,000×g for 1 min. 300 μl of lysate was transferred to clean Eppendorf tubes and 100 μl 1% Domiphen Bromide 200 mM Potassium Acetate was added to the sample and was mixed. 400 μl of mixture was transferred to a Zymo Spin IIIP silica spin column and centrifuged at maximum speed for 1 min. The sample was subsequently washed with 700 μl 0.6 M LiCl and centrifuged at ≥16,000×g, for 1 minute more, and then twice washed with 700 μl 95% ethanol and centrifuged at ≥16,000×g, for 1 minute. As a comparative sample a commercially available system from Zymo Research Corporation that uses chaotropic salts, Quick-gDNA, was used to process the sample resuspended in the presence of the dissolved tape according to the standard protocol for processing liquid samples containing cells. Three volumes of Genomic Lysis Buffer were added to the lysate. The sample was loaded onto a Zymo-Spin II column centrifuged at 16,000×g and subsequently washed with 200 μl DNA Pre-Wash Buffer and 500 μl g-DNA Wash Buffer.

TABLE 11

Spectrophotometric results comparing the Phase Separation Reagent DB to Genomic Lysis Buffer for the preparation of DNA from a solution containing water dissolvable tape

| Sample ID | Date | ng/ul | A260 | A280 | 260/280 | 260/230 | Constant |
|---|---|---|---|---|---|---|---|
| Control 1 | Nov. 12, 2014 | −0.54 | −0.011 | −0.018 | 0.58 | 0.06 | 50 |
| Control 2 | Nov. 12, 2014 | −0.41 | −0.008 | −0.022 | 0.37 | 0.05 | 50 |
| Control 3 | Nov. 12, 2014 | −0.67 | −0.013 | −0.01 | 1.38 | 0.07 | 50 |
| Experimental 1 | Nov. 12, 2014 | 24.63 | 0.493 | 0.232 | 2.13 | 2.14 | 50 |
| Experimental 2 | Nov. 12, 2014 | 15.62 | 0.312 | 0.128 | 2.44 | −4.05 | 50 |
| Experimental 3 | Nov. 12, 2014 | 18.35 | 0.367 | 0.166 | 2.21 | −5.63 | 50 |

TABLE 12 qPCR results comparing the Phase Separation Reagents DB to Genomic Lysis Buffer
for the preparation of DNA from a solution containing water dissolvable tape

| Genomic Lysis Buffer | | | Phase Separation Solution | | | |
|---|---|---|---|---|---|---|
| Control 1 | Control 2 | Control 3 | Experimental 1 | Experimental 2 | Experimental 3 | Neg C |
| 24.17 | 23.94 | 33.47 | 15.38 | 16.08 | 15.43 | 33.30 |
| 25.30 | 24.08 | 24.20 | 15.61 | 15.96 | 15.47 | 33.93 |

DNA isolated using the DB based phase separation enabled direct purification of DNA from cells in a solution of dissolved brand No. 5414 Water Soluble Wave Solder Tape due to is high specificity for DNA. This exemplifies the broad utility of these phase separation reagents in new applications for purification of nucleic acids. Furthermore, due to the application of this purification technology the use of water soluble tape could be utilized for the purification of cells, including human for applications in forensics.

Example 18—Treatment Solution Boosts Yields but does not Remove Degraded RNA

A treatment solution was evaluated with increasing concentrations of sodium chloride to determine whether the salt treatment could be used to remove degraded RNA as well as provide the boost in recovery previously shown.

For this, JM109 cells transformed with pGEM were grown overnight for 16 hours. The cells contained within 10 ml of culture were pelleted and suspended in 5 ml P1 buffer. The cells were then lysed using 5 ml P2 buffer for 3 minutes and the solution was neutralized and genomic DNA/proteins were precipitated using a 5 ml P3 buffer that contained 1.0 M potassium acetate at about pH 4.9 and 200 µg/ml RNAse A. The precipitated cellular debris was cleared by using a glass fiber filter. 5 ml of the phase separation solution containing 1% w/v DB and 0.25 M lithium chloride was added prior to loading the solution onto a glass fiber matrix. The matrix was washed with 700 µl of 0, 0.1, 0.2, 0.5, and 0.7 M NaCl of the treatment solution and was subsequently washed with 700 µl 95% ethanol. Finally, the captured nucleic acid was eluted. Each reaction was visualized by agarose gel electrophoresis at 5 min as to check for the presence of RNA and again at 45 min to evaluate the full-length run (FIGS. 20A-B)

With increasing concentration of sodium chloride in the treatment solution yields were boosted as previously shown, however small nucleic acids such as the degraded RNA in this example was not removed. This is contrary to the popular cationic surfactant CTAB which uses a salt wash for removal of degraded RNA (U.S. Pat. App. 2008/0113348). The DB-NA complex not only receives a boost in recovery when treated with the salt solution it also retains the RNA complex indicating the uniqueness of these phase separation reagents and their unpredictability based on current literature available. Furthermore, DB possesses the ability to remove RNA during the binding step when the conditions were optimized (See other examples).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.
U.S. Pat. No. 7,754,873
U.S. Pat. No. 7,867,751
U.S. Pat. No. 8,679,744
U.S. Patent App. 2008/0113348
Bimboim, *Meth. in Enzym.*, 100:243-255, 1983.
Bimboim and Dolly, *Nucl. Acids Res.*, 7:1513-1523, 1979.
Clewell and Helinski, *Biochemistry*, 9:4428-4440, 1970.
Holmes and Quigley, *Anal. Biochem.*, 114:193-197, 1981.
Lis and Schleif, *Nucl. Acids Res.*, 2:757, 1975.
Marko et al., *Analyt. Biochem.*, 121:382-387, 1981.
Vogelstein et al., *Proc. Nat. Acad. Sci.*, 76:615-619, 1979.

What is claimed is:

1. A method of isolating plasmid DNA by alkaline lysis, comprising:
   (a) resuspending cells comprising plasmid DNA in a first aqueous solution;
   (b) lysing the cells with a second solution, thereby generating a lysate comprising the plasmid DNA;
   (c) neutralizing the lysate with a third solution;
   (d1) capturing the plasmid DNA to a mineral matrix with a phase separation solution comprising domiphen bromide and in the presence of 0.1 M to 0.7 M LiCl salt;
   (d2) removing the phase separation solution from the mineral matrix and captured plasmid DNA;
   (e) washing the mineral matrix and captured plasmid DNA with a salt solution, thereby enhancing the retention of captured plasmid DNA;
   (f) washing the mineral matrix and captured plasmid DNA with an organic wash solution; and
   (g) eluting the plasmid DNA from the mineral matrix, thereby isolating the plasmid DNA.

2. The method of claim 1, wherein neutralizing the lysate further comprises precipitating genomic DNA and/or proteins with the third solution.

3. The method of claim 2, further comprising clearing the precipitate after step (c).

4. The method of claim 1, wherein the second solution comprises sodium hydroxide and sodium dodecyl sulfate.

5. The method of claim 1, wherein the third solution comprises potassium acetate and RNAse A.

6. The method of claim 5, wherein the potassium acetate is present at a concentration of about 0.8 M to about 3 M.

7. The method of claim 1, wherein the first solution, the second solution, or the phase separation reagent comprises a dye.

8. The method of claim 1, wherein the isolated plasmid DNA is essentially free of endotoxin and/or PCR inhibitors.

9. The method of claim 1, wherein the mineral matrix is silica-based.

10. The method of claim 9, wherein the mineral matrix is borosilicate glass fiber.

11. The method of claim 1, wherein (e) washing the mineral matrix and captured DNA comprises washing with a salt solution comprising sodium chloride.

12. The method of claim 1, wherein (e) washing the mineral matrix and captured plasmid DNA with a salt solution comprises washing with a solution comprising a lithium salt, a sodium salt, a potassium salt, a magnesium salt, a calcium salt, or a mixture thereof.

13. The method of claim 12, wherein the salt solution provides a 0.1 M to 1.0 M concentration of NaCl, KCl, or LiCl.

14. The method of claim 1, wherein (e) washing the mineral matrix and captured plasmid DNA with a salt solution comprises washing with a solution having a salt concentration of 0.1 M to 1.0 M.

15. The method of claim 14, wherein (e) washing the mineral matrix and captured plasmid DNA with a salt solution comprises washing with a solution having a LiCl concentration of 0.1 M to 1.0 M.

16. The method of claim 1, wherein step (d1) comprises capturing the plasmid DNA to the mineral matrix in the presence of at least 0.5 M LiCl.

17. The method of claim 1, wherein the organic wash solution comprises an alcohol.

18. The method of claim 17, wherein the organic wash solution comprises at least 60% ethanol or isopropanol.

19. The method of claim 1, wherein the phase separation solution of (d1) comprises 0.05% (w/v) to 2% (w/v) domiphen bromide.

20. The method of claim 1, wherein the phase separation solution of (d1) comprises 0.05% (w/v) to 1% (w/v) domiphen bromide.

* * * * *